(12) United States Patent  
Sappenfield

(10) Patent No.: US 8,668,618 B2  
(45) Date of Patent: *Mar. 11, 2014

(54) ROTARY UNITS, ROTARY MECHANISMS, AND RELATED APPLICATIONS

(76) Inventor: Christopher C. Sappenfield, San Diego, CA (US)

( * ) Notice: Subject to any disclaimer, the term of this patent is extended or adjusted under 35 U.S.C. 154(b) by 281 days.

This patent is subject to a terminal disclaimer.

(21) Appl. No.: 13/184,332

(22) Filed: Jul. 15, 2011

(65) Prior Publication Data

US 2011/0290052 A1 Dec. 1, 2011

Related U.S. Application Data

(63) Continuation-in-part of application No. 12/577,326, filed on Oct. 12, 2009, now Pat. No. 8,152,679, which is a continuation of application No. PCT/US2009/060386, filed on Oct. 12, 2009.

(60) Provisional application No. 61/104,748, filed on Oct. 12, 2008, provisional application No. 61/365,290, filed on Jul. 16, 2010, provisional application No. 61/376,725, filed on Aug. 25, 2010.

(51) Int. Cl.  
*F16H 57/08* (2006.01)

(52) U.S. Cl.  
USPC .......................................................... 475/331

(58) Field of Classification Search  
USPC .......................................................... 172/216  
See application file for complete search history.

(56) References Cited

U.S. PATENT DOCUMENTS

| 75,676 A | * | 3/1868 | Goodwing | 475/337 |
| 845,103 A | * | 2/1907 | Ljungstrom | 475/335 |
| 1,059,450 A | | 4/1913 | Foote | |
| 1,489,817 A | | 4/1924 | Campbell | |
| 1,887,429 A | | 11/1932 | Price | |
| 2,851,905 A | | 9/1958 | Clark | |
| 2,905,451 A | | 9/1959 | Callanen et al. | |
| 2,950,634 A | | 8/1960 | Clark | |
| 3,088,414 A | | 5/1963 | Cahit | |

(Continued)

FOREIGN PATENT DOCUMENTS

| CN | 2619094 | 6/2004 | |
| JP | 05332413 | 12/1993 | |
| JP | 05332413 A | * 12/1993 | F16H 13/08 |
| WO | WO2010042934 | 4/2010 | |

OTHER PUBLICATIONS

International Search Report for International (PCT) Patent Application No. PCT/US2009/060386, mailed Nov. 25, 2009.  
Written Opinion for International (PCT) Patent Application No. PCT/US2009/060386, mailed Nov. 25, 2009.  
International Preliminary Report on Patentability for International (PCT) Patent Application No. PCT/US2009/060386, mailed Apr. 21, 2011.

(Continued)

*Primary Examiner* — Dirk Wright  
(74) *Attorney, Agent, or Firm* — Christopher C. Sappenfield

(57) ABSTRACT

The invention relates to rotary units and rotary mechanisms that are suitable for use in numerous applications. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate.

13 Claims, 24 Drawing Sheets

(56) References Cited

U.S. PATENT DOCUMENTS

| | | | |
|---|---|---|---|
| 3,222,533 A | | 12/1965 | Mackay |
| 3,892,278 A | | 7/1975 | Smith et al. |
| 3,913,415 A | * | 10/1975 | Herr .............................. 475/124 |
| 4,044,841 A | | 8/1977 | Smith et al. |
| 4,132,131 A | | 1/1979 | DeBruyne |
| 4,159,624 A | | 7/1979 | Gruner |
| 4,334,440 A | | 6/1982 | Fonck |
| 4,365,525 A | * | 12/1982 | Imazaike ....................... 475/337 |
| 4,464,095 A | | 8/1984 | Iida |
| 4,535,653 A | | 8/1985 | Coburn |
| 4,611,504 A | | 9/1986 | Rundle |
| 4,627,310 A | | 12/1986 | Coburn |
| 4,683,897 A | | 8/1987 | McBride |
| 4,732,053 A | * | 3/1988 | Gleasman et al. .......... 74/665 L |
| 4,763,031 A | | 8/1988 | Wang |
| 4,825,727 A | * | 5/1989 | Komuro ............................ 74/413 |
| 4,896,567 A | | 1/1990 | Zhou et al. |
| 4,926,715 A | | 5/1990 | Hirt et al. |
| 5,014,428 A | | 5/1991 | Yamashita |
| 5,426,806 A | | 6/1995 | Johnson et al. |
| 5,595,147 A | | 1/1997 | Feuling |
| 5,679,089 A | | 10/1997 | Levedahl |
| 5,724,867 A | * | 3/1998 | Jordan ......................... 74/665 K |
| 5,870,790 A | | 2/1999 | Root |
| 6,032,313 A | | 3/2000 | Tsang |
| 6,176,804 B1 | | 1/2001 | Kekki et al. |
| 6,179,503 B1 | | 1/2001 | Taghavi-Khanghah |
| 6,213,224 B1 | * | 4/2001 | Furuta et al. .................. 173/217 |
| 6,222,293 B1 | | 4/2001 | Ikeda et al. |
| 6,357,118 B1 | | 3/2002 | Eichhorn et al. |
| 6,379,276 B1 | * | 4/2002 | Cheng .............................. 475/4 |
| 6,418,810 B1 | | 7/2002 | Kerr |
| 6,492,743 B1 | | 12/2002 | Appa |
| 6,626,792 B2 | | 9/2003 | Vranish |
| 6,669,594 B2 | | 12/2003 | Kerr |
| 6,672,538 B2 | | 1/2004 | Millea et al. |
| 6,732,603 B1 | | 5/2004 | Hsu et al. |
| 6,799,579 B2 | | 10/2004 | Joseph |
| 6,829,457 B2 | * | 12/2004 | Ryuzaki et al. ............... 399/167 |
| 7,021,851 B1 | | 4/2006 | King |
| 7,022,042 B2 | | 4/2006 | Fleytman |
| 7,063,173 B2 | * | 6/2006 | Herla ............................ 173/216 |
| 7,108,629 B2 | | 9/2006 | Hiraiwa |
| 7,118,340 B2 | | 10/2006 | D'Anna |
| 7,153,004 B2 | | 12/2006 | Galli |
| 7,181,799 B2 | | 2/2007 | Gavney |
| 7,182,708 B2 | * | 2/2007 | Winzeler ....................... 475/337 |
| 7,296,495 B2 | * | 11/2007 | Quinn .............................. 74/640 |
| 7,413,025 B2 | * | 8/2008 | Provost .......................... 173/29 |
| 7,784,731 B2 | * | 8/2010 | Lin ............................ 244/17.23 |
| 7,967,740 B2 | | 6/2011 | Mertens |
| 7,993,067 B2 | | 8/2011 | Hall et al. |
| 8,042,217 B2 | | 10/2011 | Sorrentino |
| 8,046,861 B2 | | 11/2011 | Joseph |
| 8,056,175 B2 | | 11/2011 | Kunita et al. |
| 8,087,843 B2 | | 1/2012 | Ottaviani et al. |
| 8,152,679 B2 | * | 4/2012 | Sappenfield .................. 475/221 |
| 8,250,694 B2 | | 8/2012 | Gatzemeyer |
| 8,276,231 B2 | | 10/2012 | Gavney |
| 8,277,358 B2 | * | 10/2012 | Gasparrini et al. ........... 475/331 |
| 8,302,238 B2 | | 11/2012 | Biro |
| 8,316,496 B2 | | 11/2012 | Al-Qaffas |
| 8,358,029 B2 | | 1/2013 | Burkart |
| 2003/0113133 A1 | | 6/2003 | Ryuzaki |
| 2003/0220169 A1 | | 11/2003 | Norman |
| 2007/0249460 A1 | | 10/2007 | Schulz et al. |
| 2008/0070739 A1 | | 3/2008 | Nakamura et al. |
| 2008/0134513 A1 | * | 6/2008 | Oh ................................ 30/43.6 |
| 2008/0205970 A1 | | 8/2008 | LaFlamme et al. |
| 2008/0233815 A1 | | 9/2008 | Nakamura et al. |
| 2009/0136285 A1 | | 5/2009 | Hall et al. |
| 2010/0089200 A1 | | 4/2010 | Sappenfield |
| 2010/0175214 A1 | | 7/2010 | Payet |
| 2010/0272500 A1 | | 10/2010 | Martin et al. |
| 2011/0232013 A1 | | 9/2011 | Sappenfield |
| 2011/0308351 A1 | * | 12/2011 | Sappenfield .................. 74/665 F |
| 2012/0010039 A1 | * | 1/2012 | Sappenfield .................. 475/331 |
| 2012/0010040 A1 | * | 1/2012 | Sappenfield .................. 475/331 |
| 2012/0180586 A1 | * | 7/2012 | Sappenfield ................. 74/412 R |
| 2012/0196719 A1 | * | 8/2012 | Sappenfield .................. 475/331 |
| 2012/0202641 A1 | * | 8/2012 | Sappenfield .................. 475/337 |
| 2013/0214627 A1 | | 8/2013 | Sappenfield |

OTHER PUBLICATIONS

U.S. Appl. No. 61/104,748.
U.S. Appl. No. 61/365,290.
U.S. Appl. No. 61/376,725.
U.S. Appl. No. 61/640,530.
Co-pending U.S. Appl. No. 13/423,413, filed Mar. 19, 2012.
Co-pending U.S. Appl. No. 13/442,850, filed Apr. 9, 2012.
Co-pending U.S. Appl. No. 13/451,468, filed Apr. 19, 2012.
Office Action mailed Nov. 21, 2011 for U.S. Appl. No. 12/577,326.
Examiner Interview Summary mailed Dec. 30, 2011 for U.S. Appl. No. 12/577,326.
Notice of Allowance mailed Feb. 24, 2012 for U.S. Appl. No. 12/577,326.
Office Action mailed Jun. 7, 2012 for Canadian Patent Application No. 2,740,358 filed Oct. 12, 2009.
European Search Opinion and Supplementary European Search Report for Application No. EP2009820037.1, mailed on Aug. 14, 2012.
U.S. Appl. No. 61/646,348.
Further Processing Decision for Application No. EP2009820037.1, mailed on Jul. 16, 2013.
Office Action mailed Jul. 12, 2013 for U.S. Appl. No. 13/219,683, filed Aug. 28, 2011.
Office Action mailed Nov. 12, 2013 for U.S. Appl. No. 13/219,683, filed Aug. 28, 2011.
Office Action mailed Jul. 1, 2013 for U.S. Appl. No. 13/218,145, filed Aug. 25, 2011.
Office Action mailed Oct. 18, 2013 for U.S. Appl. No. 13/218,145, filed Aug. 25, 2011.
Office Action mailed May 6, 2013 for U.S. Appl. No. 13/221,890, filed Aug. 30, 2011.
Office Action mailed Aug. 22, 2013 for U.S. Appl. No. 13/221,890, filed Aug. 30, 2011.
Office Action mailed Aug. 14, 2013 for U.S. Appl. No. 13/423,413, filed Mar. 19, 2012.
Office Action mailed Jul. 22, 2013 for U.S. Appl. No. 13/451,468, filed Apr. 19, 2012.
Co-pending U.S. Appl. No. 13/832,575, filed Mar. 15, 2013.
Office Action mailed Apr. 17, 2013 for U.S. Appl. No. 13/442,850, filed Apr. 9, 2012 (including PTO-892).
Office Action mailed Sep. 9, 2013 for U.S. Appl. No. 13/442,850, filed Apr. 9, 2012 (including PTO-892).
Office Action mailed Jan. 30, 2013 for Canadian Patent Application No. 2,737,322 filed Apr. 14, 2011.
Office Action mailed Oct. 3, 2013 for Canadian Patent Application No. 2,737,322 filed Apr. 14, 2011.
Office Action mailed Sep. 4, 2013 for Chinese Patent Application No. 200980152835.6 field Oct. 12, 2009 (with translation).
Examiner Interview Summary mailed Dec. 16, 2013 for U.S. Appl. No. 13/221,890.
Examiner Interview Summary mailed Jan. 8, 2014 for U.S. Appl. No. 13/219,683.
Notice of Allowance mailed Jan. 7, 2014 for U.S. Appl. No. 13/218,145, filed Aug. 25, 2011.
Notice of Allowance mailed Jan. 6, 2014 for U.S. Appl. No. 13/221,890, filed Aug. 30, 2011.
Notice of Allowance mailed Jan. 9, 2014 for U.S. Appl. No. 13/423,413, filed Mar. 19, 2012.
Notice of Allowance mailed Dec. 24, 2013 for U.S. Appl. No. 13/072,656, filed Mar. 25, 2011.

* cited by examiner

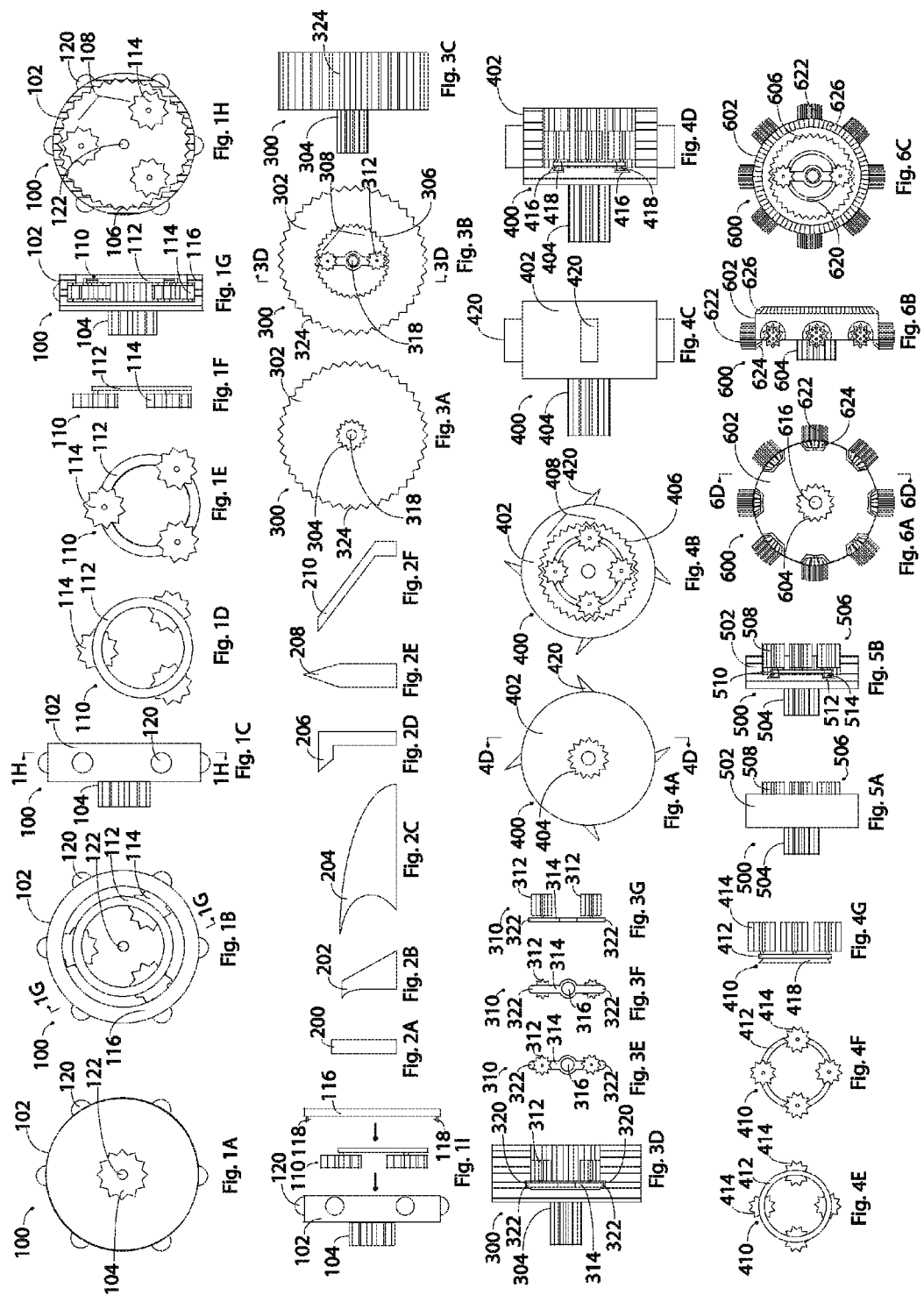

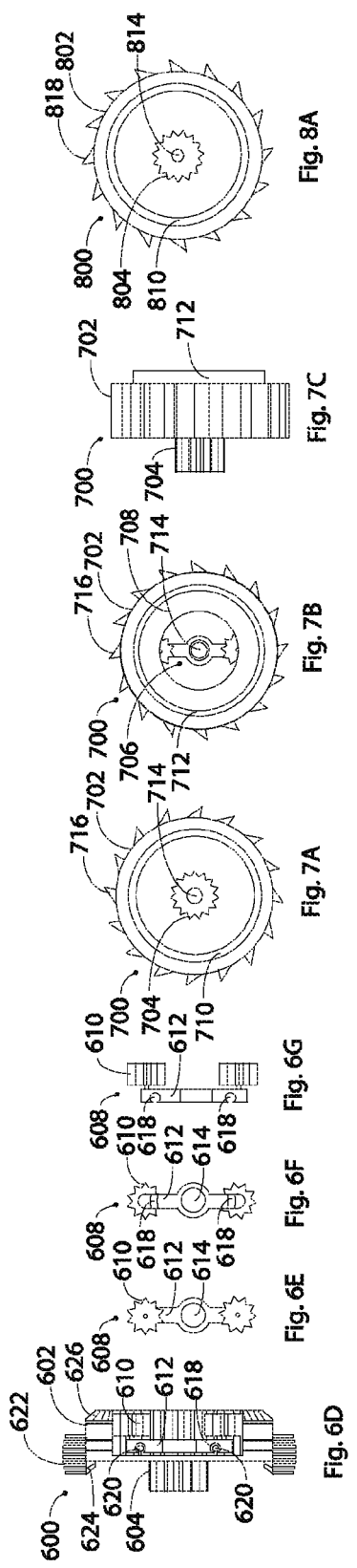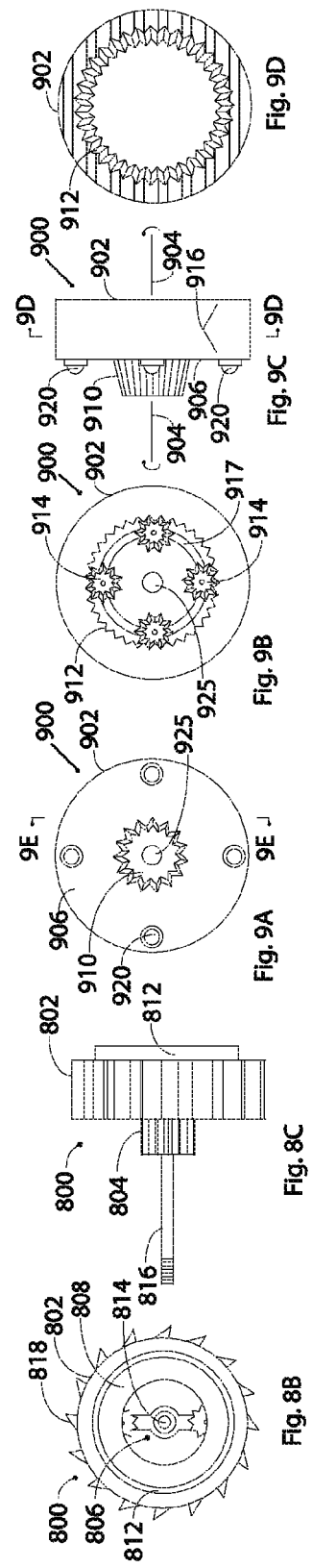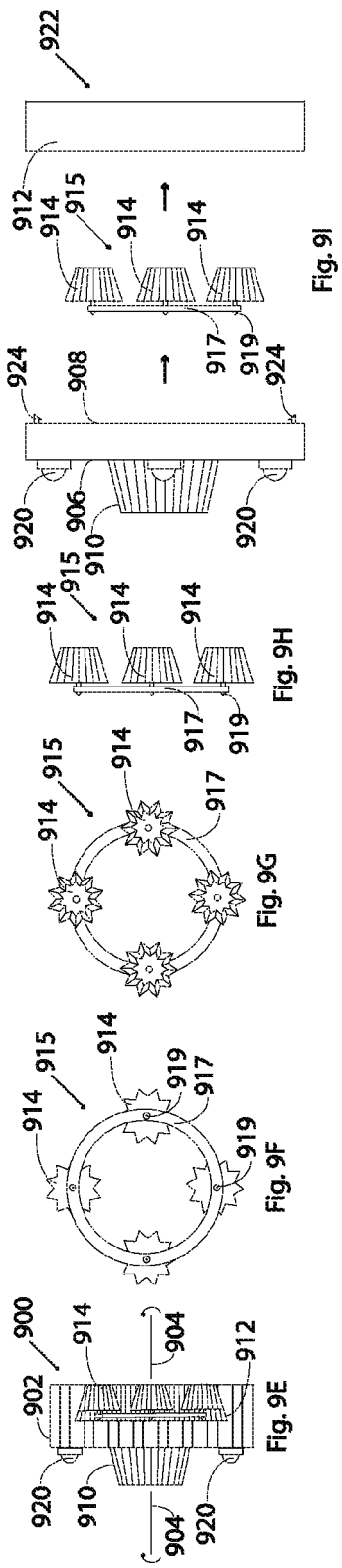

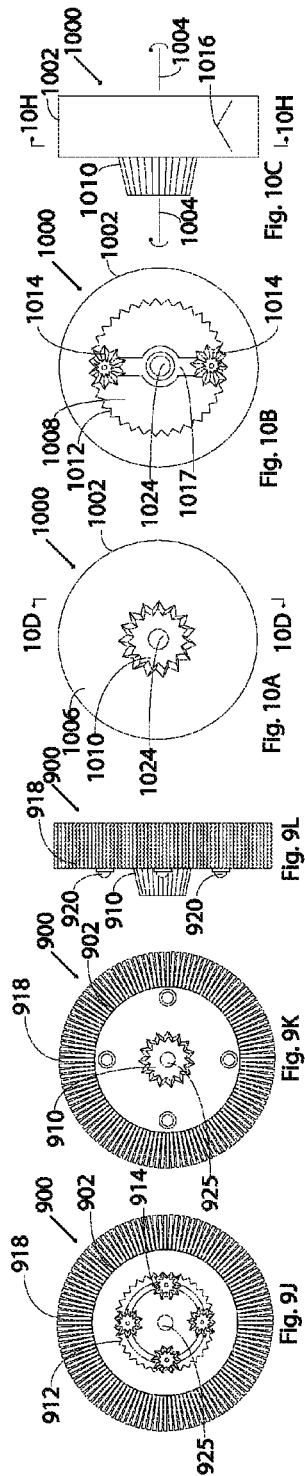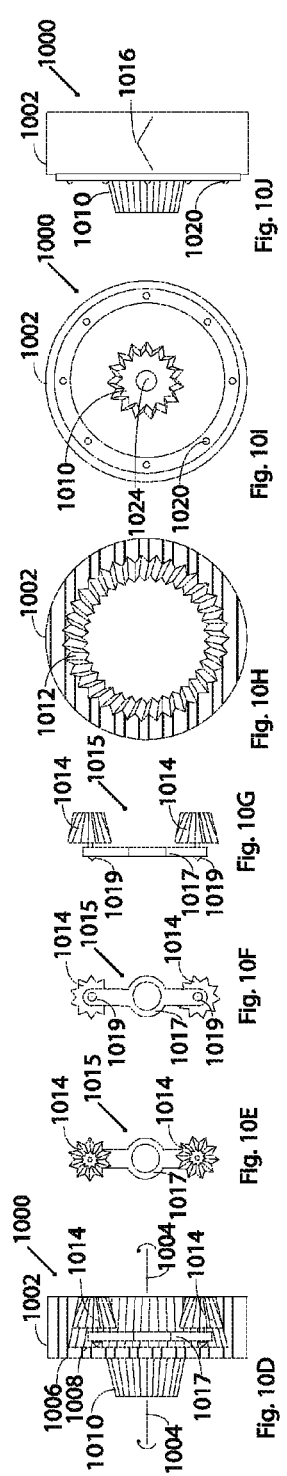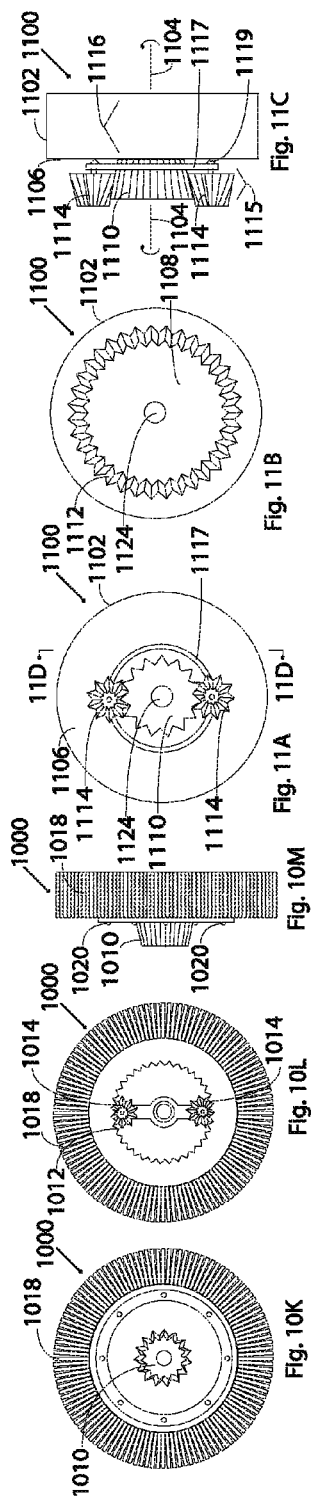

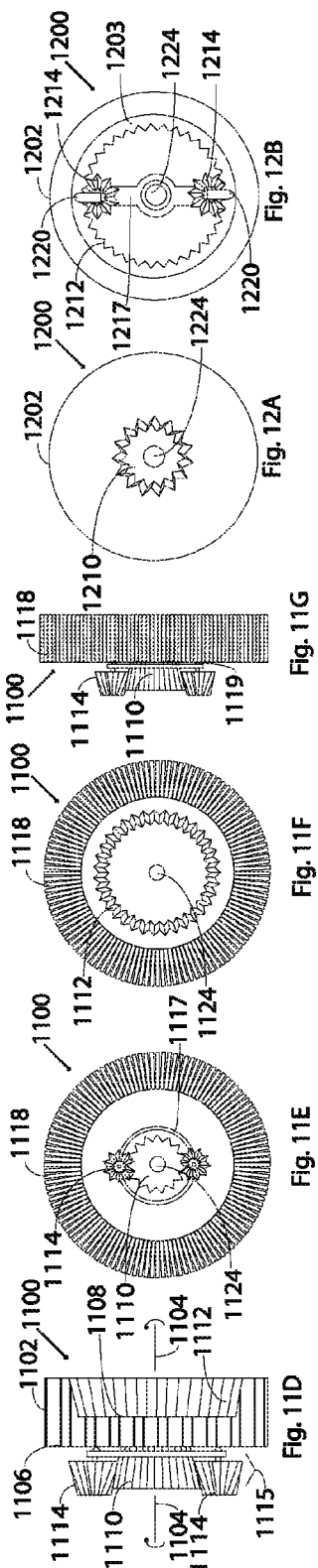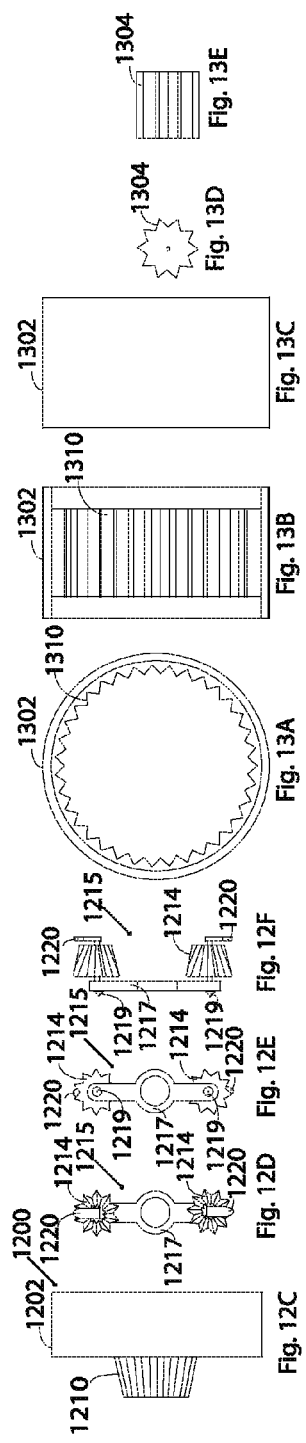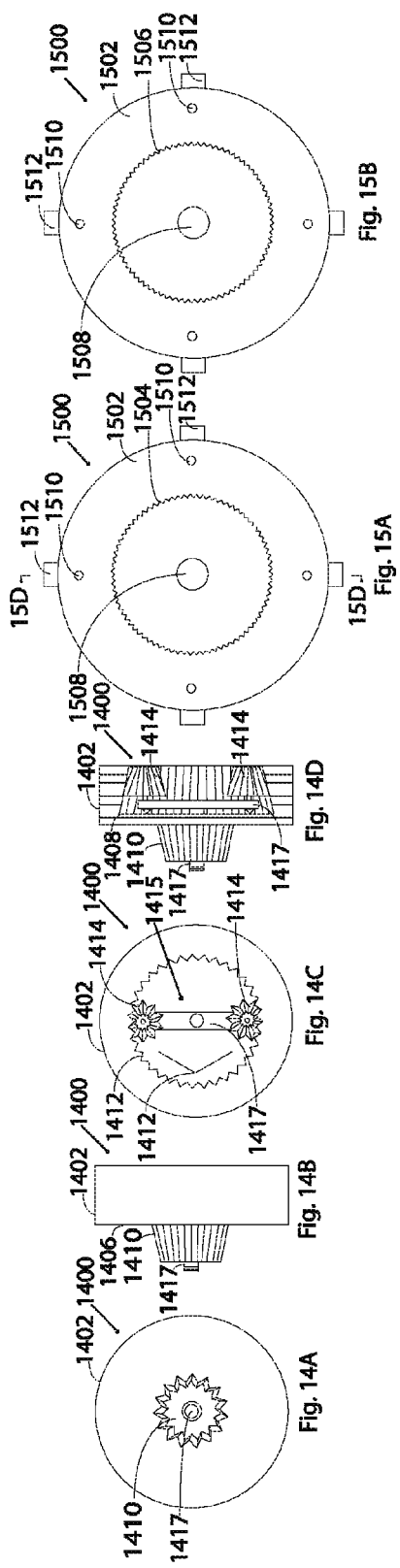

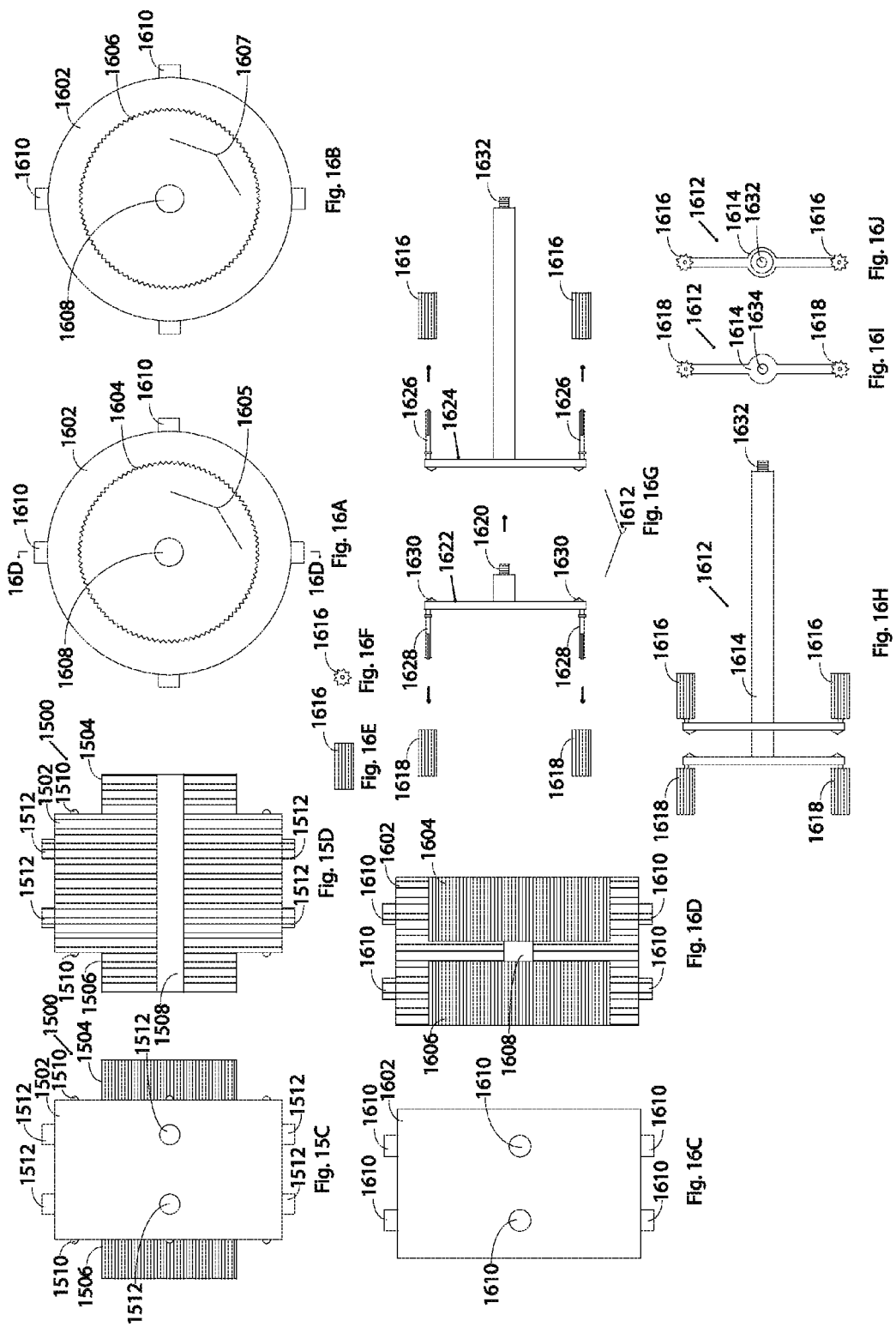

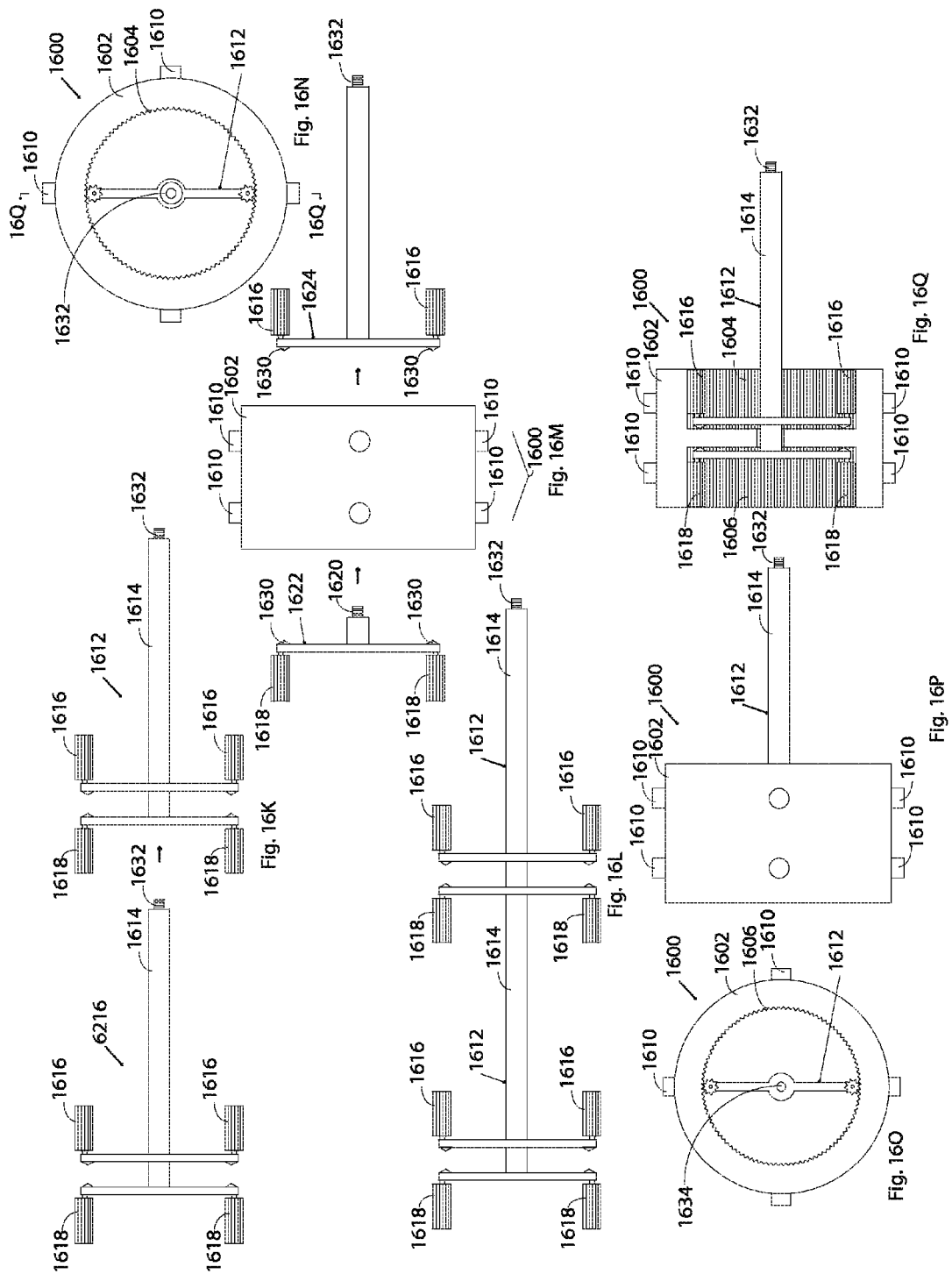

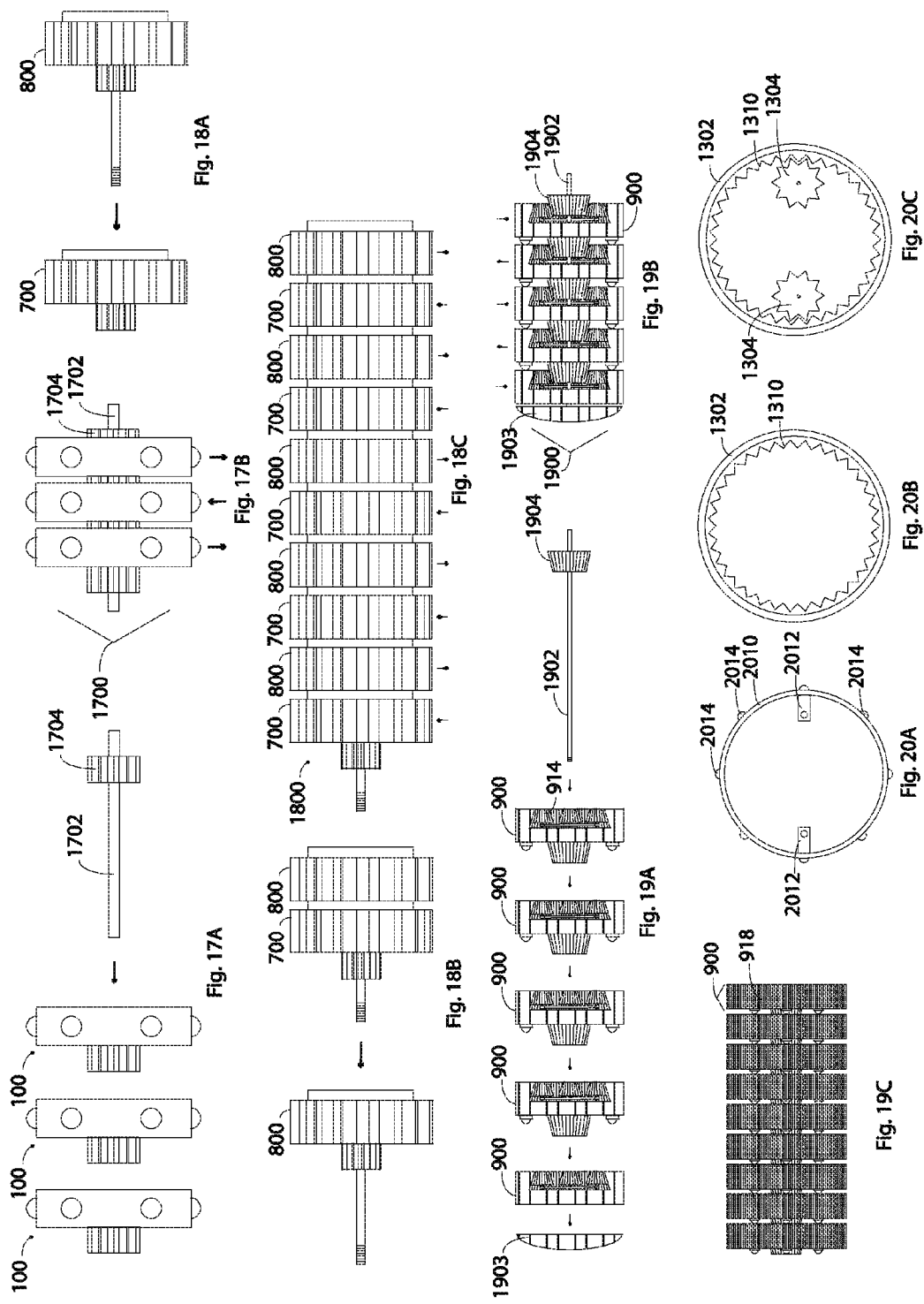

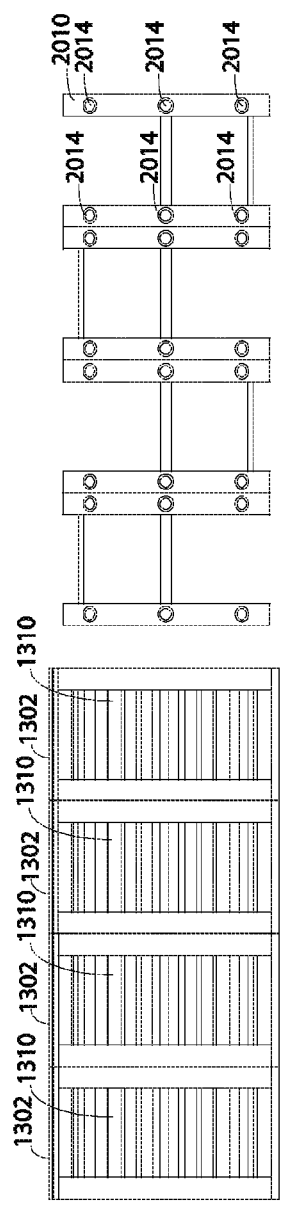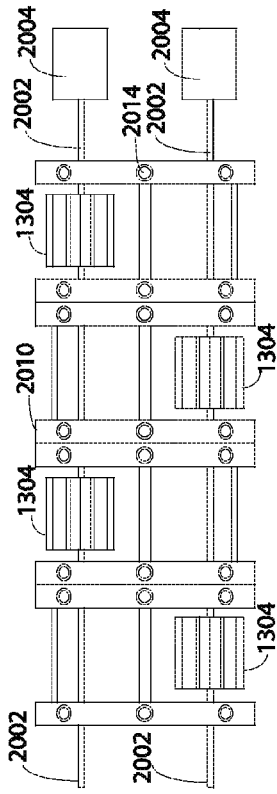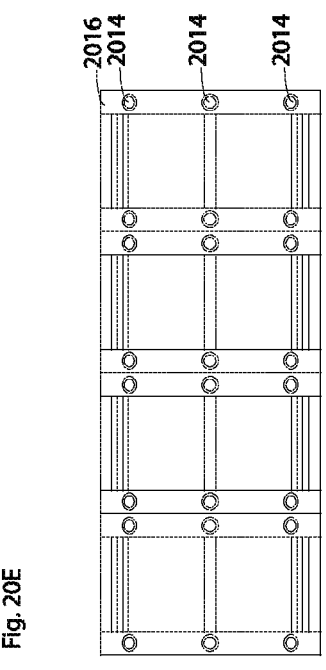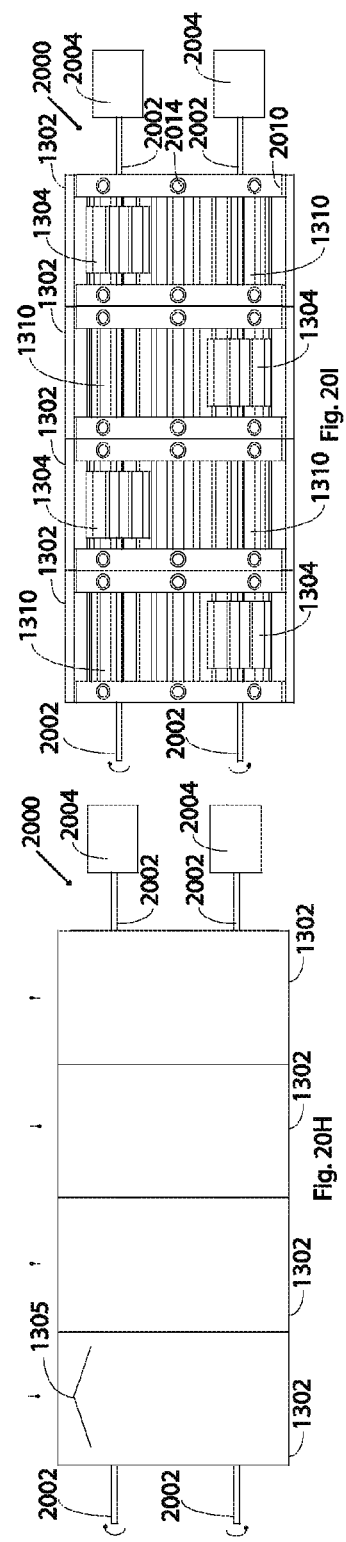

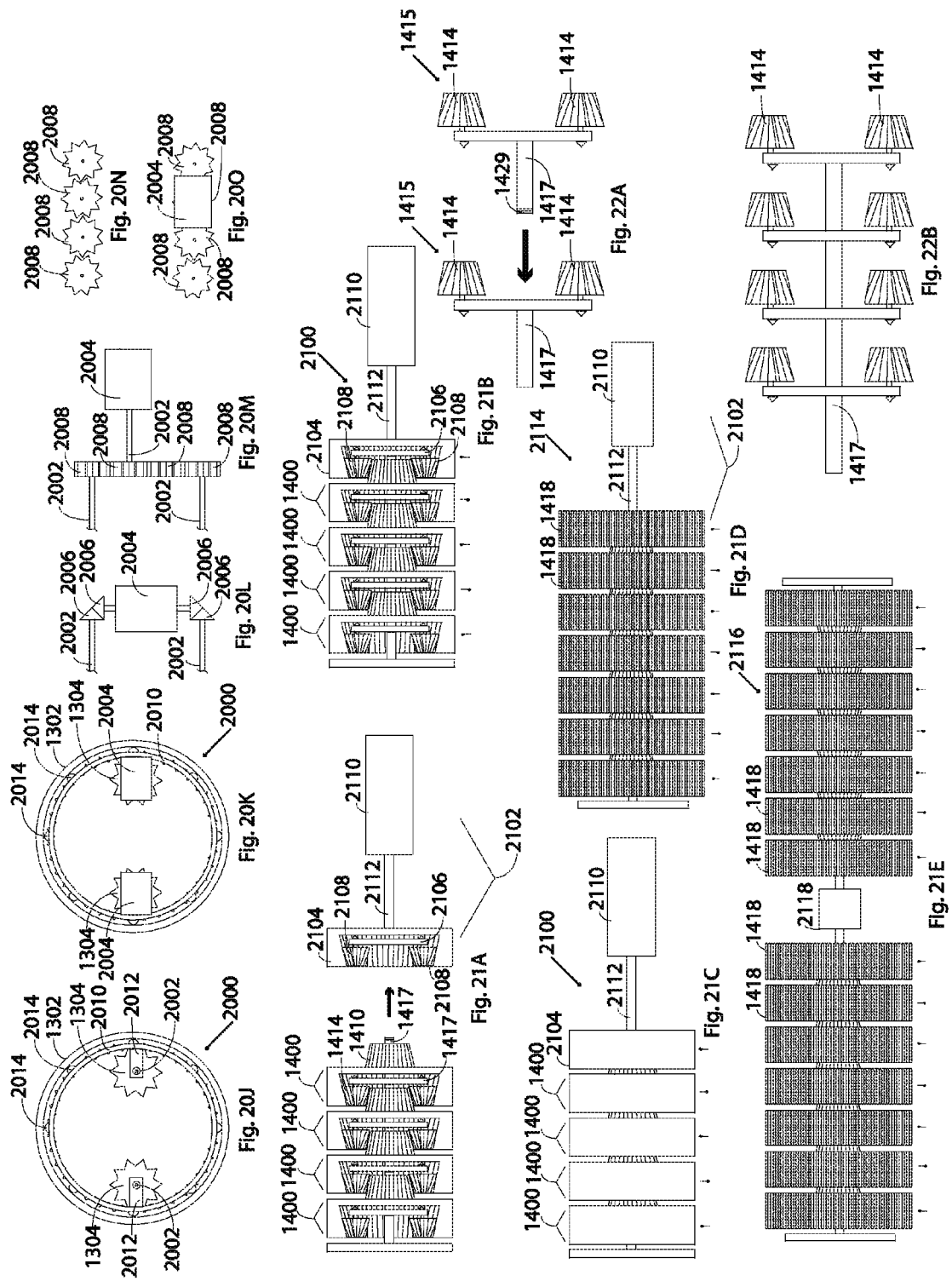

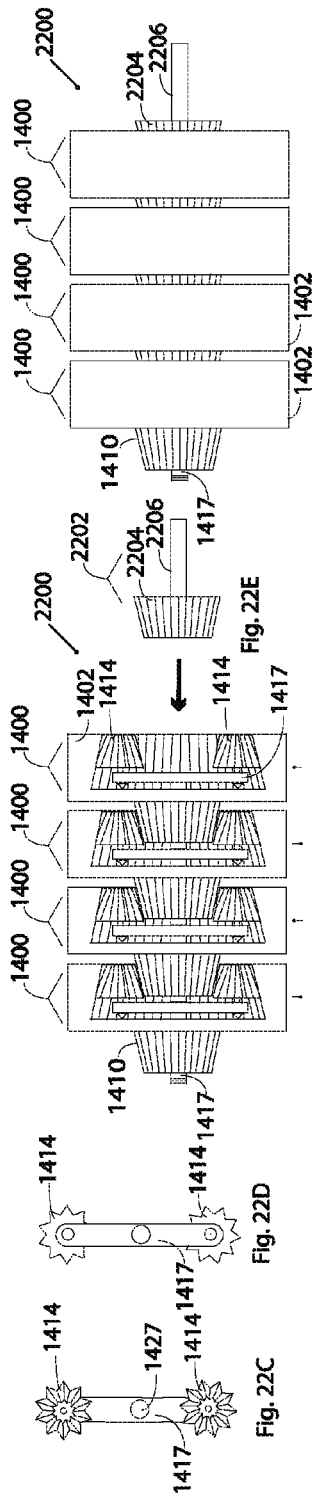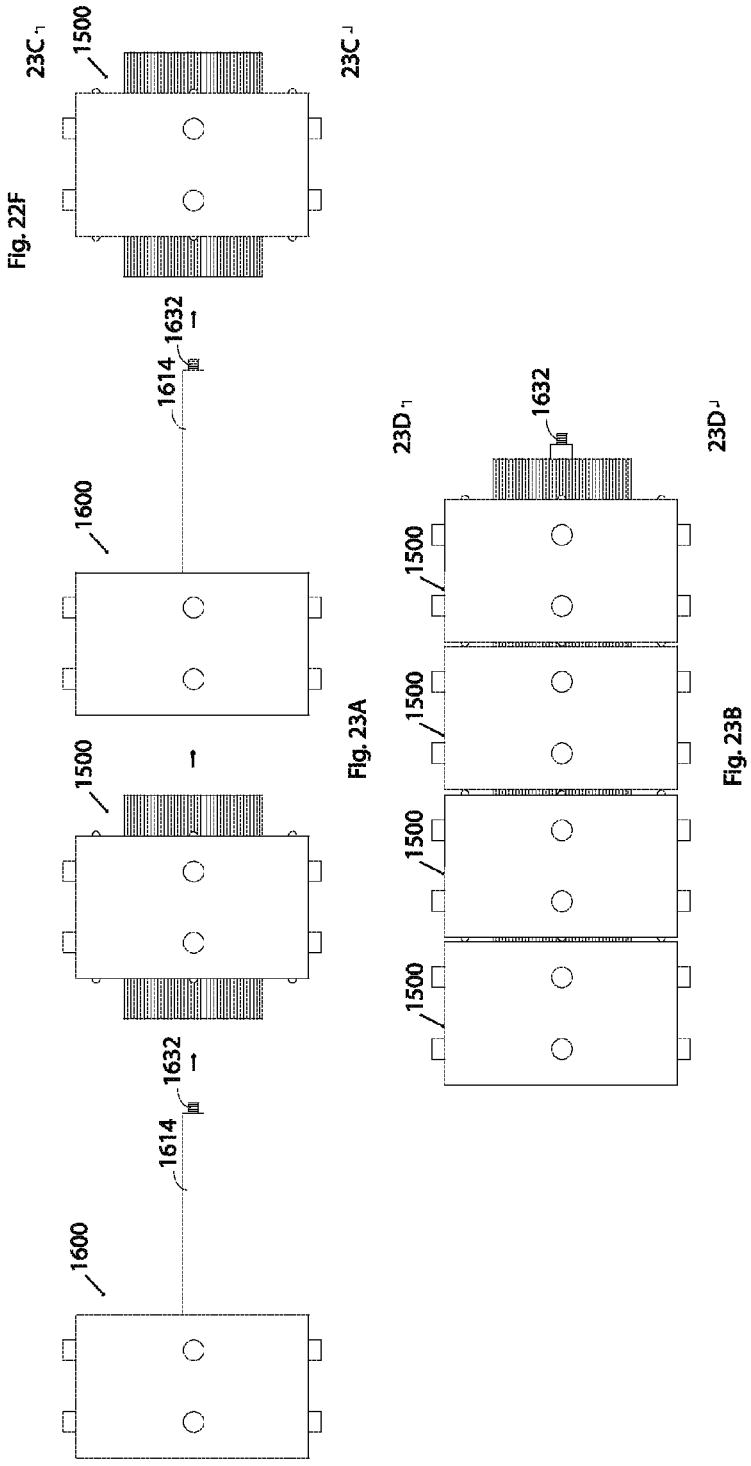

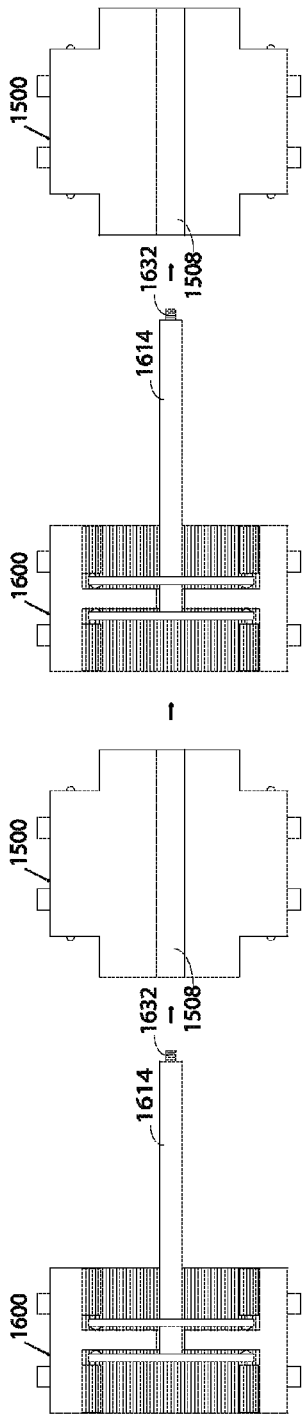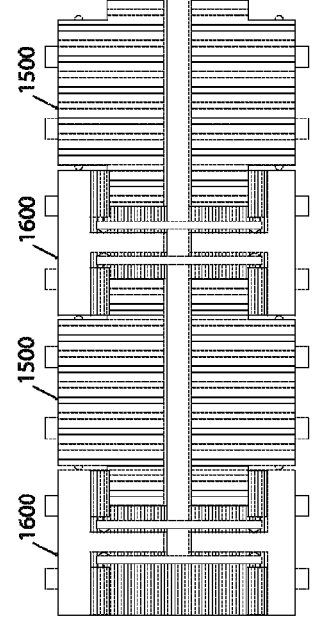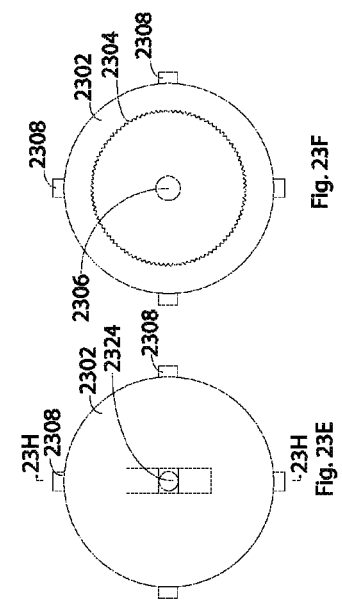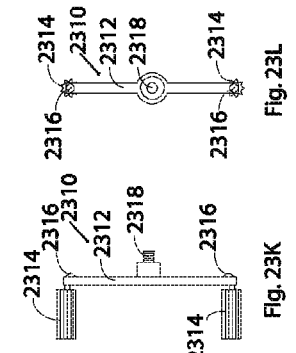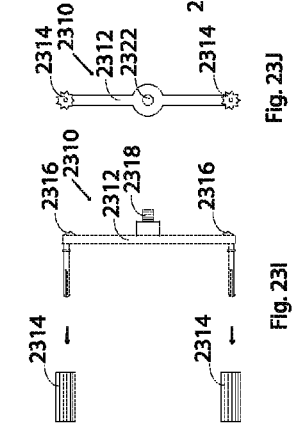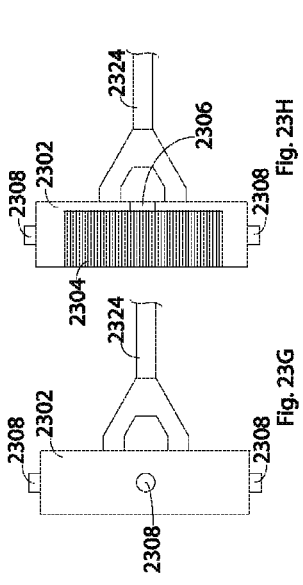

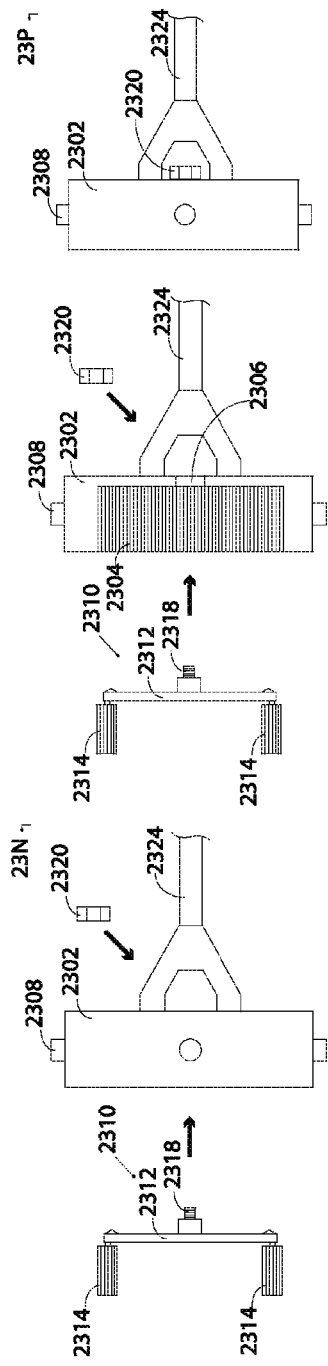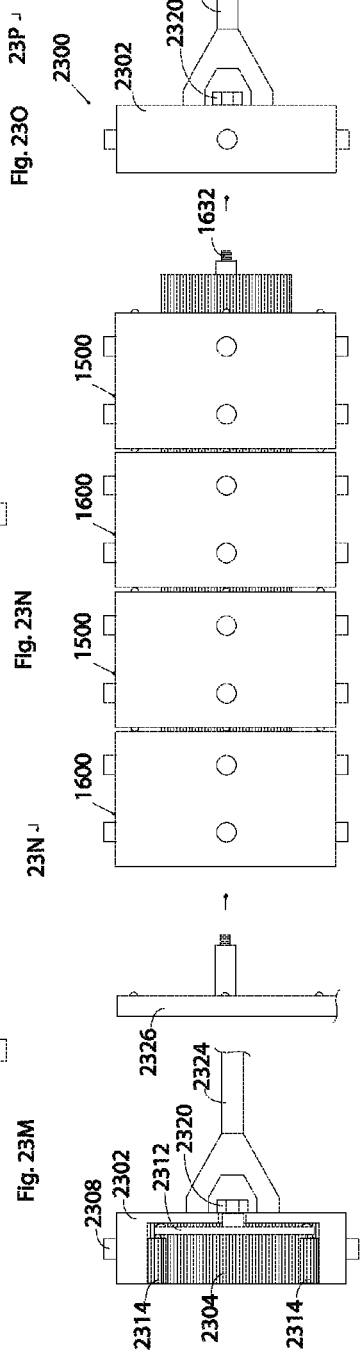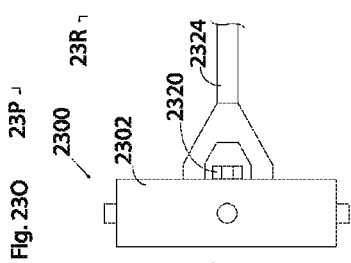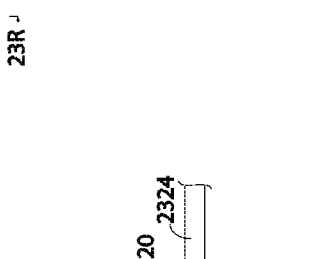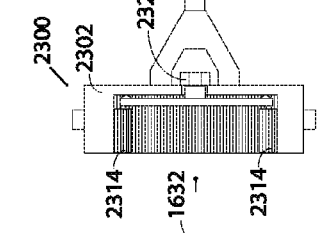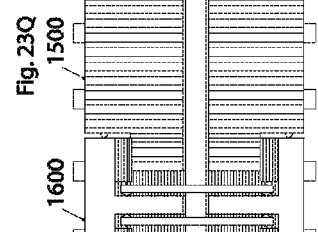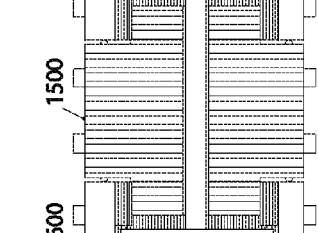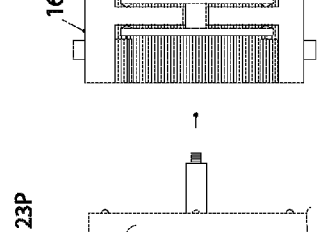

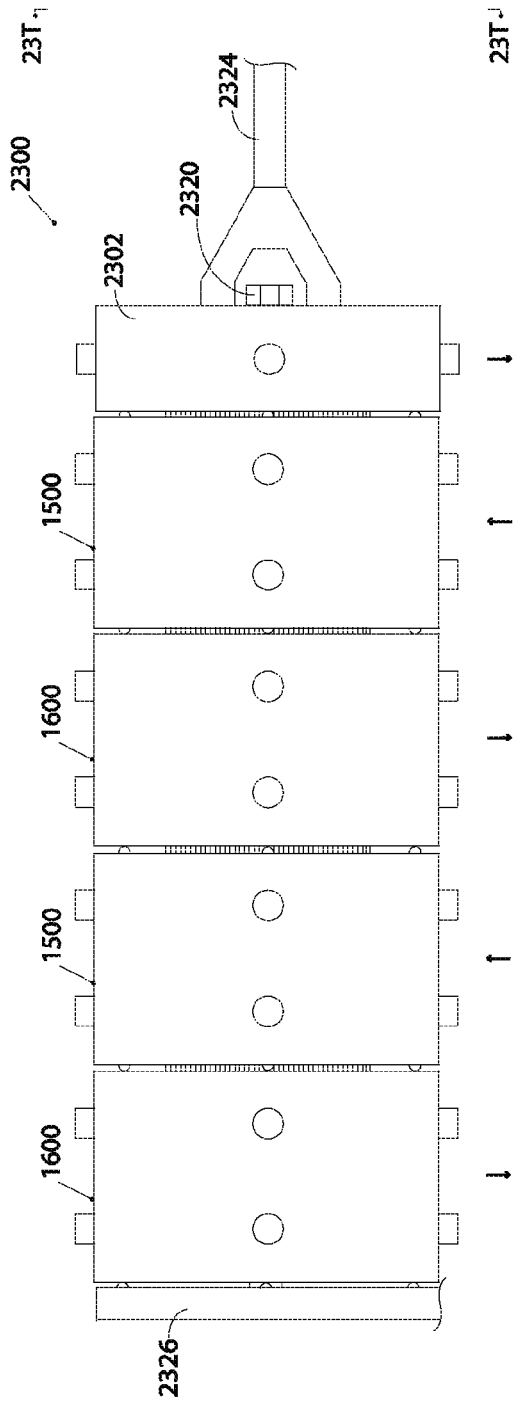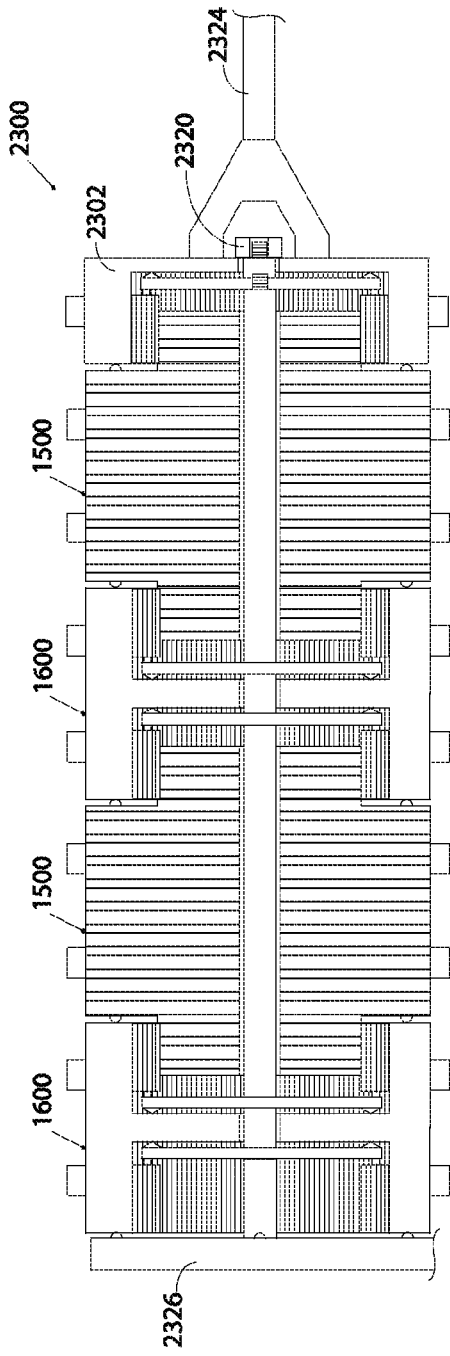

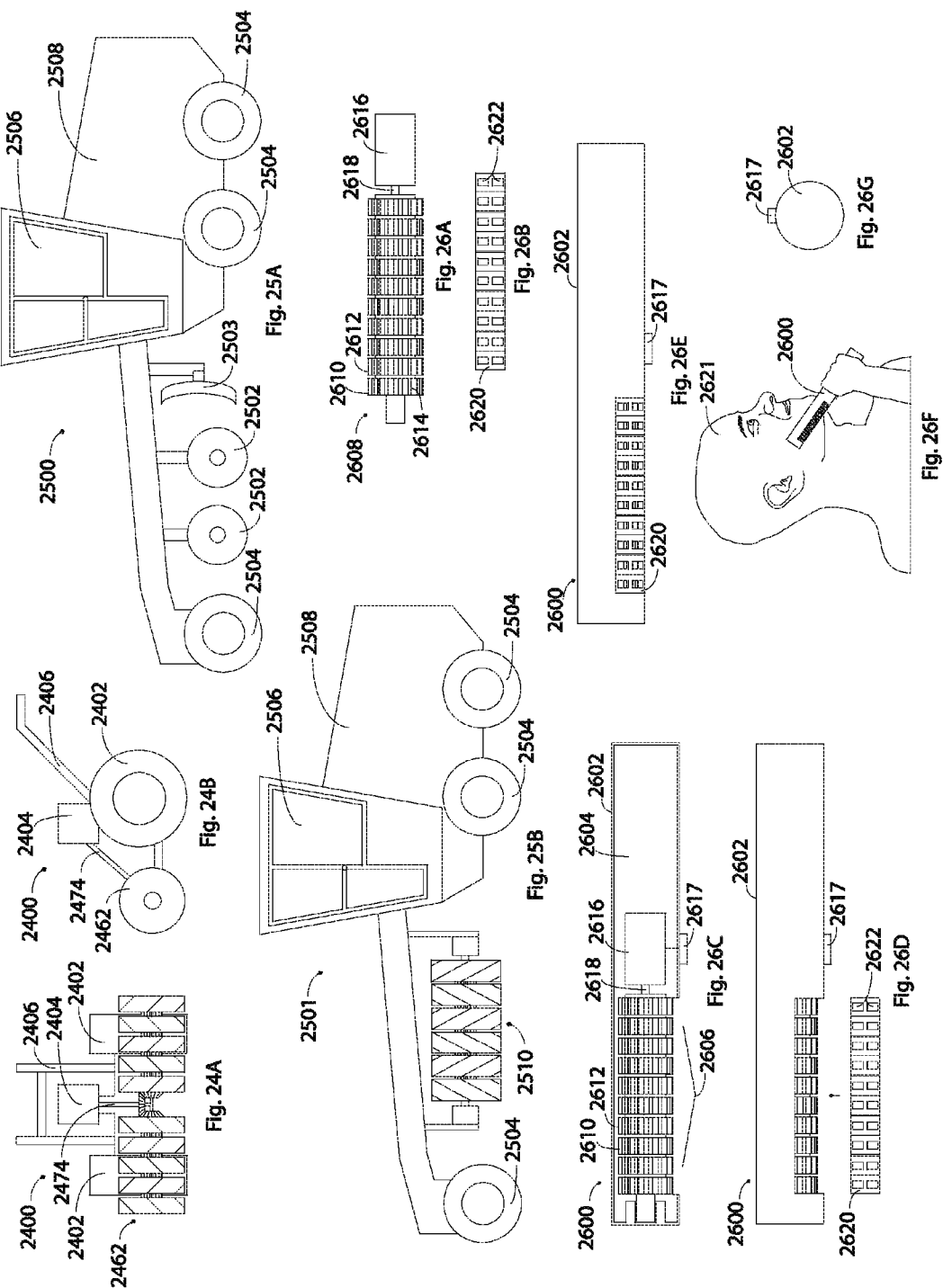

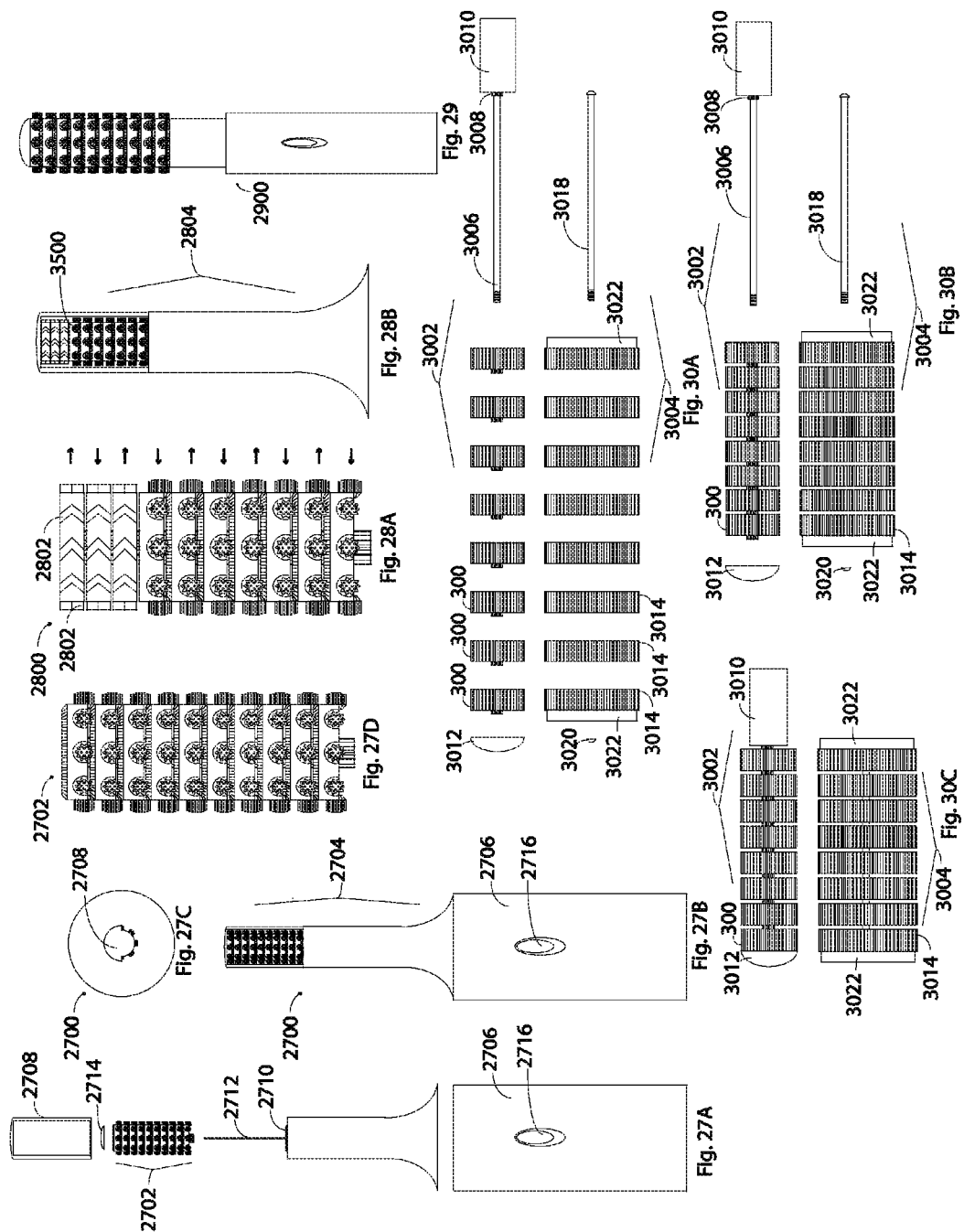

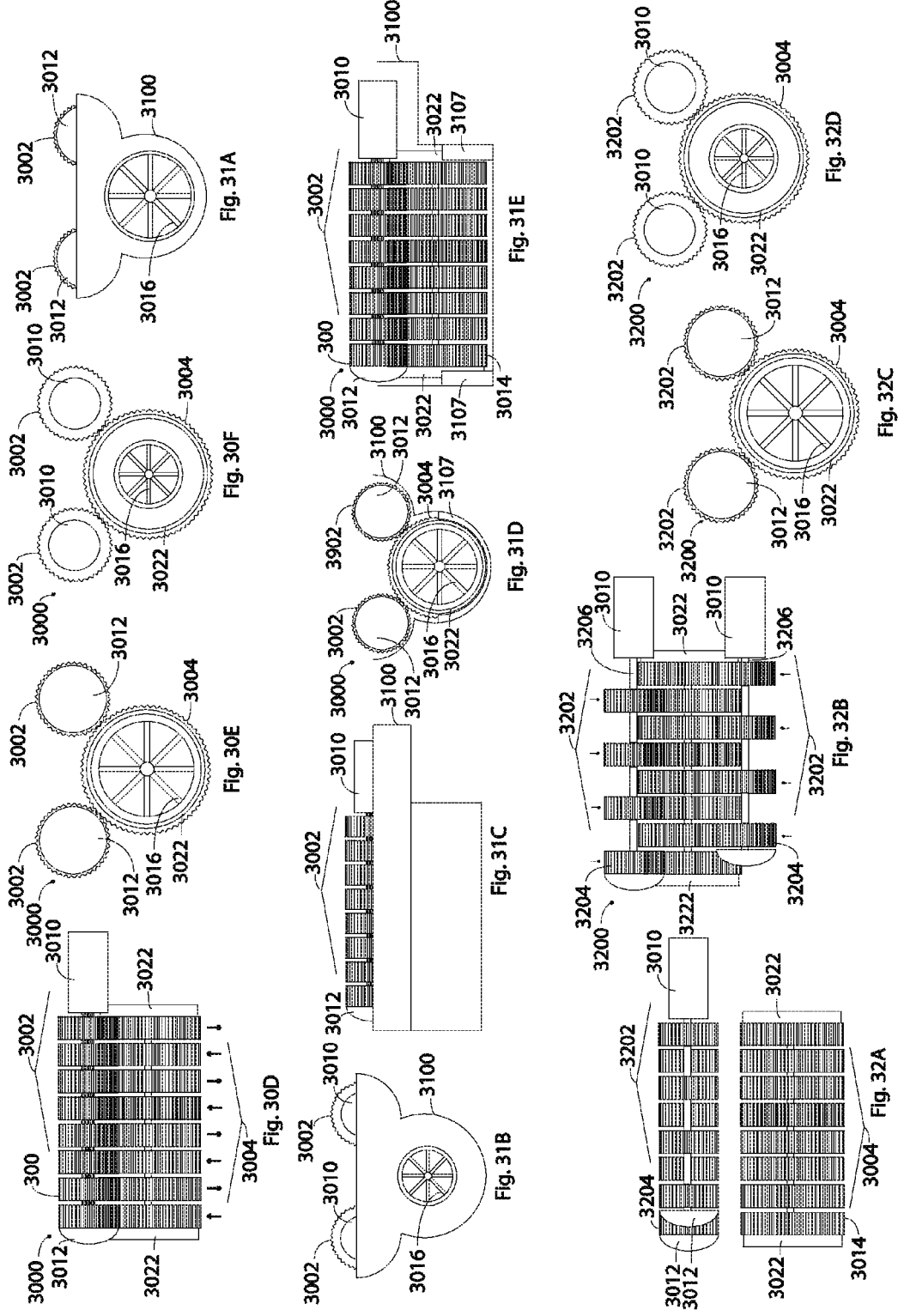

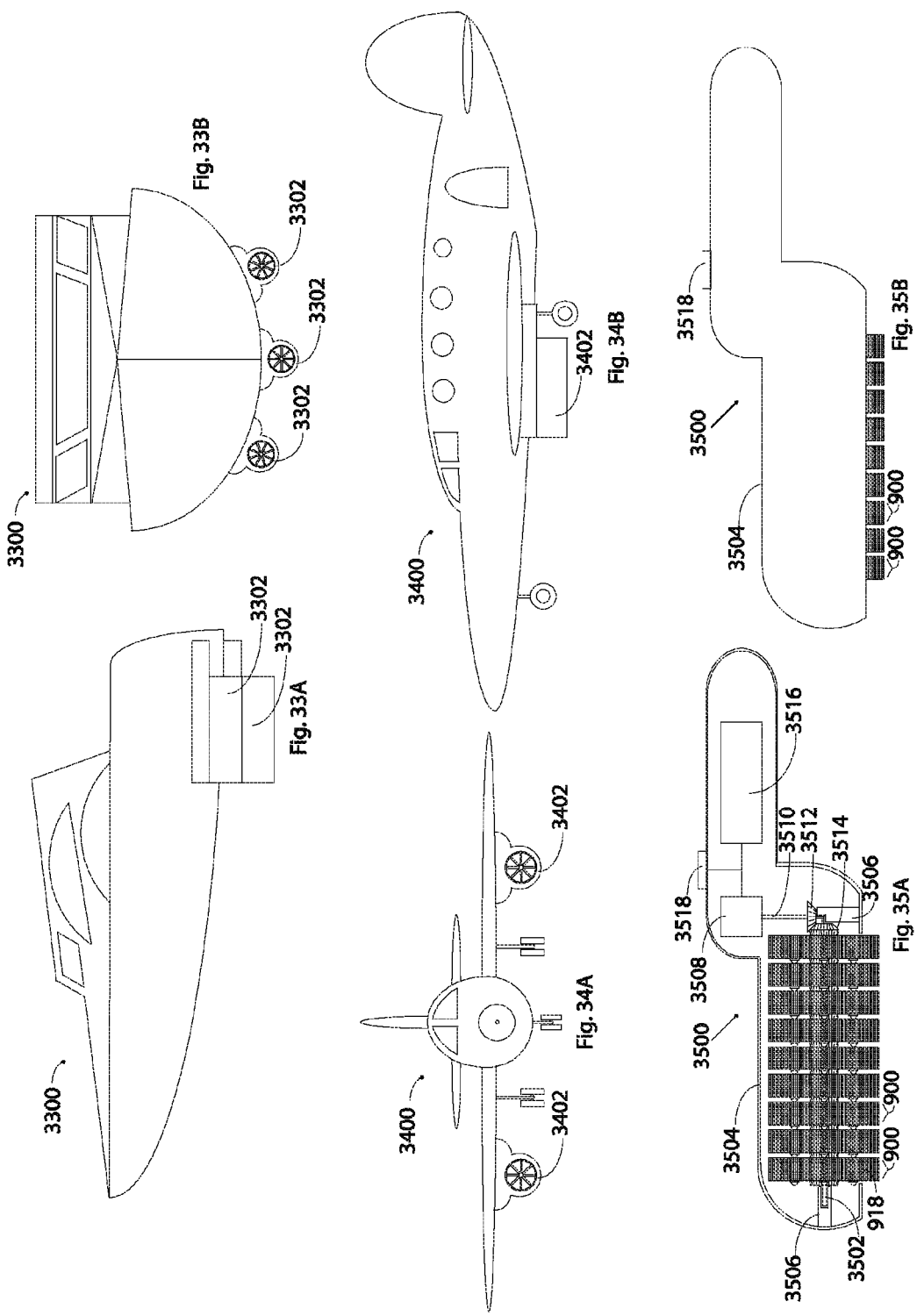

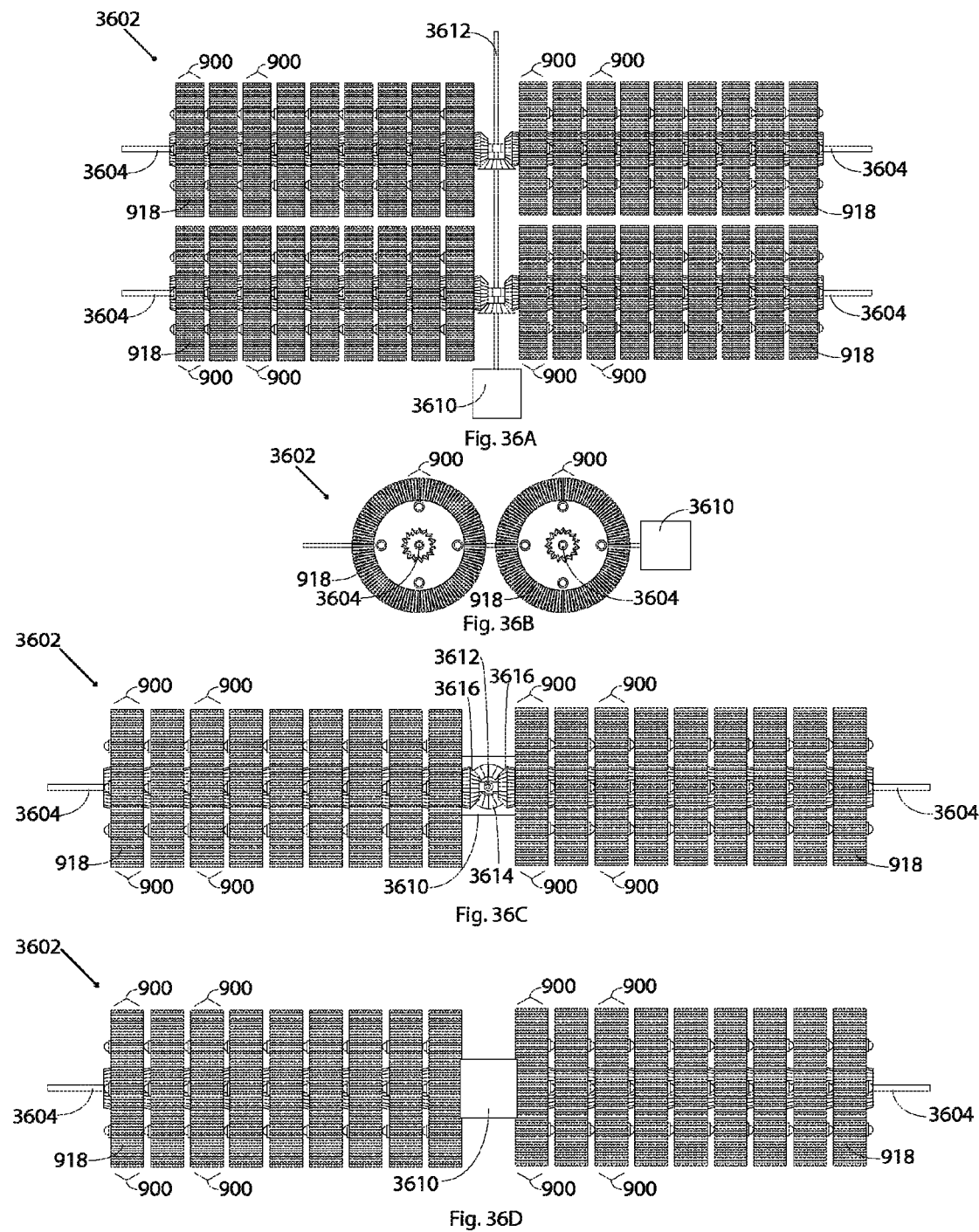

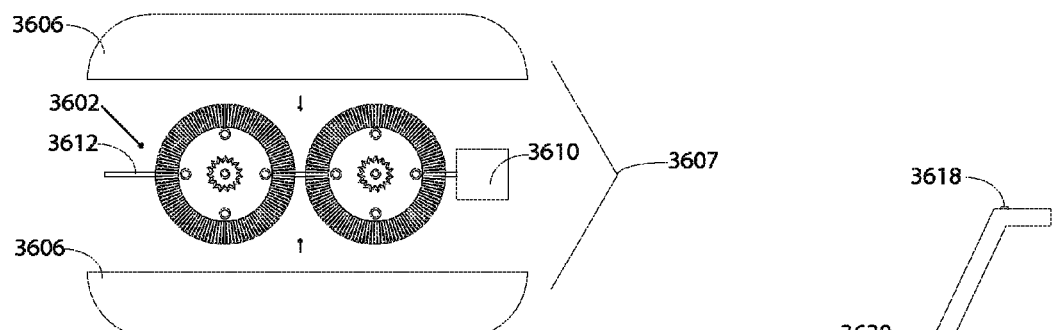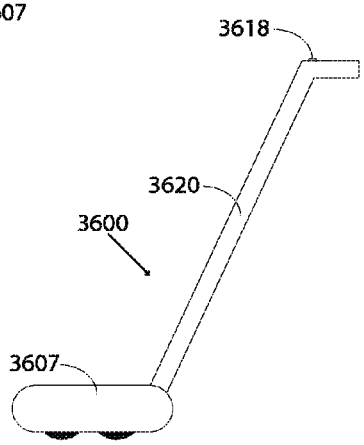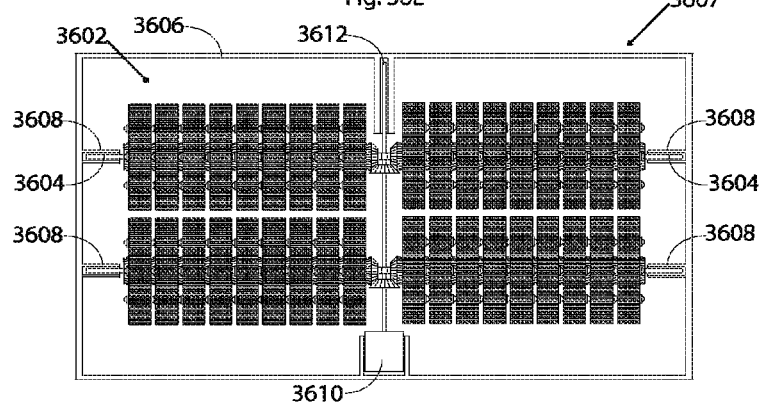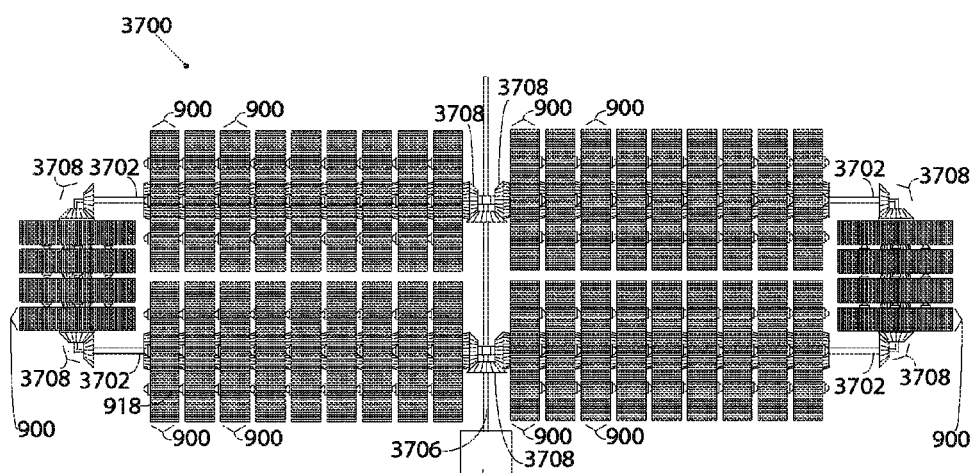

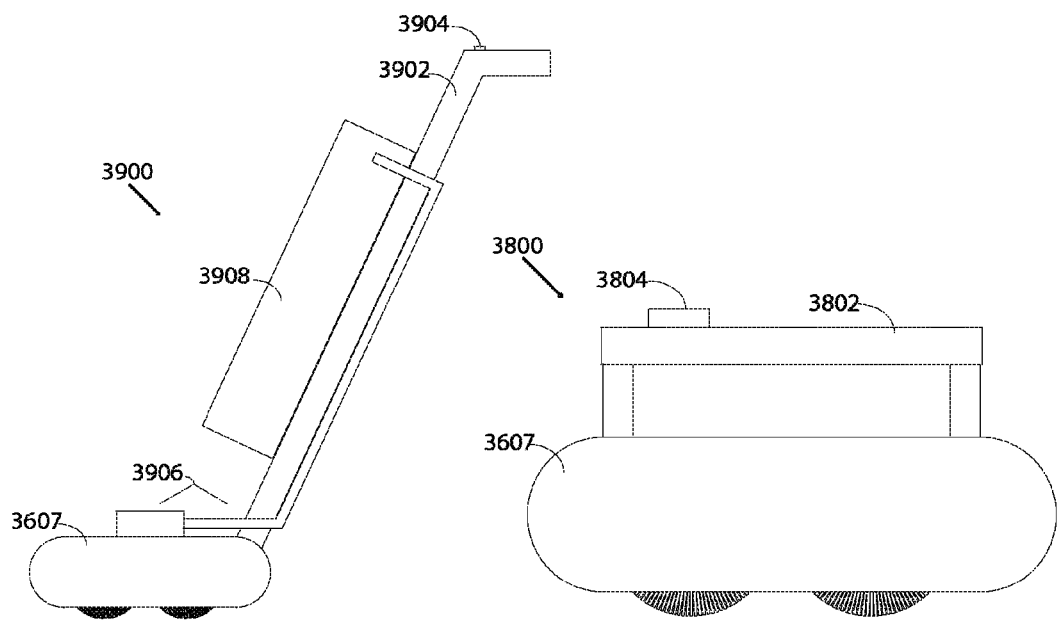
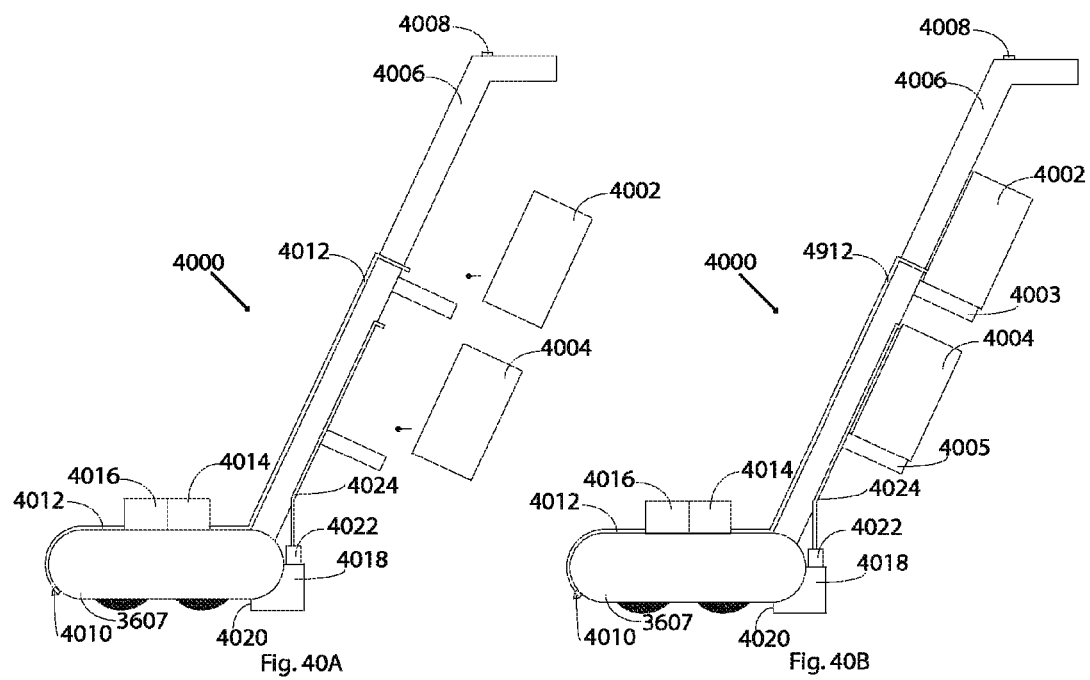

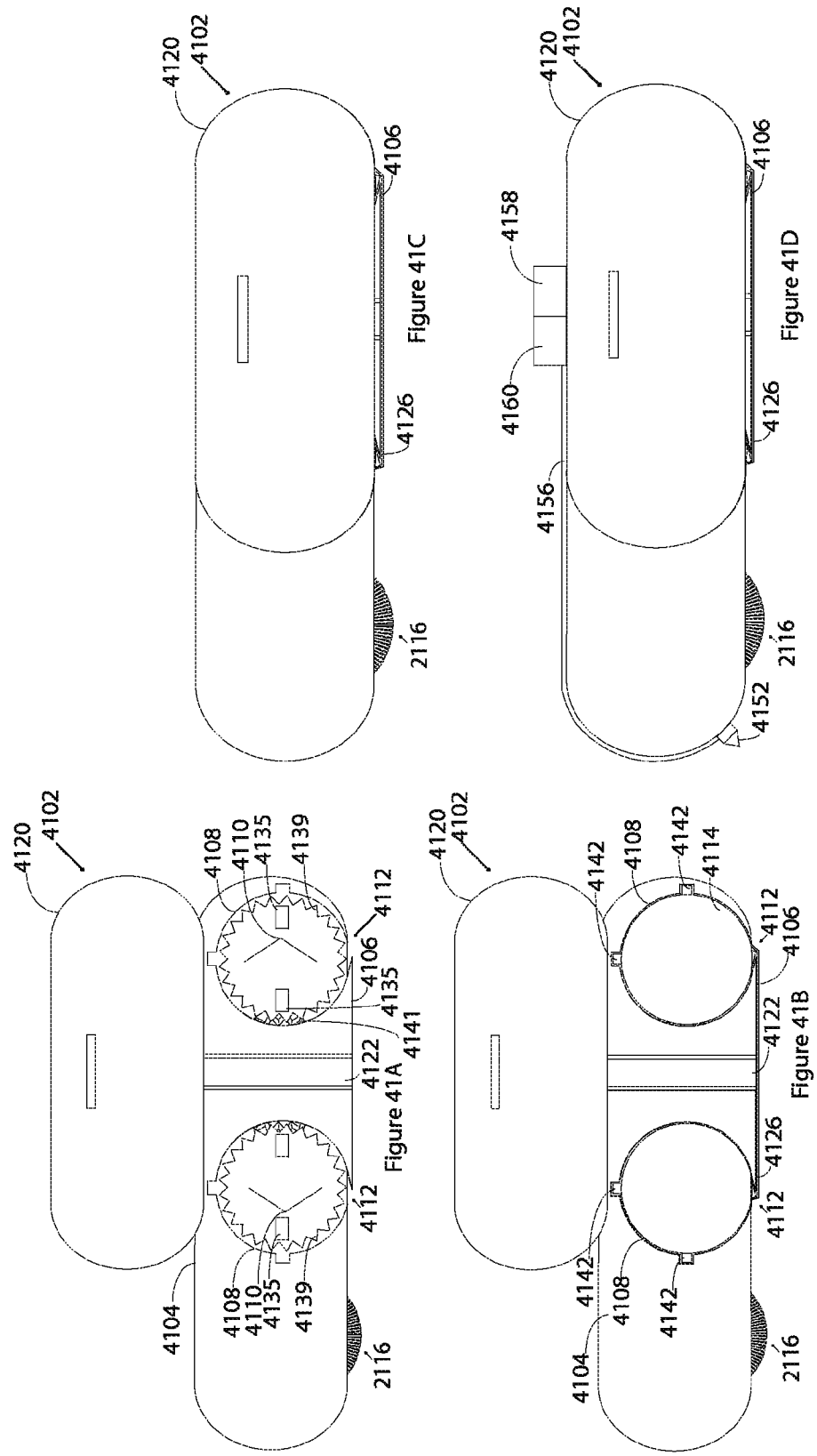

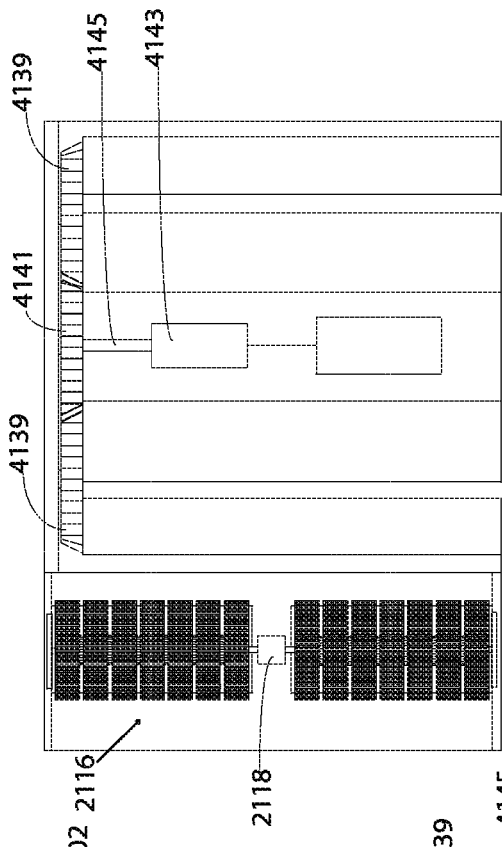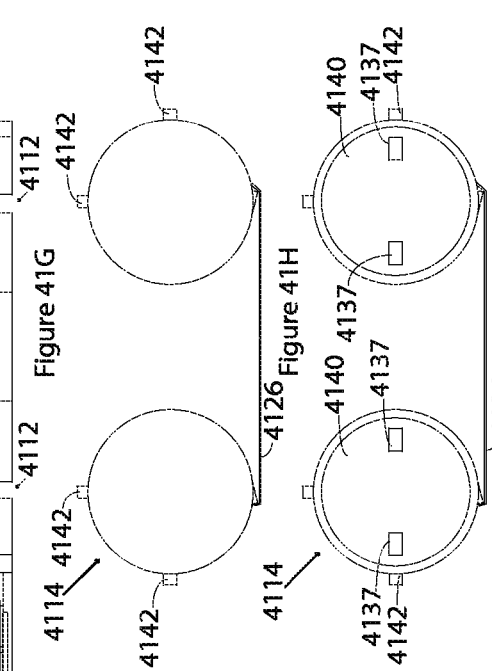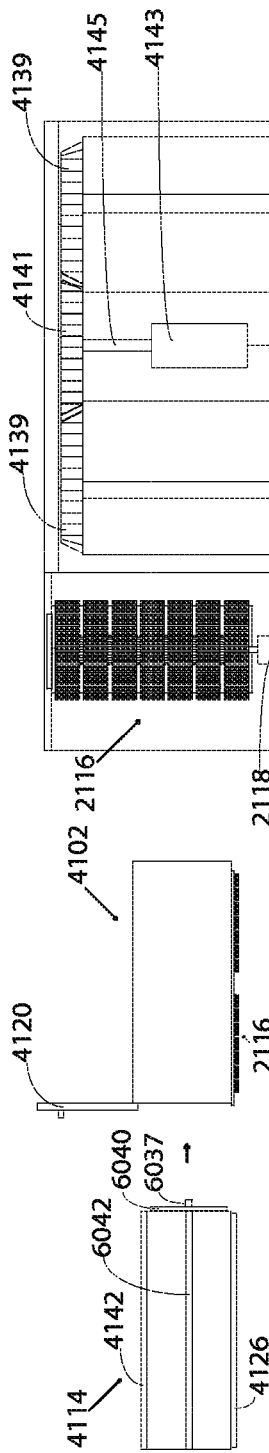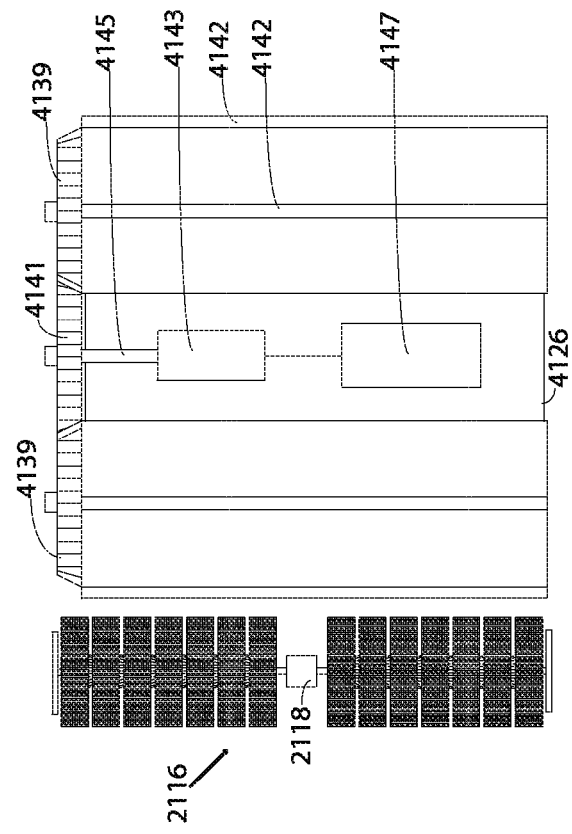

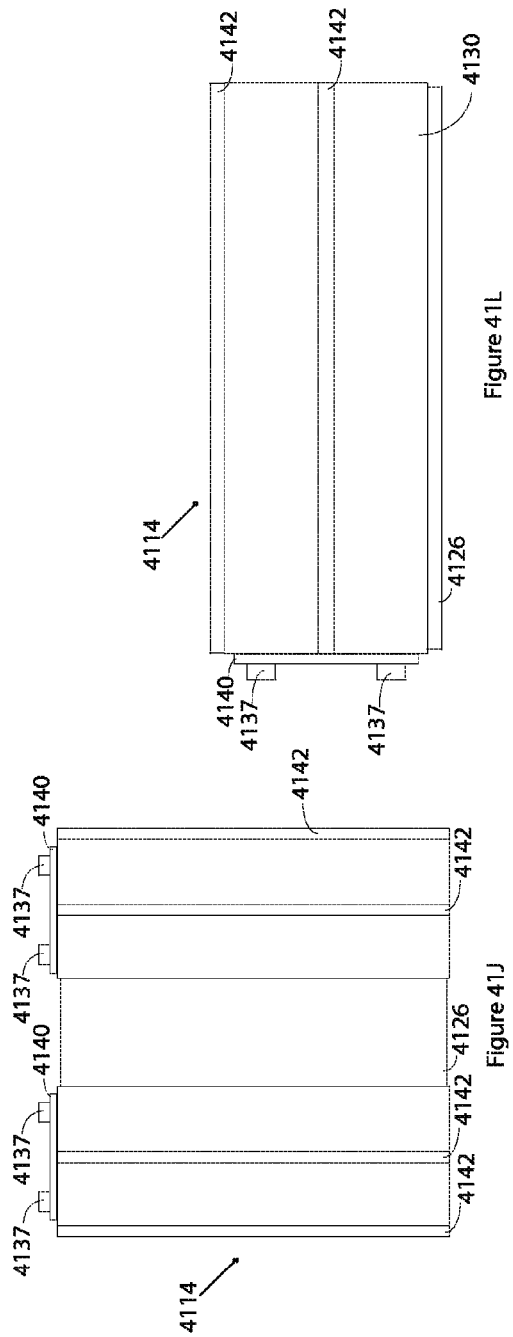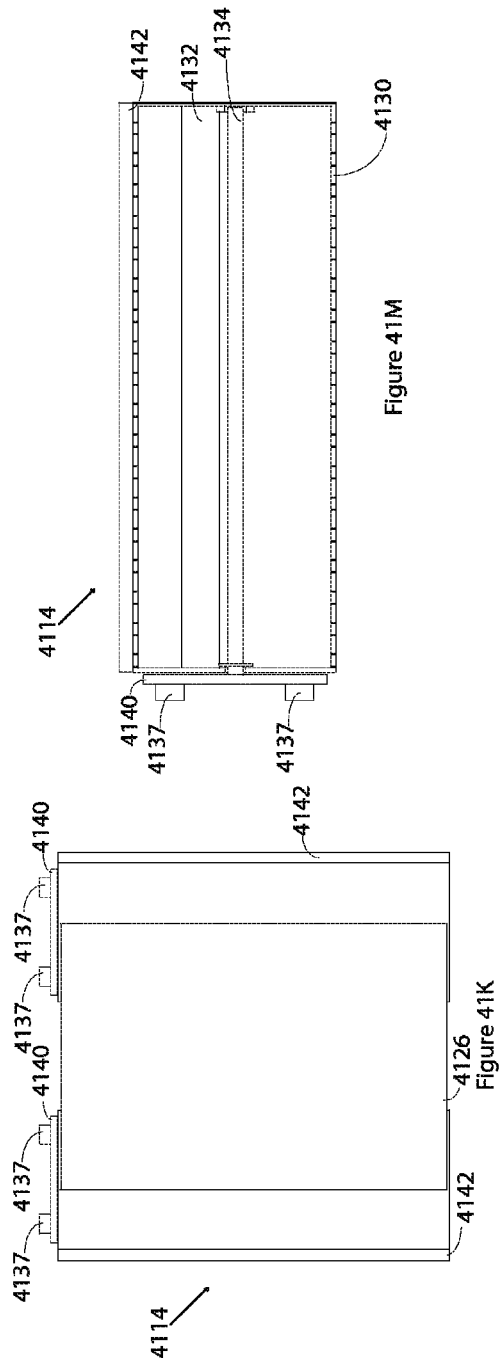

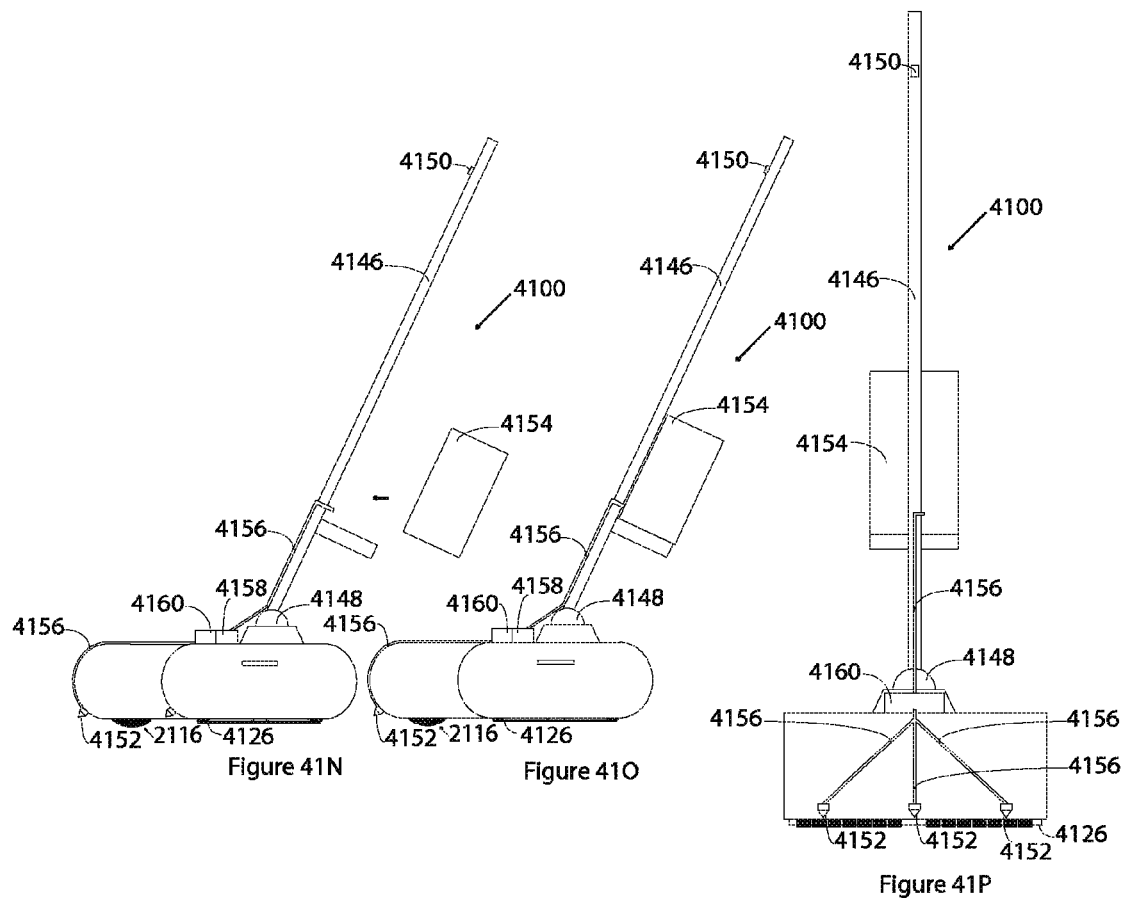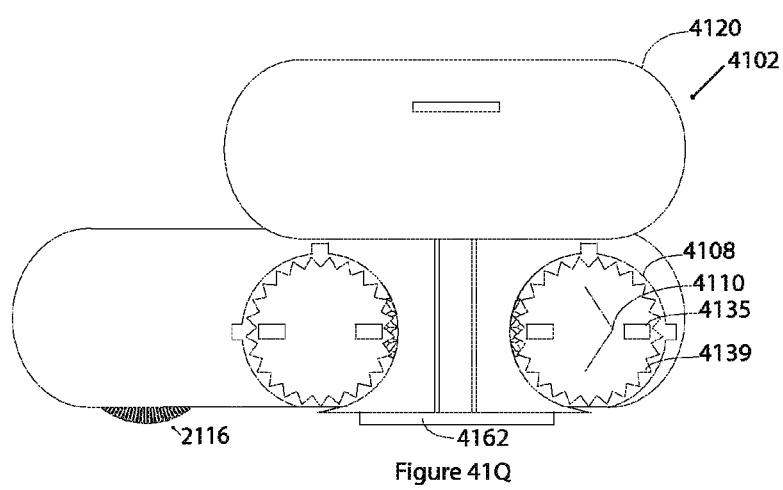

ROTARY UNITS, ROTARY MECHANISMS, AND RELATED APPLICATIONS

CROSS-REFERENCE TO RELATED APPLICATIONS

This application is a continuation-in-part of, and claims the benefit of priority from, U.S. Non-Provisional patent application Ser. No. 12/577,326, filed Oct. 12, 2009, which claims the benefit of priority from U.S. Provisional Patent Application No. 61/104,748, filed on Oct. 12, 2008 and International Patent Application No. PCT/US09/60386, filed on Oct. 12, 2009, which are each incorporated by reference in their entirety. This application also claims the benefit of priority from U.S. Provisional Patent Application Nos. 61/365,290, filed Jul. 16, 2010 and 61/376,725, filed Aug. 25, 2010, which are each incorporated by reference in their entirety.

FIELD OF THE INVENTION

The invention relates generally to mechanical, electrical, or electromechanical devices, and provides rotary units, rotary mechanisms, methods, and related devices and other applications that are useful for a wide variety of purposes.

BACKGROUND OF THE INVENTION

Electromechanical devices are ubiquitous. Some of these devices include rotating components and are used in many different applications. Gardening tools such as rotor tillers, for example, typically include rotating rotors having tines, which contact the soil during operation. Many other devices of use in agricultural and construction, among many other fields or applications also utilize various types of rotational components to achieve desired forms of work.

SUMMARY OF THE INVENTION

The invention relates to rotary units and rotary mechanisms that are suitable for use in numerous applications. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate. These and many other aspects will be apparent upon a complete review of this disclosure.

In one aspect, the invention provides a rotary unit that includes at least one rotational component comprising at least a first gear component, at least one gear structure receiving area that is configured to receive one or more gear structures or components thereof, and at least a second gear component disposed at least proximal to the gear structure receiving area. The rotary unit also includes at least one gear structure comprising at least one support component and at least one third gear component rotatably coupled to the support component. The third gear component is configured to operably engage the second gear component when the gear structure is at least partially disposed in the gear structure receiving area. In addition, the first gear component is configured to operably engage one or more third gear components of at least one other rotary unit when the rotary unit is disposed proximal to the other rotary unit. In some embodiments of the rotary units of the invention, the rotational component is configured to receive at least one drive mechanism or a portion thereof. In certain embodiments, the other rotary unit operably engages the rotary unit. To further illustrate, in certain embodiments, at least two other rotary units operably engage the rotary unit.

The rotational components of the rotary units and rotary mechanisms of the invention include various embodiments. In some embodiments, for example, the rotational components are coupled to one another via a shaft positioned proximal to an axis of rotation. In certain embodiments, the rotary units and rotary mechanisms of the invention include more than two rotational components (e.g., 3, 4, 5, 6, 7, 8, 9, 10 or more rotational components) in which neighboring pairs of rotational components are configured to substantially simultaneously counter-rotate relative to one another. In some embodiments, a friction reducing material is disposed between the first and second rotational components to reduce friction between the first and second rotational components when the first and second rotational components substantially coaxially rotate relative to one another. In some embodiments, the rotational components substantially coaxially rotate around a rotational axis that is substantially horizontally disposed during operation of the rotary mechanism. Optionally, the rotational components each comprise one or more alignment components structured to align neighboring pairs of rotational components relative to one another. In some of these embodiments, for example, the alignment components comprise a circular ridge disposed on, extending from, or attached to a surface of a first member of a pair of neighboring rotational components and a circular groove disposed in a surface of a second member of the pair of neighboring rotational components, which circular ridge inserts into and rotates in the circular groove in an assembled rotary mechanism. In certain embodiments, the alignment components comprise a circular groove disposed in a surface of each member of the pair of neighboring rotational components and a ring disposed in the grooves of the pair of neighboring rotational components, which grooves rotate about the ring in an assembled rotary mechanism.

Typically, the rotary units or mechanisms of the invention include one or more implements that can be used or adapted for use in many different applications. In certain embodiments, for example, at least one surface of a rotational component comprises at least one implement. Optionally, a rotational component comprises at least one implement that is configured to effect the movement of one or more other components (e.g., a propeller component or the like) when the rotational component rotates and the implement operably engages the other components. In certain embodiments, rotary units or mechanisms include at least one implement rotatably coupled to a rotation component, which implement is configured to operably engage one or more gear components of one or more other rotational components. To illustrate, in some embodiments, the rotary units or mechanisms of the invention include one or more gear components that are configured to operably engage one or more implements rotatably coupled to one or more other rotational components. In some embodiments, a rotary unit or a related rotary mechanism of the invention includes at least one implement rotatably coupled to a rotational component. In these embodiments, the implement is optionally configured to operably engage one or more gear components of at least one other rotary unit when the rotary unit is disposed proximal to the other rotary unit such that the implement rotates when at least the rotational component and the other rotary unit rotate relative to one another. Optionally, at least one implement is disposed in, on and/or extending from at least one surface of a rotational component. In some embodiments, for example, implements include one or more of, e.g., a blade, a razor, a prong, a peg, a claw, a tine, a chain, a stake, a column, a pillar, an arch, a bracket, a gear component, a bristle, a plume, an abrasive component, an elastomeric component, a nail filing component, a nail buffing component, a hair cutting component, a massaging component, a post, etc. To further illustrate, at least a portion of an implement comprises at least one cross-sectional shape selected from, e.g., a circle, an oval, a square, a rectangle, a trapezoid, an irregular n-sided polygon, a regular n-sided polygon, and the like.

In certain embodiments, a device or vehicle includes a rotary unit or mechanism of the invention. In some embodiments, the device is selected from, e.g., a held-held device, a rototiller, a hair cutting device, a massaging device, nail grooming device, a propulsion device, a woodworking device, a lathe, a woodchipping device, a machining device, a dermabrasion device, a medical device, a dental device, a cleaning device, an engine, a snow blower, a nozzle, a food preparation device, a grinder, a pencil sharpener, a lawn mower, a vacuum cleaner, a hair dryer, a plumbing device, a weapon, a surfboard, a scuba device, a component thereof, a combination thereof, etc. In certain embodiments, the vehicle includes a farming vehicle, a mining vehicle, a construction vehicle, a submarine, an aircraft, a marine vehicle, a boat, a personal watercraft, a military vehicle, or the like.

The drive mechanisms used with the rotary units and rotary mechanisms of the invention include various embodiments. In certain embodiments, for example, a drive mechanism comprises at least one motor. Optionally, a drive mechanism comprises one or more of, e.g., a drive shaft, a chain drive, a belt drive, a gear drive, or the like. In some embodiments, a drive mechanism comprises at least one flexible drive shaft. To further illustrate, a drive mechanism is optionally operably coupled to a counter-rotational mechanism and/or rotational components via at least one drive shaft, at least one drive chain, at least one belt drive, and/or at least one gear drive.

In another aspect, the invention provides a rotary mechanism that includes at least first, second, and third rotational components in which at least one of the rotational components comprises at least one implement. The rotary mechanism also includes at least first and second counter-rotational mechanisms in which the first counter-rotational mechanism operably engages at least the first and second rotational components, and in which the second counter-rotational mechanism operably engages at least the second and third rotational components. In addition, the rotary mechanism also includes at least one drive mechanism component or a portion thereof operably engaged with one or more of the rotational components and/or with one or more of the counter-rotational mechanisms, which drive mechanism component or portion thereof is configured at least to effect rotation of the rotational components and the counter-rotational mechanisms such that the first and third rotational components rotate in a first direction and the second rotational component rotates in a second direction. Typically, the drive mechanism component or portion thereof is configured to effect rotation of the rotational components and the counter-rotational mechanisms such that the first and third rotational components rotate in a second direction and the second rotational component rotates in a first direction. In some embodiments, the rotary mechanisms of the invention include more than three rotational components (e.g., 4, 5, 6, 7, 8, 9, 10 or more rotational components). In certain embodiments, the second rotational component is disposed between the first and third rotational components. Optionally, at least one of the rotational components comprises one or more gear components that are configured to operably engage one or more implements rotatably coupled to one or more other rotational components. In certain embodiments, at least the first counter-rotational mechanism comprises at least a first gear component disposed on the first rotational component, at least a second gear component disposed on the second rotational component, and at least a third gear component that operably engages the first and second gear components such that when the first gear component rotates in the first direction, the second and third gear components rotate in the second direction and when the first gear component rotates in the second direction, the second and third gear components rotate in the first direction. In some of these embodiments, the rotary mechanism includes a retaining mechanism that retains the third gear component operably engaged with the first and second gear components. In some of these embodiments, the second gear component substantially defines a gear receiving area that is configured to receive at least a portion of the third gear component. Gear components used with the rotary units, rotary mechanisms, and other applications of the invention typically include gear teeth. Any operable gear tooth configuration and/or type are optionally used in the rotary units, rotary mechanisms and applications of the invention.

In one aspect, the invention provides a rotary unit that includes at least a first rotational component configured to rotate around a rotational axis, which first rotational component comprises at least first and second surfaces. The first surface comprises one or more gear components that are configured to operably engage one or more gear components of at least a second rotational component (e.g., of a second rotary unit, etc.) when the first rotational component is disposed proximal to the second rotational component such that when the first rotational component rotates in a first direction, the second rotational component rotates in a second direction. The second surface comprises one or more gear components that are configured to operably engage one or more gear components of at least a third rotational component (e.g., of a third rotary unit, etc.) when the first rotational component is disposed proximal to the third rotational component such that when the first rotational component rotates in the first direction, the third rotational component rotates in the second direction. In addition, at least one surface of the first rotational component comprises at least one implement, which surface is configured to rotate substantially non-perpendicular to the rotational axis. In some embodiments, the surface of the first rotational component that comprises the implement is configured to rotate substantially parallel to the rotational axis. In some embodiments, the first surface comprises one or more sun gear components. In certain embodiments, the second surface comprises one or more ring gear components. In some embodiments, a rotational mechanism comprises the rotary unit. In some embodiments, at least one of the surfaces of the first rotational component comprises at least one friction reducing material. In certain of these embodiments, for example, the friction reducing material is selected from, e.g., a coating, a lubricant, a surface feature, a roller ball, and the like.

In another aspect, the invention provides a rotary mechanism that includes at least two rotary units that each comprises at least one rotational component that comprises at least a first gear component, and at least one second gear component configured to operably engage the first gear component. The rotary mechanism also includes at least one drive mechanism component or portion thereof that operably engages at least the second gear components of at least first and second rotary units. The drive mechanism component or portion thereof is configured to effect rotation of the second gear components such that the rotational component of the first rotary unit rotates in a first direction and the rotational component of the second rotary unit rotates in a second direction. In some embodiments, the first gear component comprises at least one ring gear component. In certain embodiments, at least one surface of at least one of the rotational components comprises at least one implement. In these embodiments, the surface is optionally configured to rotate substantially non-perpendicular to a rotational axis of the rotational components. In other of these embodiments, the surface is optionally configured to rotate substantially parallel to a rotational axis of the rotational components. In some embodiments, the rotary mechanism includes at least one positioning component that is configured to position the rotary units relative to one another. In some of these embodiments, the positioning component comprises a frame structure. Optionally, at least one surface of the positioning component comprises at least one friction reducing material.

In another aspect, the invention provides a rotary mechanism that includes at least two rotary units that each comprise at least one rotational component that comprises at least one sun gear component and at least one ring gear component, and at least one gear structure that comprises at least one support component and at least one planetary gear component rotatably coupled to the support component. The planetary gear component is configured to operably engage the ring gear component. In addition, the sun gear component of at least a first rotary unit operably engages the planetary gear component of at least a second rotary unit such that when the rotational component of the first rotary unit rotates in a first direction, the rotational component of the second rotary unit rotates in a second direction. In some embodiments, the gear structure of the first rotary unit is operably connected to the gear structure of the second rotary unit such that the support components are substantially fixedly positioned relative to one another at least when the rotational component of the first rotary unit rotates in the first direction, the rotational component of the second rotary unit rotates in the second direction. Typically, at least one of the rotational components comprises at least one implement. In some embodiments, at least two of the rotational components are non-concentrically disposed relative to one another. In some embodiments, the rotary mechanism includes at least three, at least four, at least five, at least six, at least seven, at least eight, at least nine, at least ten, or more rotary units.

In another aspect, the invention provides a rotary unit that includes at least one rotational component comprising at least first and second gear components and at least one gear structure receiving area. The first gear component substantially fixedly extends from a first surface of the rotational component. The first gear component is configured to operably engage one or more other gear components of another rotary unit when the first gear component is disposed proximal to the other gear components. The second gear component substantially fixedly extends from a second surface of the rotational component. The second gear component communicates with the gear structure receiving area. The gear structure receiving area is configured to receive one or more gear structures or components thereof. In addition, at least one surface of the rotational component comprises at least one implement. The rotary unit includes at least one gear structure comprising at least one support component and at least a third gear component rotatably coupled to the support component. The third gear component is configured to operably engage one or more other gear components when the third gear component is disposed proximal to the other gear components. Further, the rotational component is configured to rotate relative to the support component, which support component is substantially fixedly positioned when the rotational component rotates relative to the support component. Typically, the first and second surfaces substantially oppose one another. The third gear component is typically configured to rotate relative to the rotational component. In some embodiments, the first gear component comprises at least one sun gear component. In certain embodiments, the second gear component comprises at least one ring gear component. In some embodiments, the third gear component comprises at least one planetary gear component. In certain embodiments, the surface of the rotational component that comprises the implement is configured to rotate substantially non-perpendicular to a rotational axis of the rotary unit. In some embodiments, the surface of the rotational component that comprises the implement is configured to rotate substantially parallel to a rotational axis of the rotary unit. Typically, a rotational mechanism comprises the rotary unit.

In another aspect, the invention provides a rotary unit that includes at least a first rotational component that comprises at least first and second surfaces. The first surface comprises at least a first gear component and the second surface comprises at least a second gear component, which first and second gear components are substantially fixed relative to one another. The first gear component is configured to operably engage one or more third gear components that are configured to operably engage one or more second gear components of at least a second rotational component when the first rotational component is disposed proximal to the second rotational component such that when the first rotational component rotates in a first direction, the second rotational component rotates in a second direction. The second gear component is configured to operably engage one or more third gear components that are configured to operably engage one or more first gear components of at least a third rotational component when the first rotational component is disposed proximal to the third rotational component such that when the first rotational component rotates in the first direction, the third rotational component rotates in the second direction. In addition, the third gear components are configured to rotate in substantially fixed positions relative to one another. In some embodiments, the first gear component comprises at least one sun gear component. In certain embodiments, the second gear component comprises at least one ring gear component. In some embodiments, the third gear components comprise at least one planetary gear component. Typically, one or more gear structures comprise the third gear components. In some embodiments, a rotational mechanism comprises the rotary unit. Typically, at least one surface of the first rotational component comprises at least one implement. In some of these embodiments, the surface of the first rotational component that comprises the implement is configured to rotate substantially non-perpendicular to a rotational axis of the rotary unit. In some of these embodiments, the surface of the first rotational component that comprises the implement is configured to rotate substantially parallel to a rotational axis of the rotary unit.

In another aspect, the invention provides a rotary mechanism that includes at least first, second, and third rotational components in which at least one of the rotational components comprises at least one implement. The rotary mechanism also includes at least first and second counter-rotational mechanisms in which the first counter-rotational mechanism operably engages at least the first and second rotational components. The second counter-rotational mechanism operably engages at least the second and third rotational components. Further, at least portions of the first and second counter-rotational mechanisms are substantially fixedly positioned relative to one another. In addition, the rotary mechanism also includes at least one drive mechanism component or a portion thereof operably engaged with one or more of the rotational components and/or with one or more of the counter-rotational mechanisms. The drive mechanism component or portion thereof is configured at least to effect rotation of the rotational components and the counter-rotational mechanisms such that the first and third rotational components rotate in a first direction and the second rotational component rotates in a second direction.

In another aspect, the invention provides a rotary unit that includes at least a first rotational component that comprises at least one sun gear component and at least one ring gear component. The sun gear component is configured to operably engage one or more gear components of at least a second rotational component such that when the first rotational component rotates in a first direction the second rotational component rotates in a second direction. The ring gear component at least partially defines at least one gear structure receiving area. The rotary unit also includes at least one gear structure at least partially disposed in the gear structure receiving area. The gear structure comprises at least one support component and at least one planetary gear component rotatably coupled to the support component. The support component is substantially fixedly positioned when the planetary gear component rotates relative to the support component. The planetary gear component is configured to operably engage the ring gear component and one or more gear components of at least a third rotational component such that when the first rotational component rotates in the first direction the third rotational component rotates in the second direction. In some embodiments, the support component is configured to operably engage one or more other support components of one or more other rotational components such that the support components are substantially fixedly positioned relative to one another when the rotational components rotate. Typically, the first rotational component comprises at least one implement. In some embodiments, a rotary mechanism comprises the rotary unit.

In another aspect, the invention provides a rotary mechanism that includes at least one drive mechanism component or a portion thereof comprising at least one ring gear component and at least one gear structure that comprises at least one support component and at least one planetary gear component rotatably coupled to the support component, which planetary gear component is configured to operably engage the ring gear component. In addition, the rotary mechanism also includes at least one rotary unit that comprises at least one rotational component comprising at least one ring gear component and at least one sun gear component, and at least one gear structure that comprises at least one support component and at least one planetary gear component rotatably coupled to the support component, which planetary gear component is configured to operably engage the ring gear component. The planetary gear component of the drive mechanism component or a portion thereof is configured to operably engage the sun gear component of the rotary unit such that when the drive mechanism component or a portion thereof effects rotation of the ring gear component of the drive mechanism component or a portion thereof in a first direction, the rotational component of the rotary unit rotates in a second direction. In some embodiments, at least one of the rotational components and/or the ring gear component of the drive mechanism component or the portion thereof comprises at least one implement.

In some embodiments, the gear structure of the drive mechanism component or the portion thereof is operably connected to the gear structure of the rotary unit such that the support components are substantially fixedly positioned relative to one another at least when the ring gear component of the drive mechanism component or the portion thereof rotates in the first direction, the rotational component of the rotary unit rotates in the second direction. In certain embodiments, the rotary mechanism includes at least three, at least four, at least five, at least six, at least seven, at least eight, at least nine, at least ten, or more rotary units.

In another aspect, the invention provides a rotary or rotational mechanism that includes at least a first rotary unit that comprises at least one rotational component that comprises at least first and second sun gear components. The rotational mechanism also includes at least a second rotary unit that comprises at least one rotational component that comprises at least first and second ring gear components. In addition, the rotational mechanism also includes at least a first planetary gear component that is configured to operably engage the second sun gear component of the first rotary unit and the first ring gear component of the second rotary unit such that when the rotational component of the first rotary unit rotates in a first direction, the rotational component of the second rotary unit rotates in a second direction.

In some embodiments, the rotational components of the first and second rotary units are configured to rotate at different rates relative to one another. In some embodiments, the rotational mechanism includes at least one gear structure that comprises at least one support component in which the first planetary gear component is rotatably coupled to the support component. In certain embodiments, the rotational mechanism includes at least a second planetary gear component that is configured to operably engage one or more gear components of at least a third rotary unit and the second ring gear component of the second rotary unit such that when the rotational component of the second rotary unit rotates in the second direction, a rotational component of the third rotary unit rotates in the first direction.

In some embodiments, the first sun gear component of the first rotary unit is configured to operably engage one or more gear components of at least a fourth rotary unit such that when the rotational component of the first rotary unit rotates in the first direction, a rotational component of the fourth rotary unit rotates in the second direction. In some of these embodiments, the first sun gear component of the first rotary unit is configured to operably engage the one or more gear components of the fourth rotary unit via one or more planetary gear components.

In certain embodiments, the rotational mechanism includes more than two rotary units. In some of these embodiments, a sum of rotational rates of the rotational components of a first pair of neighboring rotary units is configured to be substantially identical to a sum of rotational rates of the rotational components of a second pair of neighboring rotary units when the rotational components rotate relative to one another.

In another aspect, the invention provides a cleaning device that includes at least one head component that comprises at least one cleaning material support component and at least one cleaning surface component. In some embodiments, the cleaning surface component comprises at least one elevational element. The cleaning material support component comprises at least one cleaning material support component surface that at least partially defines at least one cleaning material cartridge receiving area. The cleaning material support component comprises at least one opening such that the cleaning material cartridge receiving area communicates with the cleaning surface component. In addition, the cleaning material cartridge receiving area is configured to receive at least one cleaning material cartridge comprising cleaning material such that at least a portion of the cleaning material is movable to and/or from the cleaning material cartridge receiving area to extend over at least a portion of the cleaning surface component when the cleaning material cartridge is at least partially disposed in the cleaning material cartridge receiving area. The cleaning device also includes at least one rotary mechanism comprising at least one rotational component that comprises at least one implement.

In some embodiments, the rotary mechanism of the cleaning device comprises at least first, second, and third rotational components. In these embodiments, the rotary mechanism also includes at least first and second counter-rotational mechanisms. The first counter-rotational mechanism operably engages at least the first and second rotational components. The second counter-rotational mechanism operably engages at least the second and third rotational components. In these embodiments, the rotary mechanism also includes at least one drive mechanism component or a portion thereof operably engaged with one or more of the rotational components and/or with one or more of the counter-rotational mechanisms, which drive mechanism component or portion thereof is configured at least to effect rotation of the rotational components and the counter-rotational mechanisms such that the first and third rotational components rotate in a first direction and the second rotational component rotates in a second direction. In some of these embodiments, the implement comprises a plurality of bristles.

In some embodiments, the cleaning device includes at least one positioning mechanism component that is configured to selectively position the cleaning material at least relative to the cleaning material support component when the cleaning material cartridge is at least partially disposed in the cleaning material cartridge receiving area. In some embodiments, the cleaning device includes at least two cleaning material support components that are each configured to receive at least a component of the cleaning material cartridge. In some embodiments, the cleaning device includes at least one retaining component that is configured to substantially retain the cleaning material cartridge at a selected position relative to the cleaning material support component when the cleaning material cartridge is at least partially disposed in the cleaning material cartridge receiving area. In some embodiments, the cleaning device includes at least one retaining mechanism that is configured to substantially retain the cleaning material at a selected position relative to the cleaning surface component when the cleaning material cartridge is at least partially disposed in the cleaning material cartridge receiving area and the cleaning material extends over at least the portion of the cleaning surface component. In some embodiments, the cleaning device includes the cleaning material cartridge at least partially disposed in the cleaning material cartridge receiving area of the cleaning material support component. In some embodiments, the cleaning device includes at least one handle operably connected to the head component. In some of these embodiments, the handle is pivotally connected to the head component via at least one pivot mechanism.

In some embodiments, the cleaning device includes at least one conveyance mechanism, or at least one component thereof, that is configured to convey at least the cleaning material over at least the portion of the cleaning surface component when the cleaning material cartridge is at least partially disposed in the cleaning material cartridge receiving area. In some embodiments, the conveyance mechanism is manually operated via at least one manual conveyance component. In some embodiments, the conveyance mechanism or the component thereof is configured to operably engage the cleaning material cartridge to effect conveyance of the cleaning material when the cleaning material cartridge is at least partially disposed in the cleaning material cartridge receiving area. In some embodiments, the conveyance mechanism is configured to convey the cleaning material at least one selected incremental distance. In some embodiments, the conveyance mechanism comprises one or more gear components. In some embodiments, the conveyance mechanism comprises at least one motor component that is configured to effect conveyance of the cleaning material when the cleaning material cartridge is at least partially disposed in the cleaning material cartridge receiving area.

In some embodiments, the cleaning device includes at least one fluid handling mechanism or at least one component thereof that is configured to convey at least one fluid from at least one fluid source to at least one fluid outlet. In some embodiments, the fluid outlet communicates with the cleaning material cartridge or a portion thereof when the cleaning material cartridge is at least partially disposed in the cleaning material cartridge receiving area. In some embodiments, the fluid outlet is disposed proximal to at least one surface of the head component. In some embodiments, the fluid outlet comprises at least one nozzle. In some embodiments, the fluid handling mechanism comprises at least one pumping mechanism that is configured to pump the fluid from the fluid source to the fluid outlet. In some embodiments, the fluid handling mechanism comprises at least one vaporization component that is configured to vaporize the fluid at least proximal to the fluid outlet. In some embodiments, the fluid source and fluid outlet communicate via at least one fluid conduit. In some embodiments, the fluid source comprises at least one fluid container. In some of these embodiments, the fluid container is removable.

In another aspect, the invention provides a device that includes at least two rotational units, and at least one rotary mechanism configured to operably engage at least one of the rotational units to effect counter-rotation of neighboring pairs of the rotational units. In some embodiments, at least one of the rotational units comprises at least one propeller unit.

In another aspect, the invention provides a device that includes at least two rotational units in which at least one of the rotational units comprises at least one implement and at least one gear component, and at least one rotary mechanism that operably engages the gear component such that when the rotary mechanism rotates, neighboring pairs of rotational units counter-rotate relative to one another. In some embodiments, the device includes at least three, at least four, at least five, at least six, at least seven, at least eight, at least nine, at least ten, or more rotational units. In certain embodiments, the implement comprises at least one propeller component. In some embodiments, at least one surface of the at least one rotational unit comprises the gear component, which surface is configured to rotate substantially non-perpendicular to a rotational axis of the rotational units and/or the rotary mechanism. In certain embodiments, the gear component is disposed at least partially around the implement. In some embodiments, the rotary mechanism comprises at least two rotary units that operably engage gear components of different rotational units in which the rotary units are configured to counter-rotate relative to one another. In some embodiments, at least one of the rotational units and/or the rotary mechanism comprises at least one rotational alignment component. In certain embodiments, the device includes at least one drive mechanism operably connected to the rotational units and/or to the rotary mechanism. In some embodiments, the device includes at least one positioning component (e.g., a housing, a frame structure, or the like) configured to position the rotational units and the rotary mechanism relative to one another. In some embodiments, the device includes at least two rotary mechanisms, wherein at least a first rotary mechanism operably engages the gear component of at least a first rotational unit, wherein at least a second rotary mechanism operably engages the gear component of at least a second rotational unit, and wherein the first rotary mechanism is configured to rotate in at least a first direction and the second rotary mechanism is configured to rotate in at least a second direction such that when the first and second rotary mechanisms rotate, the first rotational unit rotates in the first direction and the second rotational unit rotates in the second direction. In some of these embodiments, the first rotary mechanism operably engages the gear components of at least a first set of non-neighboring rotational units and wherein the second rotary mechanism operably engages the gear components of at least a second set of non-neighboring rotational units.

In another aspect, the invention provides a cleaning device that includes at least one rotary mechanism that comprises at least two rotational components that are non-concentrically disposed relative to one another and are configured to counter-rotate relative to one another around a rotational axis in which at least one surface of at least one of the rotational components comprises at least one implement (e.g., bristles or the like), which surface is configured to rotate substantially non-perpendicular to the rotational axis. In some embodiments, the rotary mechanism comprises at least three, at least four, at least five, at least six, at least seven, at least eight, at least nine, at least ten, or more rotational components. In some embodiments, the cleaning device includes at least one head component in which the rotary mechanism is at least partially disposed within the head component. Optionally, at least one handle is operably connected to the head component.

In some embodiments, the cleaning device includes at least one fluid handling mechanism or at least one component thereof that is configured to convey at least one fluid from at least one fluid source to at least one fluid outlet. In certain embodiments, the fluid outlet is disposed proximal to at least one surface of a head component. In some embodiments, the fluid outlet comprises at least one nozzle. In certain embodiments, the fluid handling mechanism comprises at least one pumping mechanism that is configured to pump the fluid from the fluid source to the fluid outlet. In some embodiments, the fluid handling mechanism comprises at least one vaporization component that is configured to vaporize the fluid at least proximal to the fluid outlet. In some embodiments, the fluid source and fluid outlet communicate via at least one fluid conduit. In certain embodiments, the fluid source comprises at least one fluid container. In some embodiments, the fluid container is removable.

In certain embodiments, the cleaning device includes at least one suction component that comprises at least one inlet and at least one outlet. Typically, the suction component comprises at least one vacuum source. In some embodiments, the inlet is disposed proximal to the rotary mechanism and/or a head component that at least partially comprises the rotary mechanism. In some embodiments, the cleaning device includes at least one waste container in which the outlet of the suction component communicates with the waste container. In some embodiments, the outlet and the waste container communicate via at least one conduit. In certain embodiments, the waste container is removable.

In another aspect, the invention provides methods of rotating implements. In some embodiments, the methods include providing a rotary mechanism that comprises at least three rotary units that each comprises at least one rotational component that comprises at least one sun gear component and at least one ring gear component, and at least one gear structure that comprises at least one support component and at least one planetary gear component rotatably coupled to the support component, wherein the planetary gear component operably engages the ring gear component, wherein the sun gear component of at least a first rotary unit operably engages the planetary gear component of at least a second rotary unit, wherein the sun gear component of the second rotary unit operably engages the planetary gear component of at least a third rotary unit, and wherein at least one of the rotational components comprises at least one implement. In these embodiments, the methods also include moving at least a portion of one or more of the rotary units such that the rotational components of first and third rotary units rotate in a first direction and the rotational component of the second rotary unit rotates in a second direction, thereby rotating the implement.

BRIEF DESCRIPTION OF THE DRAWINGS

The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown. In addition, in certain figures implements are schematically illustrated as cross-hatches on rotary units.

FIG. 1A schematically illustrates a rotary unit from a front side view according to one embodiment of the invention.

FIG. 1B schematically shows the rotary unit of FIG. 1A from a rear side view.

FIG. 1C schematically depicts the rotary unit of FIG. 1A from a side view.

FIG. 1D schematically shows a gear structure of the rotary unit of FIG. 1A from a rear side view.

FIG. 1E schematically illustrates the gear structure of FIG. 1D from a front side view.

FIG. 1F schematically shows the gear structure of FIG. 1D from a side view.

FIG. 1G schematically illustrates a sectional view of the rotary unit of FIG. 1A.

FIG. 1H schematically shows a sectional view of the rotary unit of FIG. 1A.

FIG. 1I schematically depicts a partially exploded view of the rotary unit of FIG. 1A.

FIGS. 2 A-F schematically show side elevational views of various exemplary implements.

FIG. 3A schematically illustrates a rotary unit from a front side view according to one embodiment of the invention.

FIG. 3B schematically shows the rotary unit of FIG. 3A from a rear side view.

FIG. 3C schematically shows the rotary unit of FIG. 3A from a side view.

FIG. 3D schematically depicts a sectional view of the rotary unit of FIG. 3A.

FIG. 3E schematically shows a gear structure of the rotary unit of FIG. 3A from a rear side view.

FIG. 3F schematically shows a gear structure of the rotary unit of FIG. 3A from a front side view.

FIG. 3G schematically shows a gear structure of the rotary unit of FIG. 3A from a side view.

FIG. 4A schematically illustrates a rotary unit from a front side view according to one embodiment of the invention.

FIG. 4B schematically shows the rotary unit of FIG. 4A from a rear side view.

FIG. 4C schematically shows the rotary unit of FIG. 4A from a side view.

FIG. 4D schematically depicts a sectional view of the rotary unit of FIG. 4A.

FIG. 4E schematically shows a gear structure of the rotary unit of FIG. 4A from a front side view.

FIG. 4F schematically shows a gear structure of the rotary unit of FIG. 4A from a rear side view.

FIG. 4G schematically shows a gear structure of the rotary unit of FIG. 4A from a side view.

FIG. 5A schematically illustrates a rotary unit from a side view according to one embodiment of the invention.

FIG. 5B schematically shows a sectional view of the rotary unit of FIG. 5A.

FIG. 6A schematically shows a rotary unit from a front side view according to one embodiment of the invention.

FIG. 6B schematically illustrates the rotary unit of FIG. 6A from a side view.

FIG. 6C schematically depicts the rotary unit of FIG. 6A from a rear side view.

FIG. 6D schematically shows a sectional view of the rotary unit of FIG. 6A.

FIG. 6E schematically illustrates a gear structure of the rotary unit of FIG. 6A from a rear side view.

FIG. 6F schematically shows the gear structure of FIG. 6E from a front side view.

FIG. 6G schematically illustrates the gear structure of FIG. 6E from a front side view.

FIG. 7A schematically shows a rotary unit from a front side view according to one embodiment of the invention.

FIG. 7B schematically shows the rotary unit of FIG. 7A from a rear side view.

FIG. 7C schematically depicts the rotary unit of FIG. 7A from a side view.

FIG. 8A schematically shows a rotary unit from a front side view according to one embodiment of the invention.

FIG. 8B schematically shows the rotary unit of FIG. 8A from a rear side view.

FIG. 8C schematically depicts the rotary unit of FIG. 8A from a side view.

FIG. 9A schematically illustrates a rotary unit from a front side view according to one embodiment of the invention.

FIG. 9B schematically shows the rotary unit of FIG. 9A from a rear side view.

FIG. 9C schematically depicts the rotary unit of FIG. 9A from a side view.

FIG. 9D schematically shows schematically shows a sectional view of the rotary unit of FIG. 9A.

FIG. 9E schematically illustrates a sectional view of the rotary unit of FIG. 9A.

FIG. 9F schematically shows a gear structure of the rotary unit of FIG. 9A from a rear side view.

FIG. 9G schematically illustrates the gear structure of FIG. 9F from a front side view.

FIG. 9H schematically shows the gear structure of FIG. 9F from a side view.

FIG. 9I schematically depicts a partially exploded view of the rotary unit of FIG. 9A.

FIG. 9J schematically shows the rotary unit of FIG. 9A with implements from a rear side view.

FIG. 9K schematically shows the rotary unit of FIG. 9A with implements from a front side view.

FIG. 9L schematically shows the rotary unit of FIG. 9A with implements from a side view.

FIG. 10A schematically illustrates a rotary unit from a front side view according to one embodiment of the invention.

FIG. 10B schematically shows the rotary unit of FIG. 10A from a rear side view.

FIG. 10C schematically depicts the rotary unit of FIG. 10A from a side view.

FIG. 10D schematically shows schematically shows a sectional view of the rotary unit of FIG. 10A.

FIG. 10E schematically shows a gear structure of the rotary unit of FIG. 10A from a front side view.

FIG. 10F schematically illustrates the gear structure of FIG. 10E from a rear side view.

FIG. 10G schematically shows the gear structure of FIG. 10E from a side view.

FIG. 10H schematically illustrates a sectional view of the rotary unit of FIG. 10A.

FIG. 10I schematically depicts the rotary unit of FIG. 10A including a friction reducing material from a front side view.

FIG. 10J schematically depicts the rotary unit of FIG. 10A including a friction reducing material from a side view.

FIG. 10K schematically shows the rotary unit of FIG. 10I with implements from a front side view.

FIG. 10L schematically shows the rotary unit of FIG. 10A with implements from a rear side view.

FIG. 10M schematically shows the rotary unit of FIG. 10I with implements from a side view.

FIG. 11A schematically illustrates a rotary unit from a front side view according to one embodiment of the invention.

FIG. 11B schematically shows the rotary unit of FIG. 11A from a rear side view.

FIG. 11C schematically depicts the rotary unit of FIG. 11A from a side view.

FIG. 11D schematically shows schematically shows a sectional view of the rotary unit of FIG. 11A.

FIG. 11E schematically shows the rotary unit of FIG. 11A with implements from a front side view.

FIG. 11F schematically shows the rotary unit of FIG. 11A with implements from a rear side view.

FIG. 11G schematically shows the rotary unit of FIG. 11A with implements from a side view.

FIG. 12A schematically illustrates a rotary unit from a front side view according to one embodiment of the invention.

FIG. 12B schematically shows the rotary unit of FIG. 12A from a rear side view.

FIG. 12C schematically depicts the rotary unit of FIG. 12A from a side view.

FIG. 12D schematically shows a gear structure of the rotary unit of FIG. 12A from a front side view.

FIG. 12E schematically illustrates the gear structure of FIG. 12D from a rear side view.

FIG. 12F schematically shows the gear structure of FIG. 12D from a side view.

FIG. 13A schematically illustrates a rotational component of a rotary unit from a front side view according to one embodiment of the invention.

FIG. 13B schematically shows a sectional view of the rotational component of FIG. 13A.

FIG. 13C schematically depicts the rotational component of FIG. 13A from a side view.

FIG. 13D schematically shows a gear component used in the rotary unit referred to with respect to FIG. 13A from a front side view.

FIG. 13E schematically illustrates the gear component of FIG. 13D from a side view.

FIG. 14A schematically illustrates a rotary unit from a front side view according to one embodiment of the invention.

FIG. 14B schematically depicts the rotary unit of FIG. 14A from a side view.

FIG. 14C schematically shows the rotary unit of FIG. 14A from a rear side view.

FIG. 14D schematically shows a sectional view of the gear structure of FIG. 14A.

FIG. 15A schematically illustrates a rotary unit from a front side view according to one embodiment of the invention.

FIG. 15B schematically shows the rotary unit of FIG. 15A from a rear side view.

FIG. 15C schematically depicts the rotary unit of FIG. 15A from a side view.

FIG. 15D schematically shows schematically shows a sectional view of the rotary unit of FIG. 15A.

FIG. 16A schematically illustrates a rotary unit from a front side view according to one embodiment of the invention.

FIG. 16B schematically shows the rotary unit of FIG. 16A from a rear side view.

FIG. 16C schematically depicts the rotary unit of FIG. 16A from a side view.

FIG. 16D schematically shows schematically shows a sectional view of the rotary unit of FIG. 16A.

FIG. 16E schematically illustrates a planetary gear component from a front side view according to one embodiment of the invention.

FIG. 16F schematically illustrates the planetary gear component of FIG. 16E from a side view.

FIG. 16G schematically shows an exploded side view of a gear structure according to one embodiment of the invention.

FIG. 16H schematically depicts the gear structure of FIG. 16G from a side view.

FIG. 16I schematically shows the gear structure of FIG. 16H from a rear side view.

FIG. 16J schematically shows the gear structure of FIG. 16H from a front side view.

FIG. 16K schematically illustrates a gear structure prior to assembly with another gear structure from a side view according to one embodiment of the invention.

FIG. 16L schematically shows an assembly that includes two gear structures from a side view according to one embodiment of the invention.

FIG. 16M schematically shows an exploded view of the rotary unit of FIG. 16A with the gear structure of FIG. 16G from a side view according to one embodiment of the invention.

FIG. 16N schematically shows the rotary unit of FIG. 16A with the gear structure of FIG. 16G from a front side view.

FIG. 16O schematically shows the rotary unit of FIG. 16A with the gear structure of FIG. 16G from a rear side view.

FIG. 16P schematically shows the rotary unit of FIG. 16A with the gear structure of FIG. 16G from a side view.

FIG. 16Q schematically shows a sectional view of the rotary unit of FIG. 16A with the gear structure of FIG. 16G.

FIG. 17A schematically depicts rotary units and a shaft from side elevational views prior to assembly according to one embodiment of the invention.

FIG. 17B schematically illustrates the rotary units and the shaft from FIG. 17A from side elevational views in an assembled format.

FIG. 18A schematically shows rotary units prior to assembly of a rotary mechanism from side views according to one embodiment of the invention.

FIG. 18B schematically shows a partially assembled rotary mechanism with the rotary units of FIG. 18A from side views.

FIG. 18C schematically illustrates a rotary mechanism that includes the rotary units of FIG. 18A from a side view.

FIG. 19A schematically illustrates a rotary mechanism that includes the rotary unit of FIG. 9A from a sectional view prior to assembly according to one embodiment of the invention.

FIG. 19B schematically depicts the rotary mechanism of FIG. 19A from a sectional view following assembly.

FIG. 19C schematically shows a portion of a rotary mechanism that includes the rotary unit of FIG. 9A with implements from a side view according to one embodiment of the invention.

FIG. 20A schematically illustrates a positioning component of a rotary mechanism from a side view according to one embodiment of the invention.

FIG. 20B schematically depicts a portion of a rotary mechanism that includes the rotational component of FIG. 13A from a side view according to one embodiment of the invention.

FIG. 20C schematically depicts a portion of a rotary mechanism that includes the rotational component of FIG. 13A and gear component of FIG. 13D from a side view according to one embodiment of the invention.

FIG. 20D schematically shows the portion of the rotary mechanism of FIG. 20B from a sectional view.

FIG. 20E schematically depicts the positioning component of FIG. 20A from a side view.

FIG. 20F schematically shows the positioning component of FIG. 20A with a drive mechanism from a side view.

FIG. 20G schematically illustrates a positioning component of a rotary mechanism from a side view according to one embodiment of the invention.

FIG. 20H schematically illustrates a rotary mechanism that includes the rotational component of FIG. 13A from a side view according to one embodiment of the invention.

FIG. 20I schematically shows the rotary mechanism of FIG. 20H from a sectional view.

FIG. 20J schematically shows the rotary mechanism of FIG. 20H from a front side view.

FIG. 20K schematically shows the rotary mechanism of FIG. 20H from a rear side view.

FIG. 20L schematically depicts a portion of a drive mechanism from a side view according to one embodiment of the invention.

FIG. 20M schematically depicts a portion of a drive mechanism from a side view according to one embodiment of the invention.

FIG. 20N schematically depicts the portion of the drive mechanism of FIG. 20M without a motor from a side view.

FIG. 20O schematically depicts the portion of the drive mechanism of FIG. 20M from a side view.

FIG. 21A schematically illustrates a rotary mechanism that includes the rotary unit of FIG. 14A from a sectional view prior to assembly according to one embodiment of the invention.

FIG. 21B schematically depicts the rotary mechanism of FIG. 21A from a sectional view following assembly.

FIG. 21C schematically shows the rotary of FIG. 21A from a side view.

FIG. 21D schematically illustrates a rotary mechanism that includes the rotary unit of FIG. 14A with implements from a side view according to one embodiment of the invention.

FIG. 21E schematically illustrates a rotary mechanism that includes the rotary unit of FIG. 14A with implements from a side view according to one embodiment of the invention.

FIG. 22A schematically illustrates a gear structure from the rotary unit of FIG. 14A prior to assembly with another gear structure from a side view according to one embodiment of the invention.

FIG. 22B schematically shows an assembly of multiple gear structures from a side view according to one embodiment of the invention.

FIG. 22C schematically depicts the gear structure assembly of FIG. 22B from a rear side view.

FIG. 22D schematically depicts the gear structure assembly of FIG. 22B from a front side view.

FIG. 22E schematically shows a rotary mechanism that includes the gear structure assembly of FIG. 22B from a sectional view according to one embodiment of the invention.

FIG. 22F schematically shows a rotary mechanism that includes the gear structure assembly of FIG. 22B from a side view according to one embodiment of the invention.

FIG. 23A schematically depicts a rotational mechanism from an exploded side view according to one embodiment of the invention.

FIG. 23B schematically depicts the rotational mechanism from FIG. 23A from a side view.

FIG. 23C schematically depicts the rotational mechanism from FIG. 23A from an exploded sectional view.

FIG. 23D schematically depicts the rotational mechanism from FIG. 23A from a sectional side view.

FIG. 23E schematically shows a portion of a drive mechanism component from a front side view according to one embodiment of the invention.

FIG. 23F schematically shows the portion of the drive mechanism component of FIG. 23E from a rear side view.

FIG. 23G schematically shows the portion of the drive mechanism component of FIG. 23E from a side view.

FIG. 23H schematically shows the portion of the drive mechanism component of FIG. 23E from a sectional side view.

FIG. 23I schematically shows an exploded side view of a gear structure according to one embodiment of the invention.

FIG. 23J schematically depicts the gear structure from FIG. 23I from a rear side view.

FIG. 23K schematically depicts the gear structure from FIG. 23I from a side view.

FIG. 23L schematically depicts the gear structure from FIG. 23I from a front side view.

FIG. 23M schematically shows an exploded side view of the drive mechanism component of FIG. 23E and the gear structure of FIG. 23I according to one embodiment of the invention.

FIG. 23N schematically shows an exploded sectional side view of the drive mechanism component of FIG. 23E and the gear structure of FIG. 23I according to one embodiment of the invention.

FIG. 23O schematically depicts the drive mechanism component of FIG. 23E and the gear structure of FIG. 23I from a side view.

FIG. 23P schematically depicts the drive mechanism component of FIG. 23E and the gear structure of FIG. 23I from sectional side view.

FIG. 23Q schematically depicts an exploded side view of the rotational mechanism from FIG. 23B and the portion of the drive mechanism component of FIG. 23E according to one embodiment of the invention.

FIG. 23R schematically depicts an exploded side sectional view of the rotational mechanism from FIG. 23B and the portion of the drive mechanism component of FIG. 23E according to one embodiment of the invention.

FIG. 23S schematically depicts a side view of the rotational mechanism from FIG. 23B and the portion of the drive mechanism component of FIG. 23E according to one embodiment of the invention.

FIG. 23T schematically depicts a sectional side view of the rotational mechanism from FIG. 23B and the portion of the drive mechanism component of FIG. 23E according to one embodiment of the invention.

FIG. 24A schematically illustrates a rotor tiller that includes a rotary mechanism from a front elevational view according to one embodiment of the invention.

FIG. 24B schematically illustrates the rotor tiller from FIG. 24A from a side elevational view.

FIG. 25A schematically illustrates a vehicle that includes rotary mechanisms from a side elevational view according to one embodiment of the invention.

FIG. 25B schematically illustrates a vehicle that includes rotary mechanisms from a side elevational view according to one embodiment of the invention.

FIG. 26A schematically shows a rotary mechanism of a hair cutting device from a side elevational view according to one embodiment of the invention.

FIG. 26B schematically shows a removable structure of a hair cutting device from a side elevational view according to one embodiment of the invention.

FIG. 26C schematically shows the rotary mechanism of FIG. 26A positioned in a housing of a hair cutting device from a partial cross-sectional view according to one embodiment of the invention.

FIG. 26D schematically shows the rotary mechanism of FIG. 26A positioned in a housing of a hair cutting device prior to placing a removable structure in an opening of the housing from side elevational views according to one embodiment of the invention.

FIG. 26E schematically shows the hair cutting device from FIG. 26D with the removable structure positioned in the opening of the housing from a side elevational view according to one embodiment of the invention.

FIG. 26F schematically illustrates a person shaving facial hair using the hair cutting device from FIG. 26E from a side elevational view according to one embodiment of the invention.

FIG. 26G schematically illustrates a cross-section of the hair cutting device from FIG. 26E.

FIG. 27A schematically illustrates a partially exploded view of a tooth brushing device according to one embodiment of the invention.

FIG. 27B schematically shows an assembled tooth brushing device from FIG. 27A from a side view.

FIG. 27C schematically depicts the tooth brushing device of FIG. 27B from a top side view.

FIG. 27D schematically depicts a rotary mechanism from the tooth brushing device of FIG. 27B from a side view.

FIG. 28A schematically shows a rotary mechanism for a tooth brushing device from a side view according to one embodiment of the invention.

FIG. 28B schematically depicts a toothbrush head component that includes the rotary mechanism of FIG. 28A from a side view according to one embodiment of the invention.

FIG. 29 schematically illustrates a cleaning device from a side view according to one embodiment of the invention.

FIG. 30A schematically illustrates an exploded view of a propulsion device according to one embodiment of the invention.

FIG. 30B schematically shows the propulsion device of FIG. 30A from a partially exploded view.

FIG. 30C schematically shows the propulsion device of FIG. 30A from a partially exploded view.

FIG. 30D schematically illustrates the propulsion device of FIG. 30A from a side view.

FIG. 30E schematically shows the propulsion device of FIG. 30A from a front side view.

FIG. 30F schematically shows the propulsion device of FIG. 30A from a rear side view.

FIG. 31A schematically illustrates the propulsion device of FIG. 30A disposed within a housing from a front side view according to one embodiment of the invention.

FIG. 31B schematically illustrates the propulsion device of FIG. 30A disposed within a housing from a rear side view according to one embodiment of the invention.

FIG. 31C schematically illustrates the propulsion device of FIG. 30A disposed within a housing from a side view according to one embodiment of the invention.

FIG. 31D schematically illustrates the propulsion device of FIG. 30A disposed within a housing from a partially sectional front side view according to one embodiment of the invention.

FIG. 31E schematically illustrates the propulsion device of FIG. 30A disposed within a housing from a partially sectional side view according to one embodiment of the invention.

FIG. 32A schematically shows a propulsion device including rotary mechanisms from a partially exploded view according to one embodiment of the invention.

FIG. 32B schematically illustrates the propulsion device of FIG. 32A from a side view.

FIG. 32C schematically shows the propulsion device of FIG. 32A from a front side view.

FIG. 32D schematically shows the propulsion device of FIG. 32A from a rear side view.

FIG. 33A schematically shows a boat that includes propulsion devices from a side view according to one embodiment of the invention.

FIG. 33B schematically illustrates the boat of FIG. 33A from a front side view.

FIG. 34A schematically shows an aircraft that includes propulsion devices from a front side view according to one embodiment of the invention.

FIG. 34B schematically illustrates the aircraft of FIG. 34A from a side view.

FIG. 35A schematically shows a cleaning device that includes a rotary mechanism from a sectional view according to one embodiment of the invention.

FIG. 35B schematically shows the cleaning device of FIG. 35A from a side view.

FIG. 36A schematically depicts a rotary mechanism from a top view according to one embodiment of the invention.

FIG. 36B schematically illustrates the rotary mechanism of FIG. 36A from a side view.

FIG. 36C schematically illustrates the rotary mechanism of FIG. 36A from a front side view.

FIG. 36D schematically illustrates the rotary mechanism of FIG. 36A from a rear side view.

FIG. 36E schematically shows a head component of a cleaning device that includes the rotary mechanism of FIG. 36A from an exploded side view.

FIG. 36F schematically shows the head component of FIG. 36A from a sectional view.

FIG. 36G schematically shows a cleaning device that includes the head component of FIG. 36A from a side view according to one embodiment of the invention.

FIG. 37 schematically shows a rotary mechanism from a top side view according to one embodiment of the invention.

FIG. 38 schematically shows a cleaning device that includes a rotary mechanism from a side view according to one embodiment of the invention.

FIG. 39 schematically shows a cleaning device that includes the rotary mechanism of FIG. 37A from a side view according to one embodiment of the invention.

FIG. 40A schematically shows a cleaning device that includes the rotary mechanism of FIG. 37A and removable fluid containers prior to assembly from a side view according to one embodiment of the invention.

FIG. 40B schematically shows the cleaning device of FIG. 40A following assembly from a side view.

FIGS. 41A-Q schematically show a cleaning device or implement, a cleaning material component, or components thereof from various views according to one exemplary embodiment of the invention. FIG. 41A schematically illustrates a head component of a cleaning device that includes the rotary mechanism of FIG. 21E from a side view according to one embodiment of the invention. FIG. 41B schematically shows the head component of the cleaning device of FIG. 41A including a cleaning material cartridge from a side view. FIG. 41C schematically depicts the cleaning device of FIG. 41A with an exemplary retaining component in a closed position from a side view. FIG. 41D schematically depicts the cleaning device of FIG. 41A with components of an exemplary fluid handling mechanism from a side view. FIG. 41E schematically shows a cleaning material cartridge being inserted into the cleaning material support component of the cleaning device of FIG. 41A from a side view. FIG. 41F schematically shows a cleaning material cartridge operably engaging a conveyance mechanism of the cleaning device of FIG. 41A from a top side view. FIG. 41G schematically depicts the head component of the cleaning device of FIG. 41A from a sectional top side view. FIG. 41H schematically depicts a cleaning material cartridge of the cleaning device of FIG. 41A from a side view. FIG. 50I schematically depicts a cleaning material cartridge of the cleaning device of FIG. 41A from a side view. FIG. 41J schematically depicts a cleaning material cartridge of the cleaning device of FIG. 41A from a top side view. FIG. 41K schematically shows a cleaning material cartridge of the cleaning device of FIG. 41A from a bottom side view. FIG. 41L schematically depicts a cleaning material cartridge of the cleaning device of FIG. 41A from a side view. FIG. 41M schematically shows a sectional view of a cleaning material support component of a cleaning material cartridge according to one embodiment of the invention. FIG. 41N schematically shows the head component of a cleaning device of FIG. 41A with a handle and a removable fluid container being positioned relative to the cleaning device from a side view. FIG. 41O schematically shows the head component of a cleaning device of FIG. 41A with a handle from a side view. FIG. 41P schematically shows the cleaning device of FIG. 41O with a handle from a front side view. FIG. 41Q schematically depicts the head component of the cleaning device of FIG. 41A including an elevational element from a side view.

DETAILED DESCRIPTION

I. Introduction

Before describing the invention in detail, it is to be understood that this invention is not limited to particular methods, rotary units, rotary mechanisms, devices, or systems, which can vary. As used in this specification and the appended claims, the singular forms "a," "an," and "the" also include plural referents unless the context clearly provides otherwise. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the invention, the following terminology, and grammatical variants thereof, will be used in accordance with the definitions set forth below.

The term "coaxially positioned" refers to objects that are positioned relative to one another such that they can rotate about a substantially coincident axis.

The term "fixed position" refers to objects that are positioned relative to one another such that they do not move separately from one another. In some embodiments, for example, gear components (e.g., sun gear components) are attached (e.g., integrally fabricated, bonded, welded, adhered, or the like) to rotational components, such that when the rotational components move in one direction, the gear components move in the same direction as the rotational components.

The term "counter-rotate" or "contra-rotate" refers to objects that rotate in opposite directions relative to one another. In some embodiments, for example, rotary mechanisms include rotational components that are configured to rotate in opposite directions.

The term "communicate" refers to the direct or indirect transfer or transmission, and/or capability of directly or indirectly transferring or transmitting, something at least from one thing to another thing. In some embodiments, for example, devices include housings having openings through which hair, finger nails, or the like can be transferred to contact implements within housing cavities of the devices.

The invention relates to rotary units and rotary mechanisms that are suitable for use in numerous applications. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate. The representative embodiments described herein are intended to illustrate, but not to limit, the invention. Essentially any combination of components or portions thereof described herein are optionally utilized or adapted for use together in certain embodiments.

II. Exemplary Rotary Units

FIGS. 1 A-H schematically show a rotary unit or components thereof according to one embodiment of the invention. As shown, rotary unit 100 includes rotational component 102, which includes first gear component 104 disposed on a first side of rotational component 102 (e.g., in an inner region of the first side) and second gear component 106 disposed on a second side of rotational component 102 (e.g., in an outer region of the second side). As shown, the first and second sides substantially oppose one another. Gear components used with the rotary units, rotary mechanisms, and other applications of the invention typically include gear teeth. Any operable gear tooth configuration and/or type are optionally used in the rotary units, rotary mechanisms and applications of the invention. Second gear component 106 substantially defines gear structure receiving area 108, which is configured to receive gear structure 110. Gear structure 110 includes support component 112 and third gear components 114. Third gear components 114 are configured to operably engage second gear component 106 such that when third gear components 114 rotate in a first direction, second gear component 106 and rotational component 102 also rotate the first direction. Third gear components 114 are configured to operably engage other gear components, such as a first gear component of another rotary unit such that when the other gear components rotate in a second direction, third gear components 114, second gear component 106, and rotational component 102 all rotate in the first direction. Rotary unit 100 also includes retaining mechanism 116 (shown as a wall or lip in this exemplary embodiment) that is structured to retain gear structure 110 at least partially in gear structure receiving area 108. As further shown in FIG. 1I, for example, in some embodiments during rotary unit assembly retaining mechanism 116 is attached to rotational component 102, once gear structure 110 is positioned in gear structure receiving area 108, via attachment components 118 (e.g., which clip into corresponding notches (not within view) in rotational component 102 in this representative embodiment).

Rotary unit 100 also includes implements 120 shown as beads that can be used, for example, as part of a massaging device or the like. Essentially any implement (e.g., type(s) and/or number on a given rotational component, etc.) is optionally adapted for use with the rotary units of the present invention, e.g., depending on the intended application of a given rotary unit. Representative implements that are optionally used include one or more of, e.g., a blade, a razor, a prong, a peg, a claw, a tine, a chain, a stake, a column, a pillar, an arch, a bracket, a gear component, a bristle, a plume, an abrasive component, an elastomeric component, a nail filing component, a nail buffing component, a hair cutting component, a massaging component, a post, or the like. Some exemplary implements 200-210 are also illustrated from side elevational views in, e.g., FIGS. 2 A-F.

In addition, rotary unit 100 also includes drive mechanism component receiving area 122 (shown as a hole disposed through rotational component 102) that is configured to receive a drive mechanism component, such as a drive shaft or a portion thereof. Other exemplary drive mechanism components are described herein or otherwise known in the art.

FIGS. 3 A-G schematically illustrate a rotary unit or components thereof according to one embodiment of the invention. As shown, rotary unit 300 includes rotational component 302, which includes first gear component 304 extending from a first side, and second gear component 306 on a second side and substantially defining gear structure receiving area 308. Rotary unit 300 also includes gear structure 310, which includes third gear components 312 rotatably coupled to support component 314. As also shown, gear structure 310 includes hole 316 that is structured to align with drive mechanism component receiving area 318 of rotational component 302, e.g., to receive a drive mechanism component, such as a drive shaft about which gear structure 310 and rotational component 302 rotate.

Rotary unit 300 also includes a retaining mechanism that is configured to retain gear structure 310 in position relative to rotational component 302 such that the components can operably engage one another during operation. The retaining mechanism of rotary unit 300 includes groove or track 320 disposed approximately around gear structure receiving area 308 in rotational component 302. In addition, the retaining mechanism also includes projections 322 of gear structure 310 that insert into groove or track 320 such that gear structure 310 is retained and rotates within gear structure receiving area 308.

In some embodiments, the rotational components of the rotary units of the invention include implements that are configured to effect the movement of one or more other components (e.g., propeller components or the like) when the rotational components rotate and the implements operably engage the other components. To illustrate, rotational component 302 of rotary unit 300 also includes gear component 324 that is configured to operably engage other gear components of other components, e.g., to effect rotation of those components when rotational component 302 rotates.

FIGS. 4 A-G schematically show another exemplary embodiment of a rotary unit of the invention. As shown, rotary unit 400 includes rotational component 402 that includes first and second surfaces that substantially oppose one another. First gear component 404 is disposed on the first surface of rotational component 402 and is configured to operably engage third gear components of another rotary unit. Second gear component 406 is disposed on the second surface of rotational component 402 and substantially defines gear structure receiving area or cavity 408.

Rotary unit 400 also include gear structure 410, which includes support structure 412 and third gear components 414 rotatably coupled to support structure 412. Rotary unit 400 also includes a retaining mechanism formed, in part, by groove or track 416 formed in rotational component 402. Circular projection 418 disposed on support structure 412 of gear structure 410 is configured to fit within groove or track 416 such that gear structure 410 is retained, yet permitted to rotate, within gear structure receiving area 408. As also shown, rotary unit 400 also includes implements 420 (shown as blades) extending from a surface of rotational component 402.

FIGS. 5 A and B schematically illustrate a rotary unit according to another exemplary embodiment of the invention. As shown, rotary unit 500 includes rotational component 502. First gear component 504 extends from a first side of rotational component 502, while gear structure 506 engages a second gear component in a gear structure receiving area on a second side of rotational component 502 and partially extends from the gear structure receiving area. Gear structure includes third gear components 508 rotatably coupled to support structure 510. Rotary unit 500 also includes a retaining mechanism formed, in part, by groove or track 512 formed in the gear structure receiving area of rotational component 502. Circular projection 514 disposed on support structure 510 of gear structure 506 is configured to fit within groove or track 512 such that gear structure 506 is retained, yet permitted to rotate, within the gear structure receiving area of rotational component 502. First gear component 504 is configured to engage one or more third gear components of another rotary unit. Third gear components 508 are configured to engage the second gear component in the gear structure receiving area and a first gear component of another rotary unit.

FIGS. 6 A-G schematically show a rotary unit or components thereof according to another representative embodiment of the invention. As shown, rotary unit 600 includes rotational component 602. Rotational component 602 includes first gear component 604 on a first side and second gear component 606 on a second side. Second gear component 606 substantially defines a gear structure receiving area of rotational component 602. Rotary unit 600 also includes gear structure 608 disposed within the gear structure receiving area. Gear structure 608 includes third gear components 610 rotatably coupled to support component 612. Third gear components 610 are configured to operably engage second gear component 606 of rotational component 602 and the first gear component of another rotary unit or another gear component, such as a component of a drive mechanism or the like. Gear structure 608 also includes hole or aperture 614, which is structured to align with drive mechanism component receiving area 616 of rotational component 602, e.g., to receive a drive mechanism component, such as a drive shaft about which gear structure 608 and rotational component 602 rotate. Rotary unit 600 also includes a retaining mechanism that is configured to retain and permit gear structure 608 to rotate within the gear structure receiving area of rotational component 602. In particular, support component 612 of gear structure 608 includes partially circular indentation 618 and rotational component 602 comprises projection 620 (e.g., an elevated circular track or the like). Projection 620 is configured to at least partially fit and move within partially circular indentation 618 to retain gear structure 608 at least partially within the gear structure receiving area when second gear component 606 and third gear components 610 operably engage one another. In some embodiments, gear structures comprise projections, such as projection 620 and rotational components comprise the substantially or partially circular indentation (e.g., a circular track or groove structured to receive the projection).

Rotary unit 600 also includes implements 622 that are rotatably coupled to rotational component 602. As shown, rotatably coupled implements 622 include gear components 624 that are configured to operably engage a corresponding gear component on a neighboring rotary unit when the neighboring rotary unit is disposed suitably proximal to rotary unit 600. In these embodiments, during operation, as neighboring rotary units counter-rotate relative to one another, rotatably coupled implements, such as implements 622 (e.g., shown as bristles suitable for a toothbrush, household cleaning device, or the like) also rotate. To further illustrate, rotary unit 600 includes gear component 626 that is configured to operably engage rotatably coupled implements disposed on a neighboring rotary unit.

FIGS. 7 A-C schematically show a rotary unit according to one embodiment of the invention. As shown, rotary unit 700 includes rotational component 702, which includes first gear component 704 on a first side. Rotary unit 700 also includes a gear structure 706 disposed and able to rotate within a gear structure receiving area rotational component 702. Lip or wall 708 retains gear structure 706 in the gear structure receiving area. Rotary unit 700 also includes alignment components that are structured to align rotary units relative to one another, e.g., in a given device or other application. In particular, the first side of rotational component 702 includes circular groove 710, while the second side of rotational component 702 includes circular ridge 712. Circular groove 710 is configured to receive a circular ridge (e.g., circular ridge 812) of another rotary unit (e.g., rotary unit 800), which circular ridge is configured to rotate within circular groove 710. In contrast, circular ridge 712 is configured to fit and rotate within a circular groove (e.g., circular groove 810) of another rotary unit (e.g., rotary unit 800). In some embodiments, the first side of rotational component 702 includes circular ridge 712, while the second side of rotational component 702 includes circular groove 710.

Rotary unit 700 also include drive mechanism component receiving area 714 that is configured to receive a drive mechanism component (e.g., drive mechanism component 816 (shown as a drive shaft) of rotary unit 800). Rotational component 702 is configured to rotate about a drive mechanism component (e.g., drive mechanism component 816 of rotary unit 800), while first gear component 704 operably engages a gear component (e.g., a gear component of a gear structure) of another rotary unit (e.g., a rotary unit, such as a rotary unit 800) and gear components of gear structure 706 operably engage another gear component (e.g., a first gear component) of yet another rotary unit (e.g., another rotary unit, such as another rotary unit 800). As also shown, a surface of rotational component 702 also includes multiple implements 716 (shown as razors or cutting edges) that are optionally used in hair cutting devices or other applications.

FIGS. 8A-C schematically show a rotary unit according to one embodiment of the invention. As shown, rotary unit 800 includes rotational component 802, which includes first gear component 804 on a first side. Rotary unit 800 also includes a gear structure 806 disposed and able to rotate within a gear structure receiving area rotational component 802. Lip or wall 808 retains gear structure 806 in the gear structure receiving area. Rotary unit 800 also includes alignment components that are structured to align rotary units relative to one another, e.g., in a given device or other application. In particular, the first side of rotational component 802 includes circular groove 810, while the second side of rotational component 802 includes circular ridge 812. Circular groove 810 is configured to receive a circular ridge (e.g., circular ridge 712) of another rotary unit (e.g., rotary unit 700), which circular ridge is configured to rotate within circular groove 810. In contrast, circular ridge 812 is configured to fit and rotate within a circular groove (e.g., circular groove 710) of another rotary unit (e.g., rotary unit 700). In some embodiments, the first side of rotational component 802 includes circular ridge 812, while the second side of rotational component 802 includes circular groove 810.

Rotary unit 800 also include drive mechanism component receiving area 814 that is configured to receive a drive mechanism component (e.g., drive mechanism component 816 of a rotary unit 800). In the embodiment shown, drive mechanism component receiving area 814 includes a female threaded region that is configured to receive a male threaded region of drive mechanism component 816 of another rotary unit 800. As described above, another rotary unit (such as a rotary unit 700) is configured to fit between two rotary units 800 and rotate around a drive mechanism component 816 of one of the rotary units 800. As also shown, a surface of rotational component 802 also includes multiple implements 818 (shown as razors or cutting edges) that are optionally used in hair cutting devices or other applications.

FIGS. 9A-L schematically depict an exemplary rotary unit or components thereof according to one embodiment of the invention. As shown, rotary unit 900 includes rotational component 902 that is configured to rotate around rotational axis 904. Rotational component 902 includes first surface 906 and second surface 908. First surface 906 includes gear component 910 (e.g., a sun gear component, etc.) that is configured to operably engage one or more gear components of at least a second rotational component (not shown) when rotational component 902 is disposed proximal to the second rotational component such that when the rotational component 902 rotates in a first direction, the second rotational component rotates in a second direction. In addition, second surface 908 comprises gear component 912 (e.g., a ring gear component, etc.) that is configured to operably engage one or more gear components (via gear components 914) of a third rotational (not shown) component when rotational component 902 is disposed proximal to the third rotational component such that when rotational component 902 rotates in the first direction, the second rotational component rotates in the second direction.

Gear structure 915 includes support component 917 and gear components 914 (e.g., planetary gear components or the like), which are rotatably coupled to support component 917. Support component 917 of gear structure 915 also includes friction reducing materials 919 (shown as elevated or pointed surface features) to reduce friction as rotational component 902 rotates relative to support component 917. As also shown in, for example, FIGS. 9J-L, surface 916 of the rotational component 902 comprises implement 918 (shown as a plurality of bristles), which surface 916 is configured to rotate substantially non-perpendicular to rotational axis 904. In this embodiment, for example, surface 916 of rotational component 902 is configured to rotate substantially parallel to rotational axis 904.

Rotary unit 900 also includes friction reducing materials 920 (shown as roller balls) disposed on first surface 906 of rotational component 902 to reduce friction as rotational component 902 rotates relative to another rotational component. In the embodiments in which friction reducing materials are utilized, essentially any friction reducing material is optionally adapted for use with the rotary units of the invention. Other exemplary embodiments include, for example, coatings (e.g., TEFLON®, etc.), lubricants, surface features, and/or the like. Rotational mechanisms typically include one or more rotary units 900. Exemplary rotational mechanisms are described further herein.

As further shown in FIG. 9I, for example, in some embodiments during rotary unit assembly retaining mechanism 922 is attached to another portion of rotational component 902, once gear structure 915 is positioned in a gear structure receiving area, via attachment components 924 (e.g., which clip into corresponding notches (not within view) in the portion of the rotational component that includes retaining mechanism 922 in this representative embodiment).

In addition, rotary unit 900 also includes drive mechanism component receiving area 925 (shown as a hole disposed through rotational component 902) that is configured to receive a drive mechanism component, such as a drive shaft or a portion thereof. Other exemplary drive mechanism components are described herein or otherwise known in the art.

FIGS. 10A-M schematically depict an exemplary rotary unit or components thereof according to one embodiment of the invention. As shown, rotary unit 1000 includes rotational component 1002 that is configured to rotate around rotational axis 1004. Rotational component 1002 includes first surface 1006 and second surface 1008. First surface 1006 includes gear component 1010 (e.g., a sun gear component, etc.) that is configured to operably engage one or more gear components of at least a second rotational component (not shown) when rotational component 1002 is disposed proximal to the second rotational component such that when the rotational component 1002 rotates in a first direction, the second rotational component rotates in a second direction. In addition, second surface 1008 comprises gear component 1012 (e.g., a ring gear component, etc.) that is configured to operably engage one or more gear components (via gear components 1014) of a third rotational (not shown) component when rotational component 1002 is disposed proximal to the third rotational component such that when rotational component 1002 rotates in the first direction, the third rotational component rotates in the second direction (e.g., in the same direction as the second rotational component).

Gear structure 1015 includes support component 1017 and gear components 1014 (e.g., planetary gear components or the like), which are rotatably coupled to support component 1017. Support component 1017 of gear structure 1015 also includes friction reducing materials 1019 (shown as elevated or pointed surface features) to reduce friction as rotational component 1002 rotates relative to support component 1017. As also shown in, for example, FIGS. 10K-M, surface 1016 of the rotational component 1002 comprises implement 1018 (shown as a plurality of bristles), which surface 1016 is configured to rotate substantially non-perpendicular to rotational axis 1004. In this embodiment, for example, surface 1016 of rotational component 1002 is configured to rotate substantially parallel to rotational axis 1004.

Rotary unit 1000 also includes friction reducing materials 1020 (shown as elevated surface features) disposed on first surface 1006 of rotational component 1002 to reduce friction as rotational component 1002 rotates relative to another rotational component. In the embodiments in which friction reducing materials are utilized, essentially any friction reducing material is optionally adapted for use with the rotary units of the invention. Other exemplary embodiments include, for example, coatings (e.g., TEFLON®, etc.), lubricants, surface features, and/or the like. In some embodiments of the rotary units of the invention, friction reducing materials are not utilized. Rotational mechanisms typically include one or more rotary units 1000. Exemplary rotational or rotary mechanisms are described further herein.

In addition, rotary unit 1000 also includes drive mechanism component receiving area 1024 (shown as a hole disposed through rotational component 1002) that is configured to receive a drive mechanism component, such as a drive shaft or a portion thereof. Other exemplary drive mechanism components are described herein or otherwise known in the art.

To further illustrate, FIGS. 11A-G schematically show a rotary unit or components thereof according to an exemplary embodiment of the invention. As shown, rotary unit 1100 includes rotational component 1102 that is configured to rotate around rotational axis 1104. Rotational component 1102 includes first surface 1106 and second surface 1108. First surface 1106 includes gear component 1110 (e.g., a sun gear component, etc.) that is configured to operably engage one or more gear components (via gear components 1114) of at least a second rotational component (not shown) when rotational component 1102 is disposed proximal to the second rotational component such that when the rotational component 1102 rotates in a first direction, the second rotational component rotates in a second direction. In addition, second surface 1108 comprises gear component 1112 (e.g., a ring gear component, etc.) that is configured to operably engage one or more gear components of a third rotational (not shown) component when rotational component 1102 is disposed proximal to the third rotational component such that when rotational component 1102 rotates in the first direction, the third rotational component rotates in the second direction (e.g., in the same direction as the second rotational component).

Gear structure 1115 includes support component 1117 and gear components 1114 (e.g., planetary gear components or the like), which are rotatably coupled to support component 1117. Support component 1117 of gear structure 1115 also includes friction reducing materials 1119 (shown as elevated or pointed surface features) to reduce friction as rotational component 1102 rotates relative to support component 1117. As also shown in, for example, FIGS. 11E-G, surface 1116 of the rotational component 1102 comprises implement 1118 (shown as a plurality of bristles in this exemplary embodiment), which surface 1116 is configured to rotate substantially non-perpendicular to rotational axis 1104. In this embodiment, for example, surface 1116 of rotational component 1102 is configured to rotate substantially parallel to rotational axis 1104. Rotational mechanisms typically include one or more rotary units 1100. Exemplary rotational mechanisms are described further herein.

In addition, rotary unit 1100 also includes drive mechanism component receiving area 1124 (shown as a hole disposed through rotational component 1102) that is configured to receive a drive mechanism component, such as a drive shaft or a portion thereof. Other exemplary drive mechanism components are described herein or otherwise known in the art.

FIGS. 12A-F schematically show a rotary unit or components thereof according to an exemplary embodiment of the invention. As shown, rotary unit 1200 includes rotational component 1202 that includes gear component 1210 (e.g., a sun gear component, etc.) that is configured to operably engage one or more gear components of at least a second rotational component (not shown) when rotational component 1202 is disposed proximal to the second rotational component such that when the rotational component 1202 rotates in a first direction, the second rotational component rotates in a second direction. In addition, rotational component 1202 comprises gear component 1212 (e.g., a ring gear component, etc.) that is configured to operably engage one or more gear components (via gear components 1214) of a third rotational (not shown) component when rotational component 1202 is disposed proximal to the third rotational component such that when rotational component 1202 rotates in the first direction, the third rotational component rotates in the second direction. Rotational component 1202 is structured similar to rotational component 1002 described herein, but further includes recessed area 1203, which is described below.

Gear structure 1215 includes support component 1217 and gear components 1214 (e.g., planetary gear components or the like), which are rotatably coupled to support component 1217. Support component 1217 of gear structure 1215 also includes friction reducing materials 1219 (shown as elevated or pointed surface features) to reduce friction as rotational component 1202 rotates relative to support component 1217. As also shown, gear structure 1215 also includes retaining features 1220 that are structured to fit and move within recessed area 1203 when gear structure 1215 is disposed in the gear structure receiving area of rotational component 1202. Retaining features 1220 further align and retain gear structure 1215 relative to rotational component 1202. In some embodiments, retaining features 1220 are not included. Although not shown, rotary unit 1200 also typically includes one or more implements. Rotational mechanisms typically include one or more rotary units 1200. Exemplary rotational mechanisms are described further herein.

In addition, rotary unit 1200 also includes drive mechanism component receiving area 1224 (shown as a hole disposed through rotational component 1202) that is configured to receive a drive mechanism component, such as a drive shaft or a portion thereof. Other exemplary drive mechanism components are described herein or otherwise known in the art.

FIGS. 13A-E schematically show components of rotary unit according to one exemplary embodiment of the invention. As shown, the rotary unit includes rotational component 1302 and gear component 1304 (e.g., a planetary gear component or the like). Although not shown, rotational component 1302 typically includes one or more implements (e.g., gear components, bristles, prongs, blades, etc.). Rotational component 1302 includes gear component 1310 (e.g., a sun gear component, etc.) that is configured to operably engage or mesh with gear component 1304. Rotational mechanisms that include these components are described further herein.

FIGS. 14A-D schematically show a rotary unit or components thereof according to an exemplary embodiment of the invention. As shown, rotary unit 1400 includes rotational component 1402 that includes gear component 1410 (e.g., a sun gear component, etc.), gear component 1412 (e.g., a ring gear component, etc.), and gear structure receiving area 1413. Gear component 1410 substantially fixedly extends from first surface 1406 of rotational component 1402. Gear component 1410 is configured to operably engage or mesh with one or more other gear components of another rotary unit when gear component 1410 is disposed proximal to the other gear components. Gear component 1412 substantially fixedly extends from second surface 1408 of rotational component 1402. Gear component 1412 communicates with gear structure receiving area 1413. Gear structure receiving area 1413 is configured to receive gear structure 1415.

Gear structure 1415 includes support component 1417 and gear components 1414 (e.g., planetary gear components or the like), which are rotatably coupled to support component 1417. Gear components 1414 are configured to operably engage or mesh with one or more other gear components when gear components 1414 are disposed proximal to the other gear components. Rotational component 1402 is configured to rotate relative to support component 1417, which support component 1417 is substantially fixedly positioned when rotational component 1402 rotates relative to support component 1417. Gear components 1414 are configured to rotate relative to rotational component 1402. Gear structures that include support components 1417 are described further herein. Although not shown, rotary unit 1400 also typically includes one or more implements. Rotational mechanisms typically include one or more rotary units 1400. Exemplary rotational mechanisms are described further herein.

FIGS. 15A-D schematically illustrate a rotary unit according to one embodiment of the invention. As shown, rotary unit 1500 includes rotational component 1502 that includes first sun gear component 1504 and second sun gear component 1506 on first and second surfaces, respectively, of rotational component 1502, which substantially oppose one another. First sun gear component 1504 is configured to operably engage one or more gear components of at least a second rotational component (not shown) when rotational component 1502 is disposed proximal to the second rotational component such that when rotational component 1502 rotates in a first direction, the second rotational component rotates in a second direction. Second sun gear component 1506 is configured to operably engage one or more gear components of at least a third rotational component (not shown) when rotational component 1502 is disposed proximal to the third rotational component such that when rotational component 1502 rotates in the first direction, the third rotational component rotates in the second direction. Exemplary gears that are optionally adapted for use with the rotary units, rotational mechanisms, and related applications of the invention are also described in, e.g., Dudley, *Handbook of Practical Gear Design* (*Mechanical Engineering Series*), CRC Press, $1^{st}$ Ed. (1994) and Litvin and Fuentes, *Gear Geometry and Applied Theory*, Cambridge University Press; $2^{nd}$ Ed. (2004), which are both incorporated herein in their entirety for all purposes.

Rotary unit 1500 also includes hole 1508 disposed through rotational component 1502. Hole 1508 is configured to receive, e.g., a drive mechanism component (e.g., an axle, a shaft, a gear structure component, etc.) or a support component such that rotational component 1502 can rotate around the drive mechanism component, the support component, or the like. Rotational component 1502 also includes friction reducing materials 1510 (shown as elevated or pointed surface features) to reduce friction as rotational component 1502 rotates relative to, e.g., other rotational component. In addition, rotational component 1502 also include implements 1512 on a surface of rotational component 1502 that is configured to rotate substantially non-perpendicular to a rotational axis of rotary unit 1500. Essentially any implement is optionally adapted for use with rotary unit 1500, including the exemplary implements described herein. Rotary unit 1500 is typically included in a rotational mechanism, a device or the like. Exemplary rotational mechanisms that include rotary unit 1500 are described herein. In addition, representative devices that are optionally adapted to include rotary unit 1500 are also described herein.

FIGS. 16A-Q schematically illustrate a rotary unit or components thereof according to one embodiment of the invention. As shown, rotary unit 1600 includes rotational component 1602 that includes first ring gear component 1604 and second ring gear component 1606 on first and second surfaces, respectively, of rotational component 1602, which substantially oppose one another. First ring gear component 1604 is configured to operably engage one or more gear components of at least a second rotational component (not shown) when rotational component 1602 is disposed proximal to the second rotational component such that when rotational component 1602 rotates in a first direction, the second rotational component rotates in a second direction. Second ring gear component 1606 is configured to operably engage one or more gear components of at least a third rotational component (not shown) when rotational component 1602 is disposed proximal to the third rotational component such that when rotational component 1602 rotates in the first direction, the third rotational component rotates in the second direction.

Rotary unit 1600 also includes hole 1608 disposed through rotational component 1602. Hole 1608 is configured to receive, e.g., a drive mechanism component (e.g., an axle, a shaft, a gear structure component, etc.) or a support component such that rotational component 1602 can rotate around the drive mechanism component, the support component, or the like. Exemplary drive mechanism components and support components are described herein. Although not shown, rotational component 1602 optionally also includes friction reducing materials (e.g., elevated or pointed surface features, surface coatings, roller balls, etc.) to reduce friction as rotational component 1602 rotates relative to, e.g., other rotational component. In addition, rotational component 1602 also include implements 1510 on a surface of rotational component 1602 that is configured to rotate substantially non-perpendicular to a rotational axis of rotary unit 1600. Essentially any implement is optionally adapted for use with rotary unit 1600, including the exemplary implements described herein. Rotary unit 1600 is typically included in a rotational mechanism, a device or the like. Exemplary rotational mechanisms that include rotary unit 1600 are described herein. In addition, representative devices that are optionally adapted to include rotary unit 1600 are also described herein.

In some embodiments, rotary unit 1600 also includes gear structure 1612, which includes support component 1614 and first planetary gear components 1616 and second planetary gear components 1618 rotatably coupled to support component 1614. As shown, first planetary gear components 1616 are configured to operably engage or mesh with first ring gear component 1604, second planetary gear components 1618 are configured to operably engage or mesh with second ring gear component 1606, and rotational component 1602 is configured to rotate relative to support component 1614, which is substantially fixedly positioned (e.g., in an assembled rotational mechanism, device, etc.) when rotational component 1602 rotates relative to support component 1614. As also shown, for example, in FIGS. 16 A and B, respectively, first ring gear component 1604 at least partially defines first gear structure receiving area 1605 and second ring gear component 1606 at least partially defines second gear structure receiving area 1607. First gear structure receiving area 1605 and second gear structure receiving area 1607 are configured to receive first portion 1622 and second portion 1624, respectively, of support component 1614 of gear structure 1612. First portion 1622 and second portion 1624 of support component 1614 of gear structure 1612 are described, e.g., further below.

FIG. 16G schematically shows an exploded side view of gear structure 1612 according to one embodiment of the invention. As shown, threaded region 1620 of first portion 1622 of support component 1614 inserts into a threaded region receiving area (not within view in FIG. 16G) of second portion 1624 of support component 1614 during assembly of gear structure 1612. In addition, first planetary gear components 1616 are rotatably coupled to second portion 1624 of support component 1614 via pronged retaining elements 1626 and second planetary gear components 1618 are rotatably coupled to first portion 1622 of support component 1614 via pronged retaining elements 1628 during assembly of gear structure 1612. As also shown, first portion 1622 and second portion 1624 of support component 1614 include friction reducing materials 1630 (shown as elevated or pointed surface features), e.g., to minimize friction when rotational component 1602 rotates relative to support component 1614 during operation of assembled rotary unit 1600. To further illustrate, FIG. 16M schematically shows an exploded view of rotary unit 1600 with first portion 1622 and second portion 1624 of support component 1614 of gear structure 1612 prior to assembly with rotational component 1602.

To further illustrate, FIG. 16K schematically illustrates gear structure 1612 prior to assembly with another gear structure 1612 from a side view according to one embodiment of the invention. As shown, during assembly, threaded region 1632 of one support component 1614 is inserted into threaded region receiving area 1634 of another support component 1614 such that the assembled support components 1614 are substantially fixedly positioned relative to one another, e.g., when rotational components 1602 of rotary units 1600 rotate relative to support components 1614. Essentially any attachment technique is optionally utilized to attach support components 1614 of gear structures 1612 to one another or first portion 1622 and second portion 1624 of support component 1614 to one another. Some exemplary techniques include, for example, bonding, welding, adhering, or the like. In some embodiments, multiple support components 1614 are fabricated as single integral part (e.g., as a molded part or the like).

III. Exemplary Rotary Mechanisms

In certain embodiments, the invention provides rotary or rotational mechanisms that include two or more rotational components or rotary units (e.g., 2, 3, 4, 5, 6, 7, 8, 9, 10, 11, 12, 13, 14, 15, or more rotational components or rotary units). Rotary mechanisms also typically include at least one counter-rotational mechanism operably coupled to one or more of the rotational components. The counter-rotational mechanism is generally configured to effect substantially simultaneous counter-rotation of the rotational components relative to one another when movement of at least a portion of the counter-rotational mechanism is effected. Rotary mechanisms also typically include drive mechanisms operably coupled to the counter-rotational mechanism and/or rotational components. Drive mechanisms are typically configured to effect movement of at least the portion of the counter-rotational mechanisms such that the rotational components substantially simultaneously counter-rotate relative to one another. In some embodiments, for example, multiple rotary units are included as components (e.g., rotational components and counter-rotational mechanisms, etc.) of rotary mechanisms.

In some embodiments, rotary units are operably coupled to one another via one or more shafts. To illustrate one embodiment, FIG. 17A schematically depicts rotary units 100 and drive mechanism component 1702 (shown as a shaft) prior to assembly. As shown, gear component 1704 is fixedly coupled to shaft 1702 and is configured to operably engage third gear components 114 (not within view in FIGS. 17 A and B) of a rotary unit 100 in assembled rotary mechanism 1700. During assembly, shaft 1702 is inserted through drive mechanism component receiving areas 122 (shown as holes, e.g., in FIG. 1A) of rotary units 100 to operably couple rotary units 100 to one another. FIG. 17B schematically illustrates rotary units 100 and shaft 1702 following assembly. Suitable shafts include a variety of cross-sectional shapes (e.g., circular, oval, triangular, square, rectangular, polygonal, etc.). In some embodiments, a given shaft includes multiple cross-sectional shapes. In some of these embodiments, individual rotary units include drive mechanism component receiving areas (e.g., holes, apertures, etc.) that correspond to those different cross-sectional shapes. In some embodiments, for example, one member of a pair of neighboring rotary units includes a square hole that fits on a square cross-section of a shaft, while the other member of the pair includes a circular hole that fits on a circular cross-section of the shaft. In these embodiments, the rotary unit with the square hole typically rotates in a substantially fixed position relative to the shaft, whereas the rotary unit with the circular hole typically rotates substantially free or independent relative to the shaft.

To further illustrate, FIGS. 18 A-C schematically show rotary mechanism 1800 assembled from pairs of rotary units 700 and 800, which are both described further herein. More specifically, FIG. 18A schematically shows an individual pair of rotary units 700 and 800 prior to assembly of rotary mechanism 1800 from side views. FIG. 18B schematically shows partially assembled rotary mechanism 1800 with the rotary units of FIG. 18A from side views. FIG. 18C schematically illustrates rotary mechanism 1800 that includes multiple pairs of rotary units 700 and 800.

In some embodiments, rotary units are operably coupled to one another via one or more shafts. To illustrate one embodiment, FIG. 19A schematically depicts rotary units 900, drive mechanism component 1902 (shown as a shaft), and cap component 1903 prior to assembly. As shown, gear component 1904 is fixedly coupled to shaft 1902 and is configured to operably engage or mesh with gear components 914 of a rotary unit 900 in assembled rotary mechanism 1900. During assembly, shaft 1902 is inserted through drive mechanism component receiving areas 925 (shown as a hole, e.g., in FIG. 9A) of rotary units 900 to operably couple rotary units 900 to one another. Shaft 1902 operably connects with cap component 1903 in assembled rotary mechanism 1900, e.g., to hold rotary units 900 in position relative to one another. FIG. 19B schematically illustrates rotary units 900, shaft 1902, and cap component 1903 following assembly of rotary mechanism 1900. The directional arrows in FIG. 19B schematically depict that neighboring pairs of rotary units 900 in rotary mechanism 1900 are configured to counter-rotate relative to one another. FIG. 19C schematically shows a portion of a rotary mechanism that includes rotary units 900 with implements 918.

FIGS. 20A-O schematically show a rotary mechanism or components thereof according to exemplary embodiments of the invention. As shown, rotary mechanism 2000 includes four rotary units that each include rotational component 1302 and gear component 1304. Rotary mechanism 2000 also includes a drive mechanism that includes shafts 2002 and motors 2004. Motors 2004 are configured to effect rotation of shafts 2002. As shown, the drive mechanism is configured to effect rotation of gear components 1304 such that rotational components 1302 of neighboring or adjacent pairs of rotary units rotate in opposite directions. See, e.g., the directional arrows in FIG. 20H, which schematically depict the counter-rotation of neighboring pairs of rotational components 1302. As shown, one shaft 2002 is operably connected to a first set of two non-neighboring gear components 1304, while the other shaft 2002 is operably connected to a second set of two non-neighboring gear components 1304 that is different from the first set of two non-neighboring of gear components 1304. The two shafts 2002 are configured to rotate in opposite directions. See, e.g., the directional arrows associated with shafts 2002 in FIGS. 20 H and I. As also shown, surfaces 1305 of rotational components 1302 are configured to rotate substantially non-perpendicular to a rotational axis of rotational components 1302.

Any suitable drive mechanism is optionally utilized with these rotary mechanisms. For example, FIG. 20L schematically depicts a portion of a drive mechanism from a side view. As shown, the drive mechanism includes motor 2004 (depicted as a dual shaft motor) that is configured to effect rotation of shafts 2002 in opposite directions via meshing pairs of gear components 2006. To further illustrate, FIGS. 20M-O schematically depict portions of a drive mechanism. As shown, motor 2004 is configured to effect rotation of shafts 2002 in opposite directions via a gear train that includes gear components 2008.

In addition, rotary mechanism 2000 also includes positioning component 2010 (shown as a frame structure) that is configured to position rotary units relative to one another. As shown, shafts 2002 are positioned relative to positioning component 2010 via mount brackets 2012, which permit rotation of shafts 2002. As also shown, positioning component 2010 also includes a plurality of friction reducing materials 2014 (shown as roller balls) disposed on a surface of positioning component 2010 to reduce friction as rotational components 1302 rotates relative to positioning component 2010. In the embodiments in which friction reducing materials are utilized, essentially any friction reducing material is optionally adapted for use with the rotary mechanisms of the invention. Other exemplary embodiments include, for example, coatings (e.g., TEFLON®, etc.), lubricants, surface features, and/or the like. FIG. 20G schematically depicts positioning component 2016 according to another exemplary embodiment.

FIGS. 21A-E schematically show rotary mechanisms or components thereof according to exemplary embodiments of the invention. As shown, rotary mechanism 2100 includes drive mechanism component 2102, which includes ring gear component 2104 and a gear structure. The gear structure includes support component 2106 and planetary gear component 2108 rotatably coupled to support component 2106. Planetary gear component 2108 is configured to operably engage ring gear component 2104 of drive mechanism component 2102 and gear component 1410 of rotary unit 1400. Drive mechanism component 2102 also includes motor 2110, which is configured to effect rotation of ring gear component 2104 via shaft 2112. Shaft 2112 is fixedly connected to ring gear component 2104. When ring gear component 2104 rotates, it effects the counter-rotation of neighboring pairs of rotary units 1400 relative to one another. See, e.g., the directional arrows associated with FIGS. 21 B and C, which schematically depict the counter-rotation of neighboring pairs of rotary units 1400. As also shown, in assembled rotary mechanism 2100, support component 2106 is operably connected to support components 1417 of rotary units 1400 such that support component 2106 and support components 1417 are substantially fixedly positioned relative to one another when ring gear component 2104 effects the counter-rotation of neighboring pairs of rotary units 1400 relative to one another. Gear structures that include support components 1417 are described further herein. To further illustrate, FIG. 21D schematically depicts rotary mechanism 2114, which includes rotary units 1400 with implements 1418. In addition, FIG. 21E schematically illustrates rotary mechanism 2116, which includes rotary units 1400 with implements 1418 and dual shaft motor 2118.

The gear structures of the invention include various embodiments. To illustrate, FIG. 22A schematically illustrates gear structure 1415 prior to assembly with another gear structure 1415 from a side view according to one embodiment of the invention. As shown, gear structure 1415 includes support component 1417 and gear components 1414 (e.g., planetary gear components or the like), which are rotatably coupled to support component 1417. Gear components 1414 are configured to operably engage or mesh with one or more other gear components when gear components 1414 are disposed proximal to the other gear components. During assembly, threaded region 1429 of one support component 1417 is inserted into threaded region receiving area 1427 of another support component 1417 such that the assembled support components 1417 are substantially fixedly positioned relative to one another when rotational components 1402 of rotary units 1400 rotate relative to support components 1417 and to one another. Essentially any attachment technique is optionally utilized to attach support components 1417 to one another. Some exemplary techniques include, for example, bonding, welding, adhering, or the like. In some embodiments, multiple support components 1417 are fabricated as single integral part (e.g., as a molded part or the like). FIG. 22B schematically shows an assembly of four gear structure 1415 from a side view. FIG. 22C schematically depicts the gear structure assembly of FIG. 22B from a rear side view, while FIG. 22D schematically depicts the gear structure assembly of FIG. 22B from a front side view.

To further illustrate, FIG. 22E schematically shows rotary mechanism 2200 that includes the gear structure assembly of FIG. 22B from a sectional view according to one embodiment of the invention. As shown, rotary mechanism 2200 includes four rotary units 1400. Counter-rotation of neighboring rotational components 1402 in rotary mechanism 2200 is effected by drive mechanism component 2202, which includes shaft component 2204 and gear component 2206. FIG. 22F schematically shows rotary mechanism 2200 from a side view. Rotational components 1402 of rotary units 1400 of rotation mechanism 2200 are configured to rotate relative to support components 1417, which support components 1417 are substantially fixedly positioned when rotational components 1402 rotates relative to support components 1417. Gear components 1414 are configured to rotate relative to rotational components 1402.

FIGS. 23A-T schematically depict a rotational mechanism or components thereof according to one embodiment of the invention. To illustrate, FIGS. 23A and C, for example, schematically depicts a portion of rotational mechanism 2300 from an exploded side and exploded side sectional views, respectively. During assembly of rotational mechanism 2300, support component 1614 of one rotary unit 1600 is inserted through hole 1508 of rotary unit 1500 and threaded region 1632 of that support component 1614 is received and retained in threaded region receiving area of another rotary unit 1600.

FIGS. 23E-P schematically show a portion of a drive mechanism component that is utilized to effect counter-rotation of neighboring pairs of rotary unit 1500 and rotary unit 1600 of rotational mechanism 2300. As shown, the portion of the drive mechanism component includes rotational component 2302, which includes ring gear component 2304, hole 2306, and implements 2308. The portion of the drive mechanism component also includes gear structure 2310, which includes support structure 2312 and planetary gear components 2314 rotatably coupled to support structure 2312. Support structure 2312 also includes friction reducing materials 2316 (shown as elevated or pointed surface features) to, e.g., reduce friction between support structure 2312 and rotational component 2302 when rotational component 2302 rotates relative to support structure 2312. Support structure 2312 also includes threaded region 2318, which is received by a corresponding threaded region receiving area of fastener 2320 (e.g., a nut or the like) through hole 2306 to hold gear structure 2310 in position relative rotational component 2302, yet permit rotational component 2302 to rotate relative to support structure 2312 and planetary gear components 2314. In addition, support structure 2312 also includes threaded region receiving area 2322, which is configured to receiving thread region 1632 of a rotary unit 1600, e.g., in assembled rotational mechanism 2300.

As also shown, a shaft 2324 is also fixedly connected to rotational component 2302. Although not shown, a motor or the like is typically operably connected to shaft 2324, which effects the rotation of shaft 2324 and the counter-rotation of neighboring pairs of rotary unit 1500 and rotary unit 1600 of rotational mechanism 2300 (e.g., as schematically depicted by the directional arrows shown, e.g., in FIG. 23S) during operation. In addition, a rotary unit 1600 also operably connects to support component 2326 via threaded region receiving area 1634 of support structure 1614, e.g., such that support structures 1614 of rotary units 1600 and support structure 2312 of gear structure 2310 are substantially fixedly positioned when rotary units 1500, rotary units 1600, and rotational component 2302 rotate relative to one another in rotational mechanism 2300. Essentially any support component is optionally used. In some embodiments, support components are included in or as part of devices, apparatus, or other applications of the rotational mechanisms of the invention. Exemplary support components and applications are described herein.

IV. Exemplary Applications

FIGS. 24 A and B schematically illustrate a rotor tiller or rototiller that includes a rotary mechanism according to one embodiment of the invention. As shown, rotor tiller 2400 includes rotary mechanism 2462 that is operably connected to motor 2404 via shaft 2474. As also shown, rotor tiller 2400 also includes wheels 2402 and handle 2406 coupled to a support structure.

To further illustrate exemplary embodiments of the invention, FIG. 25A schematically shows vehicle 2500 from a side elevational view. As shown, vehicle 2500 includes two rotary mechanisms 2502 and grading blade 2503, which can each be independently raised and lowered. Rotary mechanisms can include various embodiments, including various types of implements (e.g., as described herein or the like). As also shown, vehicle 2500 also includes wheels 2504, driver's compartment 2506, and engine compartment 2508. Vehicle 2500 can be adapted for a wide variety of uses in, e.g., agricultural, construction, military, or other applications. In some embodiments, for example, vehicle 2500 is used to till, grade, and/or otherwise move soil. As another exemplary illustration, FIG. 25B schematically shows vehicle 2501 from a side elevational view. As shown, vehicle 2501 includes rotary mechanism 2510, which can be raised and lowered. As also shown, vehicle 2501 also includes wheels 2504, driver's compartment 2506, and engine compartment 2508. Vehicle 2501 can be adapted for a wide variety of uses. In some embodiments, for example, vehicle 2501 is used to till, grade, and/or otherwise move soil.

In other representative embodiments, the invention provides hair cutting devices, e.g., for cutting facial hair, leg hair, or hair on other body parts. To illustrate, FIGS. 26 A-G illustrate various aspects of a hair cutting device according to one embodiment of the invention. As shown, hair cutting device 2600 includes housing 2602, which comprises surfaces that define cavity 2604 disposed at least partially within housing 2602. Housing 2602 also includes opening 2606 that communicates with cavity 2604. Rotary mechanism 2608 (e.g., similar to the rotary mechanism described with respect to FIG. 18C) is at least partially disposed within cavity 2604. Rotary mechanism 2608 includes multiple rotational components 2610 and 2612 (such as the rotational components described with respect to FIGS. 7 A-C and 8 A-C, etc.) that are configured to substantially coaxially rotate (e.g., coaxially counter-rotate) relative to one another. Rotational components 2610 and 2612 also include cutting implements 2614 (e.g., razor blades or other sharp edges) that are configured to cut hair via opening 2606 when the multiple rotational components 2610 and 2612 substantially coaxially rotate relative to one another and cutting implements 2614 (see, e.g., implements 716 and 818 or the like) contact the hair (see, e.g., FIG. 26F). Rotary mechanism 2608 also includes at least one counter-rotational mechanism, as described herein (see, e.g., the multiple assembled rotational mechanisms schematically depicted in, e.g., FIGS. 18A-C or the like), operably coupled to the multiple rotational components 2610 and 2612. The counter-rotational mechanism is configured to effect substantially simultaneous counter-rotation of the multiple rotational components 2610 and 2612 relative to one another when movement of at least a portion of the counter-rotational mechanism is effected. That is, rotational component 2610 is configured to rotate in a direction that is opposite the direction of rotation of rotational component 2612. In some embodiments, the rotational components are configured to coaxially counter-oscillate relative to one another about an axis of rotation of the rotary mechanism. In some of these embodiments, cutting implements include dual-side cutting edges, e.g., to cutting hair in both directions of the oscillation.

As also shown, hair cutting device 2600 also includes a drive mechanism operably coupled to the counter-rotational mechanism and rotational components. In the embodiment shown, for example, in FIGS. 26A and 26C, the drive mechanism includes motor 2616 (e.g., a stepper motor, a servo motor, etc.), which is configured to effect movement of the counter-rotational mechanism via shaft 2618 such that the multiple rotational components 2610 and 2612 substantially simultaneously counter-rotate relative to one another. As also shown, switch 2617 (e.g., on/off switch, a variable speed control switch, and/or the like) is operably connected to motor 2616. Although not shown, hair cutting device 2608 also typically includes a power source (e.g., a power cord that plugs into a wall socket, a battery (rechargeable or not), a photovoltaic cell, etc.) operably connected to motor 2616.

Hair cutting device 2600 also includes removable structure 2620 (e.g., a shaving foil structure or the like) disposed in opening 2606. Removable structure 2620 comprises holes 2622 via which hair is cut when the multiple rotational components 2610 and 2612 substantially coaxially counter-rotate relative to one another and cutting implements 2614 contact the hair. Hair cutting devices also typically include support structures that are structured to support at least a portion of the rotational components, the counter-rotational mechanism, and/or the drive mechanism within the device housings. As shown in FIG. 26F, for example, hair cutting device 2600 is dimensioned to be hand-held (i.e., person 2621 is holding hair cutting device 2600 in his hand). As shown, e.g., FIG. 26G housing 2602 of hair cutting device 2600 comprises at least one substantially circular cross-section.

FIGS. 27 A-D schematically illustrate an exemplary tooth brushing device or components thereof according to one embodiment of the invention. As shown, tooth brushing device 2700 includes rotary mechanism 2702, which includes a plurality of rotary units 600, as described above. Tooth brushing device 2700 also includes toothbrush head component 2704 and handle component 2706. Toothbrush head component 2704 includes rotary mechanism housing 2708, which partially exposes a portion of the bristles of rotary mechanism 2702 through an opening in rotary mechanism housing 2708 during operation. Toothbrush head gear components 2710 and drive shaft 2712 also extend from a portion of rotary mechanism housing 2708. Drive shaft 2712 is received through drive mechanism receiving areas of rotational components 602 of rotary units 600 of rotary mechanism 2702. Toothbrush head gear components 2710 operably engage gear components 604 and 624 of a rotary unit 600 to effect counter rotation of neighboring rotational components 602 and implements 622 of rotary mechanism 2702. Rotary mechanism cap 2714 attaches to drive shaft 2712 to retain rotary mechanism positioned relative to toothbrush head gear components 2710. Handle component 2706 houses a motor (not within view) the operably connects to toothbrush head gear components 2710 and drive shaft 2712. A power source, such as a rechargeable battery or the like is also housed in handle component 2706 is some embodiments. In certain embodiments, the motor is optionally connected to other types of power sources, such as photovoltaic cells attached to handle component 2706, external power sources, or the like. As also shown, handle component 2706 also include switch 2716, which is used, e.g., to turn tooth brushing device 2700 on and off, regulate speeds or modes of rotary unit rotation, or the like.

FIGS. 28 A and B schematically show an exemplary rotary mechanism or toothbrush head component that is optionally used, e.g., with handle component 2706 of tooth brushing device 2700. As shown, rotary mechanism 2800 includes a plurality of rotary units 600 in which implements 2802 (raised elastomeric regions, e.g., for tooth polishing) have been substituted for implements 622 on several individual rotary units. FIG. 28B schematically shows toothbrush head component 2804, which includes rotary mechanism 2800.

FIG. 29 schematically illustrates an exemplary cleaning device from a side view according to one embodiment of the invention. As shown, cleaning device 2900 includes a rotary mechanism that includes rotary units similar to rotary units 800, which are described further herein. Exemplary uses of cleaning device 3900 include cleaning outdoor cooking grills, dishes, and toilets, among many possible applications.

To further illustrate representative embodiments, rotary units and rotary mechanisms are optionally used or adapted for use in various types of engines and other propulsion devices or systems. For example, FIGS. 30 A-F schematically illustrate a propulsion device or components thereof according to one embodiment of the invention. As shown, propulsion device 3000 includes two rotary mechanisms 3002 and propeller component 3004. Rotary mechanisms 3002 include a plurality of rotary units 300, as described herein. Rotary units 300 are operably coupled to one another via shaft 3006, which includes gear component 3008. Shaft 3006 operably connects to motor 3010 and rotary mechanism cap 3012. Gear component 3008 operably engages third gear components 312 of gear structure 310 of a rotary unit 300 such that when motor 3010 effects the rotation of gear component 3008, gear component 3008 effects the counter rotation of neighboring pairs of rotary units 300. Gear components 324 of rotary units 300 operably engage corresponding gear components of propeller units 3014 (e.g., rotational units or the like) to effect the counter rotation of neighboring pairs of propeller units 3014 of propeller component 3004, and thereby propulsion. Rotary mechanism cap 3012 aligns and maintains the position of rotary units 300 relative to one another. Although two rotary mechanisms 3002 are depicted in this propulsion device embodiment, fewer or more that two rotary mechanisms are optionally used.

FIGS. 32 A-D schematically illustrate a propulsion device or components thereof according to one embodiment of the invention. As shown, propulsion device 3200 includes two rotary mechanisms 3202 and propeller component 3004. Rotary mechanisms 3202 include a plurality of rotational components 3204. Rotational components 3204 are fixedly coupled to one another via shaft 3206. Shaft 3206 operably connects to motor 3010 and rotary mechanism cap 3012. As shown, one shaft 3206 is fixedly coupled to a first set of four non-neighboring gear components 3204, while the other shaft 3206 is fixedly coupled to a second set of four non-neighboring gear components 3204 that is different from the first set of four non-neighboring of gear components 3204. The two shafts 3206 are configured to rotate in opposite directions. See, e.g., the directional arrows associated with the two rotary mechanisms 3202 in FIG. 32B. As shown, in an assembled propulsion device 3200, gear components 3204 of the first and second sets of four non-neighboring of gear components 3204 mesh with corresponding gear components of different propeller units 3014 (e.g., rotational units or the like) of propeller component 3004 such that when the first and second sets of four non-neighboring of gear components 3204 rotate in opposite directions to one another, neighboring pairs of propeller units 3014 of propeller component 3004 counter-rotate relative to one another, and thereby effect propulsion.

Propeller component 3004 of propulsion device 3000 and 3200 includes a plurality of propeller units 3014 (e.g., rotational units or the like), which in this embodiment each include a plurality of propellers 3016. Many different types of propellers are optionally used or adapted for use in the engines or propulsion devices of the invention. In some embodiments, for example, individual propeller components 3004 may have propellers 3016 that differ in size from the propellers of other propeller components in a given propulsion device 3000 or propulsion device 3200. Propeller units 3014 are operably coupled together in propeller component 3004 via propeller component shaft 3018 and propeller component cap 3020. As also shown, certain propeller units 3014 include rotational alignment components 3022, which are positioned and rotate in corresponding rotational positioning components 3107 of propulsion component housing 3100 (e.g., a positioning component or the like), e.g., to prevent propeller units 3014 from contacting propulsion component housing 3100 during operation. See, e.g., FIGS. 31D and E.

The engine and propulsion devices have many different uses. For example, they are optionally used or adapted for use with watercraft (e.g., boats, submarines, surfboards, personal watercraft, diving or scuba propulsion aides, and the like) or aircraft. To illustrate, FIGS. 33 A and B schematically depict boat 3300, which includes several housed propulsion devices 3302. To further illustrate, FIGS. 34 A and B schematically depict aircraft 3400, which includes housed propulsion devices 3402.

FIG. 35A schematically shows cleaning device 3500 that includes a rotary mechanism from a sectional view according to one embodiment of the invention. FIG. 35B schematically shows cleaning device 3500 from a side view. As shown, the rotary mechanism of cleaning device 3500 includes rotary units 900, which each include implements 918. Rotary units 900 are aligned relative to one another and rotate around shaft 3502. The rotary mechanism is positioned relative to housing 3504 via mounting components 3506. As also shown, cleaning device 3500 also includes motor 3508, which effects the counter-rotation of rotary units 900 in the rotary mechanism via drive shaft 3510 and meshed gear components 3512 and 3514. Cleaning device 3500 also includes power source 3516 (e.g., a battery or the like), which is operably connected to motor 3508 and switch 3518 in a handle portion of housing 3504. Cleaning device 3500 is optionally adapted for a variety of uses including, for example, cleaning dishes, cleaning countertops, cleaning floors, cleaning barbeque grills, cleaning ovens, cleaning toilets, buffing automobiles or other vehicles, and the like.

FIGS. 36A-G schematically depict a cleaning device or components thereof. As shown, cleaning device 3600 includes rotary mechanism 3602. Rotary mechanism 3602 includes rotary units 900, which each include implements 918. Rotary units 900 are aligned relative to one another and rotate around shafts 3604. Rotary mechanism 3602 is positioned relative to housing 3606 of head component 3607 via mounting components 3608. As also shown, cleaning device 3600 also includes motor 3610, which effects the counter-rotation of rotary units 900 in rotary mechanism 3602 via drive shaft 3612 and meshed gear components 3614 and 3616. Although not within view, cleaning device 3600 also includes a power source (e.g., a battery or the like) or is connectable with a power source (e.g., via a power cord or the like), which operably connects to motor 3610 and switch 3618. As shown, switch 3618 is disposed on handle component 3620, which operably connects to head component 3607.

FIG. 37 schematically shows rotary mechanism 3700 from a top side view according to one embodiment of the invention. Rotary mechanism 3700 is optionally adapted for use in the cleaning devices and other applications of the invention. Rotary mechanism 3700 includes rotary units 900, which each include implements 918. Rotary units 900 are aligned relative to one another and rotate around shafts 3702. As also shown, rotary mechanism 3700 also includes motor 3704, which effects the counter-rotation of rotary units 900 in rotary mechanism 3700 via drive shaft 3706 and meshed gear components 3708.

FIG. 38 schematically shows cleaning device 3800 that includes rotary mechanism 3602 from a side view according to one embodiment of the invention. As shown, cleaning device 3800 includes head component 3607 (as described above), which is operably connected to handle component 3802. As also shown, handle component 3802 includes switch 3804, which is operably connected to motor 3610 (not within view). Switch 3804 is typically used to turn cleaning device 3800 on and off, varying a rate or mode of rotary unit rotation, and the like.

FIG. 39 schematically shows cleaning device 3900 that includes rotary mechanism 5502 from a side view according to one embodiment of the invention. As shown, cleaning device 3900 includes head component 3607 (as described above), which is operably connected to handle component 3902. As also shown, handle component 3902 includes switch 3904, which is operably connected to motor 3610 (not within view). Cleaning device 3900 also includes suction component 3906, which communicates with an internal cavity of head component 3607 that includes rotary mechanism 3602 and with waste container 3908. Suction component 3906 includes a suction source (e.g., a vacuum source) and a conduit. The suction source is configured to generate suction force sufficient to convey waste from head component 3607 through the conduit to waste container 3908. Switch 3904 is also operably connected to suction component 3906. Switch 3904 is typically used to turn cleaning device 3900 on and off (rotary unit rotation and/or suction), varying a rate or mode of rotary unit rotation and/or suction component suction, and the like.

FIG. 40A schematically shows cleaning device 4000 that includes rotary mechanism 3602 and removable fluid containers 4002 (e.g., a fluid source or the like) and 4004 (e.g., a fluid waste container or the like) prior to assembly from a side view according to one embodiment of the invention. FIG. 40B schematically shows cleaning device 4000 with fluid containers 4002 and 4004 positioned relative to handle 4006 on support components 4003 and 4005, respectively, from a side view. As shown, cleaning device 4000 includes head component 3607 (as described above), which is operably connected to handle component 4006. As also shown, handle component 4006 includes switch 4008, which is operably connected to motor 3610 (not within view).

In some embodiments, cleaning devices or implements include fluid handling mechanisms that can be used, for example, to distribute fluid (e.g., a cleaning fluid, etc.) to a surface to cleaned or the like. To illustrate one exemplary embodiment, cleaning device 4000 includes a fluid handling mechanism that comprises a fluid source (container 4002) and fluid outlet (nozzle 4010) (shown disposed proximal to a surface of head component 3607). The fluid handling mechanism is configured to convey fluid from container 4002 to nozzle 4010, which communicate via fluid conduit 4012. The fluid handling mechanism of cleaning device 4000 also includes pumping mechanism 4014 (e.g., a rotary lobe pump, a rotary gear pump, a screw pump, a gear pump, a peristaltic pump, or the like) that is configured to pump the fluid from container 4002 to nozzle 4010. As also shown, the fluid handling mechanism also includes vaporization component 4016 (e.g., a steam vaporizer or the like) that is configured to vaporize the fluid at least proximal to nozzle 4010. In the embodiment shown, container 4002 is removable from cleaning device 4000 such that container 4002 can be, e.g., refilled with a cleaning fluid, replaced with a new container when container 4002 is fabricated as a consumable component of cleaning device 4000, etc. In some embodiments, containers are fabricated integral or otherwise fixedly attached to cleaning devices. Switch 4008 is also configured to effect operation of pumping mechanism 4014 and vaporization component 4016.

Cleaning device 4000 also includes suction component 4018 (e.g., vacuum source or component, pumping mechanism, and/or the like) that comprises inlet 4020 and outlet 4022. As shown, suction component 4018 is disposed proximal to head component 3607. Outlet 4022 communicates with container 4004 via conduit 4024. Switch 4008 is also configured to effect operation of suction component 4018.

During operation, cleaning fluid is conveyed from container 4002, vaporized, and sprayed from nozzle 4010 to wet a surface to be cleaned. Rotary mechanism 3602 of head component 3607 scrubs the wetted surface and suction component 4018 conveys waste fluid from the wetted surface through inlet 4020 to container 4004. Cleaning devices or implements, or components thereof, that optionally are adapted for use with the cleaning devices of the invention are also described in, e.g., U.S. Provisional Patent Application No. 61/317,746, entitled "CLEANING IMPLEMENTS, CLEANING MATERIAL COMPONENTS, AND RELATED METHODS", filed on Mar. 26, 2010, which is incorporated by reference in its entirety.

To further illustrate, FIGS. 41A-Q schematically show cleaning devices, cleaning material components, or components thereof from various views according to exemplary embodiments of the invention. As shown, cleaning device 4100 includes head component 4102 which includes cleaning material support component 4104 and cleaning surface component 4106. Cleaning material support component 4104 includes cleaning material support component surfaces 4108 that at least partially define cleaning material receiving areas 4110 (shown as cleaning implement cartridge receiving areas). As also shown, cleaning material support components 4104 include openings 4112 that are structured such that cleaning material receiving areas 4110 communicate with cleaning surface component 4106. As shown, cleaning material receiving areas 4110 are configured to receive cleaning material component 4114 (shown as a cleaning implement cartridge that includes a cleaning material roll) such that at least a portion of cleaning material component 4114 is movable to and/or from cleaning material receiving area 4110 to extend over at least a portion of cleaning surface component 4106. In addition, cleaning device 4100 also includes retaining component 4120 (shown as a door structure) that operably engages cleaning material support component 4104 via slide component 4122 in this exemplary embodiment. As shown, head component 4102 also includes rotary mechanism 2116.

Cleaning material component 4114 includes cleaning material support structures 4130 and cleaning material 4126 (shown as a rolled sheet of cleaning material). Cleaning material support structures 4130 (shown as substantially cylindrically-shaped housings) form cavities that are each structured to house and support cleaning material 4126 such that cleaning material 4126 is movable to and/or from cleaning material support structures 4130 via orifices 4132. Orifices 4132 are configured to communicate with openings 4112. Cleaning material support structures and corresponding cleaning material receiving areas are optionally formed to include various cross-sectional shapes, including, e.g., circles, ovals, squares, rectangles, regular n-sided polygons, irregular n-sided polygons, etc. As shown, cleaning material support structure 4130 is configured to be received in cleaning material receiving area 4110 of cleaning device 4100 and cleaning material 4126 is configured to extend over cleaning surface component 4106 of cleaning device 4100 via orifices 4132 and openings 4112.

In some embodiments, cleaning material support structures and/or cleaning materials of cleaning material components include one or more alignment components that are configured to align cleaning materials relative to cleaning material support structures. To illustrate, cleaning material support structures 4130 of cleaning material component 4114 includes rod 4134 that extends within cleaning material support structure 4130. As shown, the alignment component (rod 4134) of cleaning material support structure 4130 inserts into a corresponding central receiving area of the cleaning material roll (cleaning material 4126) to align cleaning material 4126 relative to cleaning material support structures 4130.

In certain embodiments, cleaning devices and/or cleaning material components operably connect, or are operably connectable, to conveyance mechanisms or components thereof to effect conveyance of cleaning materials, e.g., selected incremental distances. In cleaning device 4100, for example, rod 4134 extends through cleaning material support structure 4130 and operably connects to conveyance mechanism component 4140 that is configured to operably engage gear components 4139. In particular, projections 4137 of conveyance mechanism component 4140 are configured to be received by projection receiving areas 4135 of gear components 4139. Gear components 4139 are configured to operably engage gear component 4141 of head component 4102 when cleaning material component 4114 is disposed in cleaning material receiving areas 4110. As shown, gear component 4141 is operably connected to motor 4143 (e.g., a stepper motor, a servo motor, etc.) via shaft 4145. Power source 4147 (shown as a battery, e.g., a disposable battery, a rechargeable battery, etc.) operably connects to motor 4143 to provide power to motor 4143. Essentially any power source is optionally adapted for use with the cleaning devices of the invention. In some embodiments, for example, motors are operably connected to power cords that plug into power outlets. In other exemplary embodiments, photovoltaic cells are mounted cleaning devices to provide power to motors. Motor 4143 effects rotation of cleaning material roll (cleaning material 4126) (via gear components 4139 and 4141) selected distances such that cleaning material 4126 is positioned at selected positions relative to cleaning surface component 4106. Although not within view, motor 2118 is also operably connected to power source 4147. Motor 2118 effects rotation of rotary mechanism 2116.

Typically, cleaning material support components of cleaning devices and/or cleaning material components include one or more alignment features that are structured to align those components relative to one another when the cleaning material components are disposed in the cleaning material receiving areas of the cleaning devices. In one exemplary embodiment, for example, cleaning material support structure 4130 and cleaning material support component 4104 include alignment features 4142 and 4144, respectively (schematically shown as corresponding tongue and groove-type components), that are structured to align cleaning material support structure 4130 relative to cleaning material support component 4104 cleaning device 4100.

The cleaning devices of the invention typically include one or more handle components. As shown in FIGS. 41N-P, for example, cleaning device 4100 includes handle 4146 operably connected to head component 4102. Handle 4146 is pivotally connected to head component 4102 via pivot mechanism 4148 (shown as a ball and socket mechanism). As also shown, handle 4146 includes switch 4150 which is operably connected to motor 4143. Switch 4150 is used to effect movement of cleaning material 4126 via the conveyance mechanism described above.

In some embodiments, cleaning devices include fluid handling mechanisms that can be used, for example, to distribute fluid (e.g., a cleaning fluid, etc.) to a surface to cleaned, to a cleaning material of a cleaning device (e.g., to moisten the cleaning material prior to or during use of the cleaning device, etc.), and/or the like. To illustrate one exemplary embodiment, cleaning device 4100 includes a fluid handling mechanism that comprises a fluid source (container 4154) and fluid outlets (nozzles 4152) (shown disposed proximal to a surface of head component 4102). The fluid handling mechanism is configured to convey fluid from container 4154 to nozzles 4152, which communicate via fluid conduit 4156. The fluid handling mechanism of cleaning device 4100 also includes pumping mechanism 4158 (e.g., a rotary lobe pump, a rotary gear pump, a screw pump, a gear pump, a peristaltic pump, or the like) that is configured to pump the fluid from container 4154 to nozzles 4152. As also shown, the fluid handling mechanism also includes vaporization component 4160 (e.g., a steam vaporizer or the like) that is configured to vaporize the fluid at least proximal to nozzles 4152. In the embodiment shown, container 4154 is removable from cleaning device 4100 such that container 4154 can be, e.g., refilled with a cleaning fluid, replaced with a new container when container 4154 is fabricated as a consumable component of cleaning device 4100, etc. In some embodiments, containers are fabricated integral or otherwise fixedly attached to cleaning devices. Switch 4150 is also configured to effect operation of pumping mechanism 4158 and vaporization component 4160. As shown in FIG. 41Q, for example, head component 4102 of cleaning device 4100 includes elevational element 4162 from a side view. Elevational elements are also described in, e.g., U.S. Provisional Patent Application No. 61/317,746, entitled "CLEANING IMPLEMENTS, CLEANING MATERIAL COMPONENTS, AND RELATED METHODS", filed on Mar. 26, 2010, which is incorporated by reference in its entirety.

In some embodiments, the cleaning devices or components thereof of the invention are optionally adapted for use as part of various types of robotic cleaning implements. Exemplary robotic cleaners or aspect there of that are optionally adapted for use with these cleaning implements or components are described in, e.g., U.S. Pat. No. 7,571,511, entitled "Autonomous floor cleaning robot" to Jones et al, which issued Aug. 11, 2009; U.S. Pat. No. 7,620,476, entitled "Autonomous surface cleaning robot for dry cleaning" to Morse et al., which issued Nov. 17, 2009; U.S. Pat. No. 7,636,982, entitled "Autonomous floor cleaning robot" to Jones et al, which issued Dec. 29, 2009; and U.S. Pat. No. 7,761,954, entitled "Autonomous surface cleaning robot for wet and dry cleaning" to Ziegler et al., which issued Jul. 27, 2010; and U.S. Patent Application Publication Nos. US 2009/0281661, entitled "Application of localization, positioning & navigation systems for robotic enabled mobile products" by Dooley et al., which published Nov. 12, 2009 and US 2009/0306822, entitled "Multi-function robotic device" by Augenbraun et al., which published Dec. 10, 2009, which are each incorporated by reference herein in their entirety.

Device components (e.g., rotary units, rotary mechanisms, drive mechanism components, gear components, shafts, rotational components, device housings, doors, support structures, etc.) are optionally formed by various fabrication techniques or combinations of such techniques including, e.g., cast molding, stamping, machining, embossing, extrusion, engraving, injection molding, etching (e.g., electrochemical etching, etc.), or other techniques. These and other suitable fabrication techniques are generally known in the art and described in, e.g., Molinari et al. (Eds.), Metal Cutting and High Speed Machining, Kluwer Academic Publishers (2002), Altintas, Manufacturing Automation: Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W. J. T. Associates (2000), Whelan, Injection Molding of Thermoplastics Materials, Vol. 2, Chapman & Hall (1991), Rosato, Injection Molding Handbook, 3.sup.rd Ed., Kluwer Academic Publishers (2000), Fisher, Extrusion of Plastics, Halsted Press (1976), and Chung, Extrusion of Polymers: Theory and Practice, Hanser-Gardner Publications (2000), which are each incorporated by reference. Exemplary materials optionally used to fabricate device components include, e.g., metal, glass, wood, polymethylmethacrylate, polyethylene, polydimethylsiloxane, polyetheretherketone, polytetrafluoroethylene, polystyrene, polyvinylchloride, polypropylene, polysulfone, polymethylpentene, and polycarbonate, among many others. In certain embodiments, following fabrication, device components are optionally further processed, e.g., by painting, coating surfaces with a hydrophilic coating, a hydrophobic coating, or the like.

Exemplary rotary units, rotational mechanisms, related applications, and other aspects, which are optionally adapted, e.g., for use with the rotary units and rotational mechanisms described herein are also described in, e.g., U.S. patent application Ser. No. 12/577,326, entitled "ROTARY UNITS, MECHANISMS, AND RELATED DEVICES", filed on Oct. 12, 2009, U.S. Provisional Patent Application No. 61/104,748, entitled "ROTARY UNITS, MECHANISMS, AND RELATED DEVICES", filed on Oct. 12, 2008, International Application No. PCT/US2009/060386, entitled "ROTARY UNITS, MECHANISMS, AND RELATED DEVICES", filed on Oct. 12, 2009, U.S. Provisional Patent Application No. 61/365,290, entitled "ROTARY UNITS, MECHANISMS, AND RELATED DEVICES", filed on Jul. 16, 2010, and U.S. Provisional Patent Application No. 61/317,746, entitled "CLEANING IMPLEMENTS, CLEANING MATERIAL COMPONENTS, AND RELATED METHODS", filed on Mar. 26, 2010, which are each incorporated herein by reference in their entirety for all purposes.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A rotary unit, comprising:
at least one rotational component comprising at least first and second gear components and at least one gear structure receiving area, wherein the first gear component substantially fixedly extends from a first surface of the rotational component, wherein the first gear component is configured to operably engage one or more other gear components of another rotary unit when the first gear component is disposed proximal to the other gear components, wherein the second gear component substantially fixedly extends from a second surface of the rotational component, wherein the second gear component communicates with the gear structure receiving area, wherein the gear structure receiving area is configured to receive one or more gear structures or components thereof, and wherein at least one surface of the rotational component comprises at least one implement; and, at least one gear structure comprising at least one support component and at least a third gear component rotatably coupled to the support component, wherein the third gear component is configured to operably engage one or more other gear components when the third gear component is disposed proximal to the other gear components, and wherein the rotational component is configured to rotate relative to the support component, which support component is substantially fixedly positioned when the rotational component rotates relative to the support component.

2. The rotary unit of claim 1, wherein the first and second surfaces substantially oppose one another.

3. The rotary unit of claim 1, wherein the third gear component is configured to rotate relative to the rotational component.

4. The rotary unit of claim 1, wherein the first gear component comprises at least one sun gear component.

5. The rotary unit of claim 1, wherein the second gear component comprises at least one ring gear component.

6. The rotary unit of claim 1, wherein the third gear component comprises at least one planetary gear component.

7. The rotary unit of claim 1, wherein the surface of the rotational component that comprises the implement is configured to rotate substantially non-perpendicular to a rotational axis of the rotary unit.

8. The rotary unit of claim 1, wherein the surface of the rotational component that comprises the implement is configured to rotate substantially parallel to a rotational axis of the rotary unit.

9. A rotational mechanism comprising the rotary unit of claim 1.

10. A rotary mechanism, comprising:
at least two rotary units that each comprises:
at least one rotational component that comprises at least one sun gear component and at least one ring gear component, and
at least one gear structure that comprises at least one support component and at least one planetary gear component rotatably coupled to the support component, and wherein the planetary gear component is configured to operably engage the ring gear component,
wherein the sun gear component of at least a first rotary unit operably engages the planetary gear component of at least a second rotary unit such that when the rotational component of the first rotary unit rotates in a first direction, the rotational component of the second rotary unit rotates in a second direction,
wherein the gear structure of the first rotary unit is operably connected to the gear structure of the second rotary unit such that the support components are substantially fixedly positioned relative to one another at least when the rotational component of the first rotary unit rotates in the first direction, the rotational component of the second rotary unit rotates in the second direction, and
wherein at least one surface of at least one of the rotational components comprises at least one implement.

11. The rotary mechanism of claim 10, wherein at least two of the rotational components are non-concentrically disposed relative to one another.

12. The rotary mechanism of claim 10, comprising at least three, at least four, at least five, at least six, at least seven, at least eight, at least nine, at least ten, or more rotary units.

13. A method of rotating an implement, the method comprising:
providing a rotary mechanism that comprises at least three rotary units that each comprises at least one rotational component that comprises at least one sun gear component and at least one ring gear component, and at least one gear structure that comprises at least one support component and at least one planetary gear component rotatably coupled to the support component, wherein the planetary gear component operably engages the ring gear component, wherein the sun gear component of at least a first rotary unit operably engages the planetary gear component of at least a second rotary unit, wherein the sun gear component of the second rotary unit operably engages the planetary gear component of at least a third rotary unit, wherein the gear structure of the second rotary unit is operably connected to the gear structures of the first and third rotary units such that the support components are substantially fixedly positioned relative to one another at least when the rotational components of the rotary units rotate relative to one another, and wherein at least one of the rotational components comprises at least one implement; and,
moving at least a portion of one or more of the rotary units such that the rotational components of first and third rotary units rotate in a first direction and the rotational component of the second rotary unit rotates in a second direction, thereby rotating the implement.

* * * * *